US009012368B2

(12) United States Patent
Wilmer et al.

(10) Patent No.: US 9,012,368 B2
(45) Date of Patent: Apr. 21, 2015

(54) SYSTEM AND METHOD FOR GENERATING AND/OR SCREENING POTENTIAL METAL-ORGANIC FRAMEWORKS

(75) Inventors: Christopher E. Wilmer, Evanston, IL (US); Michael Leaf, Evanston, IL (US); Randall Q. Snurr, Evanston, IL (US); Omar K. Farha, Mortongrove, IL (US); Joseph T. Hupp, Northfield, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 13/543,189

(22) Filed: Jul. 6, 2012

(65) Prior Publication Data

US 2013/0143768 A1     Jun. 6, 2013

Related U.S. Application Data

(60) Provisional application No. 61/504,925, filed on Jul. 6, 2011.

(51) Int. Cl.
*G01N 33/20* (2006.01)
*C40B 30/00* (2006.01)
(Continued)

(52) U.S. Cl.
CPC ............... *G01N 33/20* (2013.01); *B01J 20/223* (2013.01); *B01D 53/04* (2013.01); *F17C 11/00* (2013.01); *F17C 11/002* (2013.01); *F17C 11/005* (2013.01); *F17C 11/007* (2013.01); *C09K 3/00* (2013.01); *C07F 1/08* (2013.01); *C07F 3/06* (2013.01); *B01J 20/226* (2013.01); *B01J 20/0211* (2013.01); *B01J 20/0214* (2013.01); *B01J 20/0237* (2013.01);
(Continued)

(58) Field of Classification Search
None
See application file for complete search history.

(56) References Cited

U.S. PATENT DOCUMENTS 7,964,535 B2     6/2011  Carlson
2003/0004364 A1  1/2003  Yaghi et al.
(Continued)

FOREIGN PATENT DOCUMENTS

EP     0 978 499 B2    2/2000

OTHER PUBLICATIONS

Sumida et al., "Hydrogen storage and carbon dioxide capture in an iron-based sodalite-type metal-organic framework (Fe-BTT) discovered via high-throughput methods," Chem. Sci. 2010, 1:184-191.*
(Continued)

*Primary Examiner* — Samuel Woolwine
*Assistant Examiner* — Kaijiang Zhang
(74) *Attorney, Agent, or Firm* — The Marbury Law Group PLLC

(57) ABSTRACT

A system and method for systematically generating potential metal-organic framework (MOFs) structures given an input library of building blocks is provided herein. One or more material properties of the potential MOFs are evaluated using computational simulations. A range of material properties (surface area, pore volume, pore size distribution, powder x-ray diffraction pattern, methane adsorption capability, and the like) can be estimated, and in doing so, illuminate unidentified structure-property relationships that may only have been recognized by taking a global view of MOF structures. In addition to identifying structure-property relationships, this systematic approach to identify the MOFs of interest is used to identify one or more MOFs that may be useful for high pressure methane storage.

29 Claims, 29 Drawing Sheets
(20 of 29 Drawing Sheet(s) Filed in Color)

(51) Int. Cl.
| | |
|---|---|
| C40B 60/06 | (2006.01) |
| B01J 20/22 | (2006.01) |
| B01D 53/04 | (2006.01) |
| F17C 11/00 | (2006.01) |
| C09K 3/00 | (2006.01) |
| C07F 1/08 | (2006.01) |
| C07F 3/06 | (2006.01) |
| B01J 20/02 | (2006.01) |
| B01D 53/02 | (2006.01) |

(52) U.S. Cl.
CPC ............ *B01J 20/0244* (2013.01); *B01D 53/02* (2013.01); *B01D 2253/204* (2013.01); *B01D 2257/102* (2013.01); *B01D 2257/7025* (2013.01); *Y02C 20/20* (2013.01)

(56) References Cited

U.S. PATENT DOCUMENTS

2009/0143596 A1* 6/2009 Eddaoudi et al. ............ 548/103
2010/0225650 A1 9/2010 Grzybowski et al.

OTHER PUBLICATIONS

Wu et al., "Three-Dimensional Metal-Organic Frameworks Based on Functionalized Tetracarboxylate Linkers: Synthesis, Strucures, and Gas Sorption Studies," Inorg. Chem. 2009, 48:2436-2442.*
Mellot-Draznieks et al., "Assembling molecular species into 3D frameworks: Computational design and structure solution of hybrid materials," Prog. Solid State Chem. 2005, 33:187-197.*
Mellot-Draznieks et al., "Hybrid Organic-Inorganic Frameworks: Routes for Computational Design and Structure Prediction," Angew. Chem. Int. Ed. 2004, 43:6290-6296.*
Keskin, "Accelerating development of metal organic framework membranes using atomically detailed simulations", PhD Dissertation, Georgia Institute of Technology, ( 2009) p. 28.
International Search Report and Written Opinion received in connection with international application No. PCT/US2012/045782, dtd Apr. 1, 2013.
International Preliminary Report on Patentability received in connection with international application No. PCT/US2012/045782, dtd Jan. 16, 2014.
Rosi, N.L., Eckert, J., Eddaoudi, M., Vodak, D.T., Kim, J., O'Keeffe, M. & Yaghi, O.M. Hydrogen storage in microporous metal-organic frameworks. *Science* 300, 1127-1129 (2003).
Wang, B., Côté, A.P., Furukawa, H., O'Keeffe, M. & Yaghi, O.M. Colossal cages in zeolitic imidazolate frameworks as selective carbon dioxide reservoirs. *Nature* 453, 207-211 (2008).
Ferey, G. Physical chemistry: Trapped gas. *Nature* 436, 187-188 (2005).
Matsuda, R., Kitaura, R., Kitagawa, S., Kubota, Y., Belosludov, R.V., Kobayashi, T.C., Sakamoto, H., Chiba, T., Takata, M., Kawazoe, Y. & Mita, Y. Highly controlled acetylene accommodation in a metalorganic microporous material. *Nature* 436, 238-241 (2005).
Düren, T., Sarkisov, L., Yaghi, O.M. & Snurr, R.Q. Design of new materials for methane storage. *Langmuir* 20, 2683-2689 (2004).
Murray, L., Dinca, M. & Long, J. Hydrogen storage in metal-organic frameworks. *Chem. Soc. Rev.* 38, 1294-1314 (2009).
Seo, J., Whang, D., Lee, H., Jun, S., Oh, J., Jeon, Y. & Kim, K. A homochiral metal-organic porous material for enantioselective separation and catalysis. *Nature* 404, 982-986 (2000).
Bradshaw, D., Prior, T.J., Cussen, E.J., Claridge, J.B. & Rosseinsky, M.J. Permanent microporosity and enantioselective sorption in a chiral open framework. *J. Am. Chem. Soc* 126, 6106-6114 (2004).
Düren, T. & Snurr, R.Q. Assessment of isoreticular metal-organic frameworks for adsorption separations: A molecular simulation study of methane/n-butane mixtures. *J. Phys. Chem. B* 108, 15703-15708 (2004).
Watanabe, T., Keskin, S., Nair, S. & Sholl, D.S. Computational identification of a metal organic framework for high selectivity membrane-based $CO_2/CH_4$ separations: Cu(hfipbb)(H2hfipbb)0.5. *Phys. Chem. Chem Phys.* 11, 11389 (2009).
Liu, B., Yang, Q., Xue, C., Zhong, C., Chen, B. & Smit, B. Enhanced adsorption selectivity of hydrogen/methane mixtures in metal-organic frameworks with interpenetration: A molecular simulation study. *J. Phys. Chem. C* 112, 9854-9860 (2008).
Li, J.-R., Kuppler, R.J. & Zhou, H.-C. Selective gas adsorption and separation in metal-organic frameworks. *Chem. Soc. Rev.* 38, 1477-1504 (2009).
Corma, A. From microporous to mesoporous molecular sieve materials and their use in catalysis. *Chem. Rev.* 97, 2373-2419 (1997).
Lee, J., Farha, O.K., Roberts, J., Scheidt, K.A., Nguyen, S.T. & Hupp, J.T. Metal-organic framework materials as catalysts. *Chem. Soc. Rev.* 38, 1450-1459 (2009).
Lan, A., Li, K., Wu, H., Olson, D.H., Emge, T.J., Ki, W., Hong, M. & Li, J. A luminescent microporous metal-organic framework for the fast and reversible detection of high explosives. *Angew. Chem. Int. Ed.* 2334-2338 (2009).
Franke, M.E., Simon, U., Moos, R., Knezevic, A., Muller, R. & Plog, C. Development and working principle of an ammonia gas sensor based on a refined model for solvate supported proton transport in zeolites. *Phys. Chem. Chem. Phys.* 5, 5195-5198 (2003).
Allendorf, M.D., Houk, R.J.T., Andruszkiewicz, L., Talin, A.A., Pikarsky, J., Choudhury, A., Gall, K.A. & Hesketh, P.J. Stress-induced chemical detection using flexible metal-organic frameworks. *J. Am. Chem.Soc.* 130, 14404-14405 (2008).
Kokotailo, G.T., Lawton, S.L., Olson, D.H. & Meier, W.M. Structure of synthetic zeolite ZSM-5. *Nature* 272, 437-438 (1978).
Kitagawa, S., Kitaura, R. & Noro, S.-ichiro Functional porous coordination polymers. *Angew. Chem. Int.Ed.* 43, 2334-2375 (2004).
Li, H., Eddaoudi, M., O'Keeffe, M. & Yaghi, O. Design and synthesis of an exceptionally stable and highly porous metal-organic framework. *Nature* 402, 276-279 (1999).
Ferey, G. Hybrid porous solids: past, present, future. *Chem. Soc. Rev.* 37, 191-214 (2008).
Furukawa, H., Ko, N., Go, Y.B., Aratani, N., Choi, S.B., Choi, E., Yazaydin, A.O., Snurr, R.Q., O'Keeffe, M., Kim, J. & Yaghi, O.M. Ultrahigh porosity in metal-organic frameworks. *Science* 329, 424-428 (2010).
Ferey, G., Mellot-Draznieks, C., Serre, C., Millange, F., Dutour, J., Surble, S. & Margiolaki, I. A chromium terephthalate-based solid with unusually large pore volumes and surface area. *Science* 309, 2040-2042 (2005).
Chae, H.K., Siberio-Perez, D.Y., Kim, J., Go, Y., Eddaoudi, M., Matzger, A.J., O'Keeffe, M. & Yaghi, O.M. A route to high surface area, porosity and inclusion of large molecules in crystals. *Nature* 427, 523-527 (2004).
Farha, O.K., Yazaydin, A.Ö., Eryazici, I., Malliakas, C.D., Hauser, B.G., Kanatzidis, M.G., Nguyen, S.T., Snurr, R.Q. & Hupp, J.T. De novo synthesis of a metal-organic framework material featuring ultrahigh surface area and gas storage capacities. *Nat. Chem.* 2, 944-948 (2010).
Zaworotko, M.J. Materials science: Designer pores made easy. *Nature* 451, 410-411 (2008).
Moulton, B. & Zaworotko, M.J. From molecules to crystal engineering: Supramolecular isomerism and polymorphism in network solids. *Chem. Rev.* 101, 1629-1658 (2001).
Ockwig, N.W., Delgado-Friedrichs, O., O'Keeffe, M. & Yaghi, O.M. Reticular chemistry: Occurrence and taxonomy of nets and grammar for the design of rameworks. *Acc. Chem. Res.* 38, 176-182 (2005).
Yaghi, O.M., O'Keeffe, M., Ockwig, N.W., Chae, H.K., Eddaoudi, M. & Kim, J. Reticular synthesis and the design of new materials. *Nature* 423, 705-714 (2003).
Eddaoudi, M., Kim, J., Rosi, N., Vodak, D., Wachter, J., O'Keeffe, M. & Yaghi, O.M. Systematic design of pore size and functionality in isoreticular MOFs and their application in methane storage. *Science* 295, 469-472 (2002).
Eddaoudi, M., Moler, D.B., Li, H., Chen, B., Reineke, T.M., O'Keeffe, M. & Yaghi, O.M. Modular chemistry: Secondary building units as a basis for the design of highly porous and robust metal—organic carboxylate frameworks. *Acc. Chem. Res.* 34, 319-330 (2001).

(56) References Cited

OTHER PUBLICATIONS

Perry IV, J.J. & Perman, J.A. Design and synthesis of metal-organic frameworks using metal-organic polyhedra as supermolecular building blocks. *Chem. Soc. Rev.* 38, 1400-1417 (2009).

Vaidhyanathan, R., Iremonger, S.S., Shimizu, G.K.H., Boyd, P.G., Alavi, S. & Woo, T.K. Direct observation and quantification of CO2 binding within an amine-functionalized nanoporous solid. *Science* 330, 650-653 (2010).

Frost, H., Düren, T. & Snurr, R.Q. Effects of surface area, free volume, and heat of adsorption on hydrogen uptake in metal-organic frameworks. *J. Phys. Chem. B* 110, 9565-9570 (2006).

Earl, D.J. & Deem, M.W. Toward a database of hypothetical zeolite structures. *Ind. Eng. Chem. Res.* 45, 5449-5454 (2006).

Haldoupis, E., Nair, S. & Sholl, D.S. Pore size analysis of >250 000 hypothetical zeolites. *Phys. Chem. Chem. Phys.* 13, 5053-5060 (2011).

Ch. Baerlocher & L.B. McCusker Database of zeolite structures: http://www.iza-structure.org/databases/, Retrieved Oct. 22, 2012.

Lin, X., Telepeni, I., Blake, A.J., Dailly, A., Brown, C.M., Simmons, J.M., Zoppi, M., Walker, G.S., Thomas, K.M., Mays, T.J., Hubberstey, P., Champness, N.R. & Schroder, M. High capacity hydrogen adsorption in Cu(II) tetracarboxylate framework materials: The role of pore size, ligand functionalization, and exposed metal sites. *J. Am. Chem. Soc.* 131, 2159-2171 (2009).

Ma, S., Sun, D. Simmons, J.M., Collier, C.D., Yuan, D. & Zhou, H.C. Metal-organic framework from an anthracene derivative containing nanoscopic cages exhibiting high methane uptake. *J. Am. Chem. Soc.* 130, 1012-1016 (2008).

Chui, S.S.-Y., Lo, S.M.-F., Charmant, J.P.H., Orpen, A.G. & Williams, I.D. A chemically functionalizable nanoporous material [Cu3(TMA)2(H2O)3]n. *Science* 283, 1148-1150 (1999).

Barthelet, K., Marrot, J., Riou, D. & Férey, G. A breathing hybrid organic-inorganic solid with very large pores and high magnetic characteristics. *Angew. Chem. Int. Ed.* 41, 281-284 (2002).

Rappé, A.K., Casewit, C.J., Colwell, K.S., Goddard III, W.A. & Skiff, W.M. Uff, a full periodic table force field for molecular mechanics and molecular dynamics simulations. *J. Am. Chem. Soc.* 114, 10024-10035 (1992).

Menon, V.C. & Komarneni, S. Porous adsorbents for vehicular natural gas storage: A review. *J. Porous Mater.* 5, 43-58 (1998).

Zhou, W. Methane storage in porous metal-organic frameworks: Current records and future perspectives. *Chem. Rec.* 10, 200-204 (2010).

Senkovska, I. & Kaskel, S. High pressure methane adsorption in the metal-organic frameworks Cu3(btc)2, Zn2(bdc)2dabco, and Cr3F(H2O)2O(bdc)3. *Micropor. Mesopor. Mat.* 112, 108-115 (2008).

Deng, H., Doonan, C.J., Furukawa, H., Ferreira, R.B., Towne, J., Knobler, C.B., Wang, B. & Yaghi, O.M. Multiple functional groups of varying ratios in metal-organic frameworks. *Science* 327, 846-850 (2010).

Wu, H., Simmons, J.M., Liu, Y., Brown, C.M., Wang, X.-S., Ma, S., Peterson, V.K., Southon, P.D., Kepert, C.J., Zhou, H.-C., Yildirim, T. & Zhou, W. Metal-organic frameworks with exceptionally high methane uptake: Where and how is methane stored? *Chem. Eur. J.* 16, 5205-5214 (2010).

Walton, K.S. & Snurr, R.Q. Applicability of the BET method for determining surface areas of microporous metal—organic frameworks. *J. Am. Chem. Soc* 129, 8552-8556 (2007).

Xu, Q. & Zhong, C. A general approach for estimating framework charges in metal-organic frameworks. *J. Phys. Chem. C* 114, 5035-5042 (2010).

Wilmer, C.E. & Snurr, R.Q. Towards rapid computational screening of metal-organic frameworks for carbon dioxide capture: Calculation of framework charges via charge equilibration. *Chem. Eng. J* in press, Chem. Eng. J. 2011, 171:775.

Rappé, A.K., Casewit, C.J., Colwell, K.S., Goddard III, W.A. & Skiff, W.M. Uff, a full periodic table force field for molecular mechanics and molecular dynamics simulations, *J. Am. Chem. Soc.* 114, 10024-10035 (1992).

Martin, M.G. & Siepmann, J.I. Transferable potentials for phase equilibria. 1. United-atom description of nalkanes. *J. Phys. Chem. B* 102, 2569-2577 (1998).

Mayo, S.L., Olafson, B.D. & Goddard III, W.A. Dreiding: a generic force field for molecular simulations. *J. Phys. Chem* 94, 8897-8909 (1990).

Dietzel, P.D.C., Morita, Y., Blom, R. & Fjellvåg, H. An in situ high-temperature single-crystal investigation of a dehydrated metal-organic framework compound and field-induced magnetization of one-dimensional metal-oxygen chains. *Angew. Chem. Int. Ed.* 44, 6354-6358 (2005).

Navarro, J.A.R., Barea, E., Salas, J.M., Masciocchi, N., Galli, S., Sironi, A., Ania, C.O. & Parra, J.B. H, N, CO, and CO sorption properties of a series of robust sodalite-type microporous coordination polymers. *Inorganic Chemistry* 45, 2397-2399 (2006).

Koh, K., Wong-Foy, A.G. & Matzger, A.J. A crystalline mesoporous coordination copolymer with high microporosity. *Angew. Chem. Int. Ed.* 47, 677-680 (2008).

Park, K.S., Ni, Z., Côté, A.P., Choi, J.Y., Huang, R., Uribe-Romo, F.J., Chae, H.K., O'Keeffe, M. & Yaghi, O.M. Exceptional chemical and thermal stability of zeolitic imidazolate frameworks. *Proc. Natl. Acad. Sci. U.S.A.* 103, 10186-10191 (2006).

Frost, H., Düren, T. & Snurr, R.Q. Effects of surface area, free volume, and heat of adsorption on hydrogen uptake in metal-organic frameworks. *J. Phys. Chem. B* 110, 9565-9570 (2006).

Chen, Z.X., Xiang, S.C., Liao, T.B., Yang, Y.T., Chen, Y.S., Zhou, Y.M., Zhao, D.Y. & Chen, B.L. A new multidentate hexacarboxylic acid for the construction of porous metal-organic frameworks of diverse structures and porosities. *Cryst. Growth Des.* 10, 2775-2779 (2010).

\* cited by examiner

SYSTEM AND METHOD FOR GENERATING AND/OR SCREENING POTENTIAL METAL-ORGANIC FRAMEWORKS

CROSS-REFERENCE TO RELATED APPLICATIONS

This application claims priority to U.S. Provisional Application Ser. No. 61/504,925, which was filed on 6 Jul. 2011, and is entitled "System And Method For Generating And/Or Screening Potential Metal-Organic Frameworks" (the "'925 Application"). This application also is related to U.S. application Ser. No. 13/543,283, PCT Application No. PCT/US2012/045782, and PCT Application No. PCT/US2012/045787, each of which was filed on 6 Jul. 2012, and is entitled "System And Method For Generating And/Or Screening Potential Metal-Organic Frameworks" ("the '283 Application," the "'782 Application," and the "'787 Application," respectively). The entire disclosures of the '925 Application, the '283 Application, the '782 Application, and the '787 Application are incorporated by reference into this application.

STATEMENT REGARDING FEDERALLY SPONSORED RESEARCH OR DEVELOPMENT

This invention was made with government support under HDTRA1-09-1-0007 awarded by Defense Threat Reduction Agency and DE-FG02-08ER15967 awarded by Department of Energy. The government has certain rights in the invention.

BACKGROUND

Highly porous materials have found widespread application in the manipulation of small molecules for gas storage, separating mixtures, catalysis, analysis, and detection. Among the many types of porous materials, metal-organic frameworks (MOFs) can provide exceptional characteristics or material properties. MOFs include porous crystals created from modular molecular "building blocks," which can, in principle, be combined in an almost unlimited number of combinations. MOFs can provide exceptional characteristics or material properties, not only with regard to their relatively high surface area, porosity and stability, but also for the ease with which the MOFs can be synthesized based on designs conceived a priori. This latter benefit stems from the use of modular molecular "building blocks" that self-assemble into predictable crystal structures. Due to this predictability and the abundance of known modular building blocks, there have been reports of novel MOFs over the past few years and many in-depth investigations of their properties and functionality. While these reports showcase the success of the modular building block approach, they also belie the underlying combinatorial difficulty of finding the MOF with desired material properties for a given application, such as improved material properties or the best material properties for the application.

Our work shares much in spirit with at least one known database of hypothetical zeolites that was recently rapidly screened for gas adsorption properties. However, synthesis of such novel zeolites can be significantly more difficult than novel MOFs. For example, it is believed that less than 200 different zeolite structures have been synthesized to date, compared to thousands of MOFs over a much shorter time period.

As there are millions of possible MOFs even when considering libraries of fewer than one hundred building blocks, it can be difficult and time-consuming to find the MOF or MOFs having desired properties that are better than other MOFs or the best for a particular application.

BRIEF DESCRIPTION

Past investigations into MOFs have focused on a relatively small fraction of the possible combinations of building blocks. In accordance with one or more embodiments of the presently described inventive subject matter, systems and methods for computationally generating all, or at least a substantially large number, of conceivable (e.g., hypothetical or potential) MOFs from a given chemical library or corpus of building blocks. In one aspect, one or more of these potential MOFs (e.g., MOFs of interest) are screened to find one or more candidate MOFs for a given application or to find the MOFs likely to exhibit one or more characteristics of interest that are relevant to a given application. In one embodiment, 137,953 hypothetical or potential MOFs are generated and the pore size distribution, surface area, and methane storage capacity is calculated for the hypothetical MOFs. As used herein, the term "hypothetical" includes predicted or potential MOFs, and is not limited to imaginary or impossible MOFs. For example, a hypothetical MOF can include an MOF that is generated using one or more embodiments described herein and that may be actually formed. In addition to finding novel structure-property relationships, over 300 MOFs with better methane storage capacity than several or all known materials have been discovered using one or more embodiments of the systems and methods described herein. One or more of these MOFs had a capacity almost 50% higher than the U.S. Department of Energy target of 180 $cm^3$(STP)/$cm^3$. Methyl-functionalized MOFs were frequently the top performers, and a MOF referred to as NOTT-107 is identified as a promising methane storage material. The predicted capacity of this MOF was experimentally confirmed.

In accordance with one embodiment of the inventive subject matter described herein, the predictable assembly of building blocks into MOFs is used to systematically generate a relatively large number of possible structures (within one or more constraints, as described below) given an input library of building blocks. The material properties or characteristics of these possible MOFs can be predicted using computational simulations. A range of material properties can be predicted for these MOFs, such as surface area, pore volume, pore size distribution, powder x-ray diffraction pattern, adsorption capability (e.g., methane adsorption capability, carbon dioxide adsorption capability, and the like). In doing previously unidentified structure-property relationships may be discovered.

In addition to identifying structure-property relationships, one or more of the possible MOFs may be identified as MOFs of interest that can be more useful for a representative, specific application (such as but not limited to methane storage) relative to one or more other existing MOFs and/or possible MOFs. In one embodiment, the NOTT-107 MOF is identified and synthesized based on structure-property insights from the database generated by one or more embodiments described herein. This MOF is predicted to have better methane storage capacity at 35 bar than one or more other MOFs, such as PCN-14, a MOP having a known methane storage capacity that is relatively high. An experimental adsorption isotherm agrees well with these predictions, thus demonstrating the accuracy and utility of the systematic approach described herein in accordance with one embodiment. Various other MOFs, such as NU-125 and wMOF-1, were identified and predicted to provide enhanced sorption and storage capacities, synthesized and subsequently tested to validate one or more predictive aspects of the inventive subject matter.

In accordance with one embodiment, a system for generating and/or screening one or more potential MOFs is provided. The system includes a generation module that is configured to receive building blocks used to folio one or more of the potential MOFs. The generation module is further configured to determine which of the potential MOFs that can be formed by combining the building blocks. As used herein, the term "module" or "unit" includes a hardware and/or software system that operates to perform one or more functions. For example, a module or unit may include a computer processor, controller, or other logic-based device that performs operations based on instructions stored on a tangible and non-transitory computer readable storage medium, such as a computer memory. Alternatively, a module or unit may include a hard-wired device that performs operations based on hard-wired logic of the device. The modules and/or units shown in the attached figures may represent the hardware that operates based on software or hardwired instructions, the software that directs hardware to perform the operations, or a combination thereof.

In another aspect, the building blocks include inorganic building blocks, organic building blocks, and functional groups.

In another aspect, the generation module is configured to connect the inorganic building blocks with the organic building blocks.

In another aspect, the generation module is configured to combine the building blocks based on at least one of topological information or geometrical information assigned to the building blocks.

In another aspect, the system also includes an evaluation module configured to calculate one or more material properties of the potential MOFs.

In another aspect, the one or more material properties include one or more of surface area, pore volume, pore size distribution, powder x-ray diffraction pattern, or methane adsorption capability.

In another aspect, the evaluation module is configured to perform an atomistic grand Monte Carlo simulation to calculate at least one of the one or more material properties.

In another embodiment, a method for generating and/or screening one or more potential metal-organic frameworks (MOFs) is provided. The method includes receiving building blocks used to form one or more of the potential MOFs, determining which of the potential MOFs that can be formed by combining the building blocks, and forming the potential MOFs based on the building blocks that can be combined with each other.

In another aspect, the building blocks include inorganic building blocks, organic building blocks, and functional groups.

In another aspect, forming the potential MOFs includes combining the inorganic building blocks with the organic building blocks.

In another aspect, forming the potential MOFs includes combining the building blocks based on at least one of topological information or geometrical information assigned to the building blocks.

In another aspect, the method also includes calculating one or more material properties of the potential MOFs.

In another aspect, the one or more material properties include one or more of surface area, pore volume, pore size distribution, powder x-ray diffraction pattern, or methane adsorption capability.

In another aspect, calculating the one or more material properties includes performing an atomistic grand Monte Carlo simulation to calculate at least one of the one or more material properties.

In another embodiment, a computer readable storage medium for a system having a processor is provided. The computer readable storage medium includes one or more sets of instructions that direct the processor to receive building blocks used to form one or more of the potential MOFs, determine which of the potential MOFs that can be formed by combining the building blocks, and form the potential MOFs based on the building blocks that can be combined with each other.

In another aspect, the computer readable storage medium is a tangible and non-transitory computer readable storage medium.

In another aspect, the building blocks include inorganic building blocks, organic building blocks, and functional groups.

In another aspect, the one or more sets of instructions direct the processor to combine the inorganic building blocks with the organic building blocks.

In another aspect, the one or more sets of instructions direct the processor to combine the building blocks based on at least one of topological information or geometrical information assigned to the building blocks.

In another aspect, the one or more sets of instructions direct the processor to calculate one or more material properties of the potential MOFs.

In another aspect, the one or more material properties include one or more of surface area, pore volume, pore size distribution, powder x-ray diffraction pattern, or methane adsorption capability.

In another aspect, the one or more sets of instructions direct the processor to perform an atomistic grand Monte Carlo simulation to calculate at least one of the one or more material properties.

In another embodiment, a method for producing a metal-organic framework (MOF) is provided. The method includes combining tetramethylbenzene, phenylboronic acid pinacol ester, and dioxane to form an organic body, drying the organic body, mixing the organic body with potassium hydroxide to form a solid body, mixing the solid body with copper nitrate to form a solution, and heating the solution to form a crystalline powder of the MOF.

In another aspect, the tetramethylbenzene is 1,4-diiodo-2,3,5,6-tetramethylbenzene.

In another aspect, the phenylboronic acid pinacol ester is 3,5-bis(methoxycarbonyl) phenylboronic acid pinacol ester.

In another aspect, the method also includes adding dichloromethane with the tetramethylbenzene, the phenylboronic acid pinacol ester, and the dioxane to form the organic body.

In another aspect, the method also includes acidifying the organic body with hydrochloric acid.

In another embodiment, the inventive subject matter described herein can be directed to MOFs, which can be described as polymeric crystalline structures and/or a coordination product of an inorganic metal center block component and one or more organic linker/ligand block components. A metal of the metal center component can be any metal capable of coordinating to one or more linker/ligand components of the sort described herein. MOFs can have solvent molecules coordinated to the metal centers or can be substantially free of solvent. Pore dimension can vary, limited only by choice of metal center and linker/ligand component and/or substituent thereon, together with solvent or other porogen employed or synthetic technique utilized. In various non-limiting embodiments, the pore size of the present MOFs can be up to about 3 Å to about 11 Å or more, and in specific embodiments can be about 4 Å to about 8 Å.

In another aspect, each such linker/ligand component can comprise a plurality of terminal groups for metal center coordination, such groups as can be selected from carboxy (protonated in the acid form, or at least partially unprotonated as a corresponding conjugate base) and corresponding nitrogenous groups (e.g., without limitation, nitrile, pyridyl, pyrazyl, etc., as described below), and combinations thereof, such terminal groups coupled by R, wherein R can be a covalent bond, or moieties of the sort illustrated in FIG. 3 and combinations thereof coupled to one another, such linker/ligand block components as can be optionally substituted with one or more groups of the sort also described in FIG. 3. In the context of an arylene or multicyclo linker/ligand component, such a nitrogenous group can be considered as replacement of a carboxy group with a ring nitrogen center to provide the corresponding heterocyclic moiety. Alternatively, without limitation, in the context of an acetylenic linker/ligand component, such a nitrogenous group can be considered as replacement of a carboxy group with a terminal nitrogen to provide the corresponding nitrile.

In another aspect, the inventive subject matter can comprise compositions of one or more of the present MOFs together with a binder, organic viscosity-enhancing compound, liquid, or combinations thereof.

In one embodiment, a system for generating and/or screening one or more potential metal-organic frameworks (MOFs) is provided. The system includes a generation module that is configured to receive identifications of building blocks for determining if the building blocks can be used to form one or more of the potential MOFs. The generation module is further configured to determine which of the potential MOFs that can be formed by simulating a combining of the building blocks in different arrangements.

In one embodiment, a method for generating and/or screening one or more potential metal-organic frameworks (MOFs) is provided. The method includes receiving building blocks used to form one or more of the potential MOFs, determining which of the potential MOFs that can be formed by simulating a combining of different arrangements of the building blocks, and outputting an identification of the potential MOFs that can be formed from the building blocks based on the simulating of the combining of the building blocks.

In one embodiment, a computer readable storage medium for a system having a processor is provided. The computer readable storage medium includes one or more sets of instructions that are configured to direct the processor to receive an identification of building blocks for one or more of the potential MOFs, determine which of the potential MOFs that can be formed by performing a simulation of combining of the building blocks, and output an identification of the potential MOFs that can be formed from the building blocks based on the building blocks that can be combined with each other in the simulation.

In one embodiment, a metal organic framework (MOF) is provided. The MOF includes a polymeric structure of an inorganic metal center block component; an organic linker block component; and, optionally a solvent, said linker block component comprising a plurality of terminal groups selected from carboxy groups and nitrogenous groups coupled by R, wherein R is selected from a covalent bond and moieties selected from C, arylene moieties, arylene tetracarboxydiimide moieties, fused arylene moieties, fused arylenetetrayl moieties, heteroarylene moieties, di-valent multicyclo moieties, ethynylene moieties and ethenylene moieties and combinations of said moieties coupled one to another.

In one embodiment, a metal organic framework (MOF) includes a polymeric crystalline structure comprising the coordination product of a metal component selected from $Zn_4O$, $Zn_2$, $Cu_2$, $V_3O_3$ and $Zr_6O_6$, an organic ligand component selected from the ligands of FIGS. 3B-C and combinations thereof, and optionally a solvent.

In one embodiment, a metal organic framework (MOF) includes a polymeric crystalline structure of a $Cu_2$ metal component, a ligand component of a formula

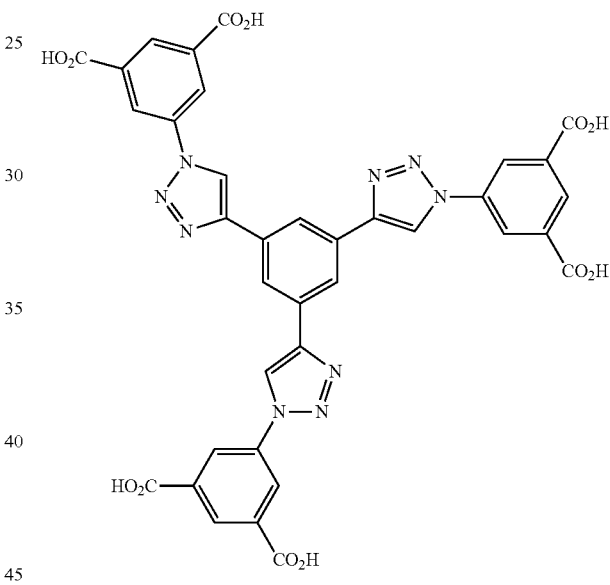

and optionally a solvent.

In one embodiment, a metal organic framework (MOF) includes a polymeric crystalline structure of a $Zn_4O$ metal component, a first ligand component of a formula

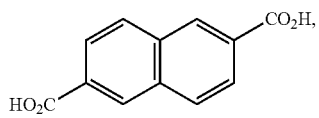

a second ligand component of a formula

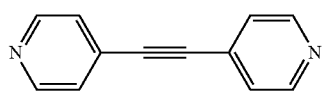

and optionally a solvent.

In one embodiment, a compound of a formula

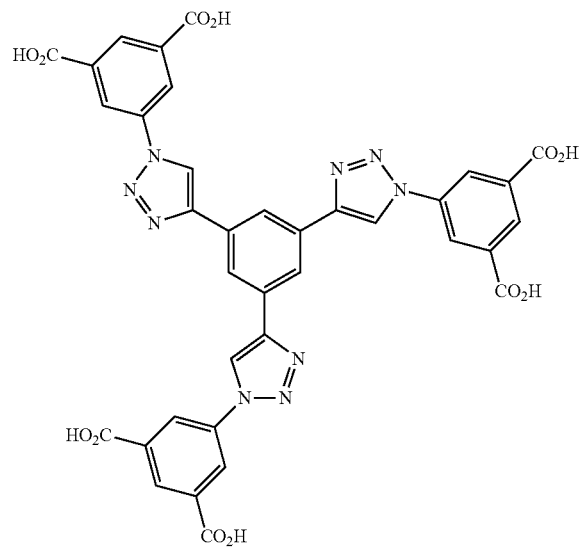 [SMILES: O=C(O)c1cc(C(=O)O)cc(-n2cc(-c3cc(-c4cn(-c5cc(C(=O)O)cc(C(=O)O)c5)nn4)cc(-c4cn(-c5cc(C(=O)O)cc(C(=O)O)c5)nn4)c3)nn2)c1]

and salts thereof is provided.

In one embodiment, a metal organic framework (MOF) building block comprising a compound of a formula

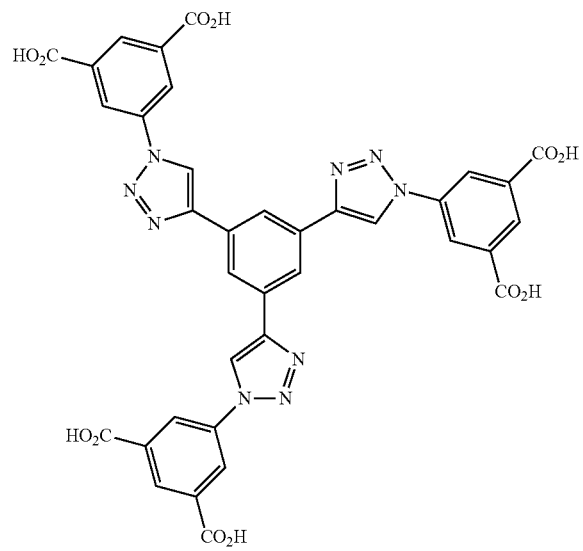 [SMILES: O=C(O)c1cc(C(=O)O)cc(-n2cc(-c3cc(-c4cn(-c5cc(C(=O)O)cc(C(=O)O)c5)nn4)cc(-c4cn(-c5cc(C(=O)O)cc(C(=O)O)c5)nn4)c3)nn2)c1]

and a metal component is provided.

In one embodiment, a method of gas sorption is provided. The method includes providing a metal organic framework (MOF) comprising a polymeric crystalline structure comprising the coordination product of a metal component selected from. $Zn_4O$, $Zn_2$, $Cu_2$, $V_3O_3$ and $Zr_6O_6$, an organic ligand component selected from the ligands of FIGS. 3B-C and combinations thereof, and optionally a solvent. The method also includes contacting said MOF and a gas under at least one of a pressure and a temperature sufficient for gas sorption with said MOF.

In one embodiment, a method of using a metal organic framework (MOF) includes building block comprising a ligand component of a compound of a formula

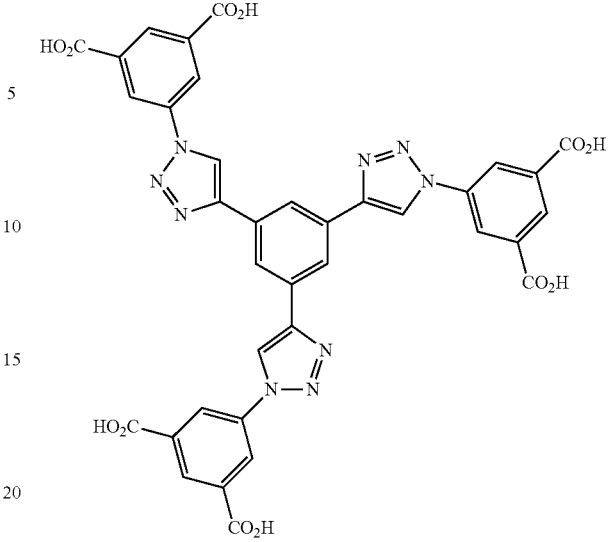

and salts thereof for methane storage. The method includes providing a MOF comprising a building block of a compound of a formula

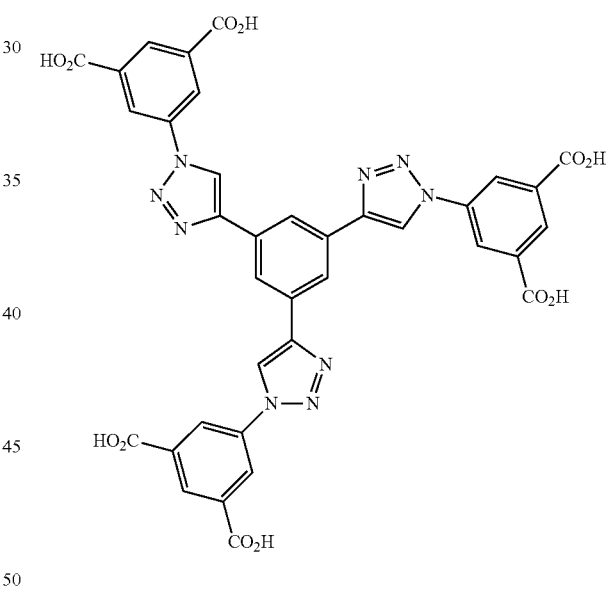

and a metal component, and contacting said MOF and methane under at least one of a pressure and a temperature sufficient for methane storage with said MOF.

In one embodiment, a metal organic framework (MOF) is provided. The MOF comprises a polymeric crystalline structure including the coordination product of a metal component comprising a metal center selected from $Zn_4O$, $Zn_2$, $Cu_2$, $V_3O_3$ and $Zr_6O_6$, an organic ligand component selected from the ligands of FIGS. 3B-C and combinations thereof, and optionally a solvent.

In one embodiment, a metal organic framework (MOF) is provided that includes a polymeric crystalline structure of a $Cu_2$ metal component, a ligand component of a formula

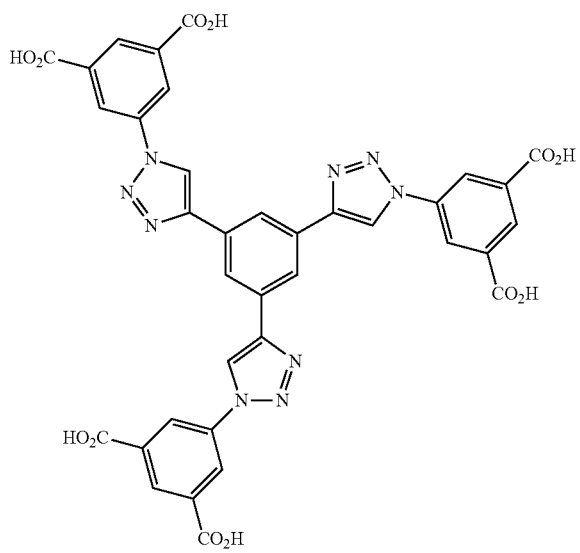 [SMILES: O=C(O)c1cc(C(=O)O)cc(-n2cc(-c3cc(-c4cn(-c5cc(C(=O)O)cc(C(=O)O)c5)nn4)cc(-c4cn(-c5cc(C(=O)O)cc(C(=O)O)c5)nn4)c3)nn2)c1]

and optionally a solvent.

In one embodiment, a metal organic framework (MOF) is provided that includes a polymeric crystalline structure of a $Zn_4O$ metal component, a first ligand component of a formula

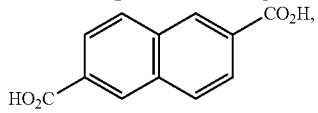

a second ligand component of a formula

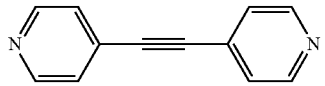 [SMILES: C(#Cc1ccncc1)c1ccncc1]

and optionally a solvent.

In one embodiment, a compound of a formula

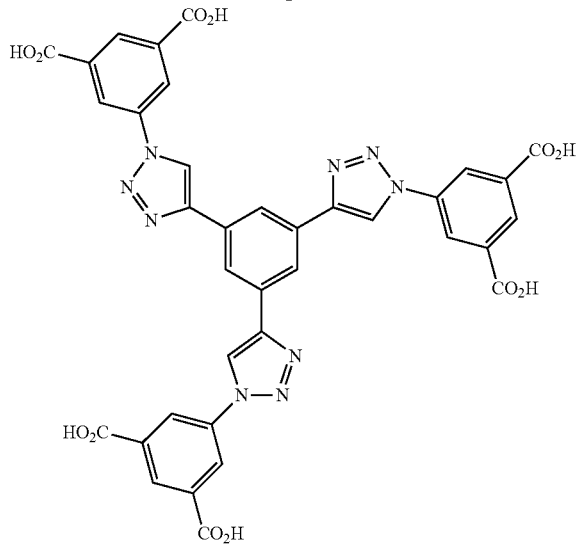

and salts thereof is provided.

In one embodiment, a metal organic framework (MOF) building block is provided that includes a compound of a formula and a metal component.

In one embodiment, a method of gas sorption is provided. The method includes providing a metal organic framework (MOF) that includes a polymeric crystalline structure comprising the coordination product of a metal component comprising a metal center selected from $Zn_4O$, $Zn_2$, $Cu_2$, $V_3O_3$ and $Zr_6O_6$, an organic ligand component selected from the ligands of FIGS. 3B-C and combinations thereof, and optionally a solvent. The method also includes contacting said MOF and a gas under at least one of a pressure and a temperature sufficient for gas sorption with said MOF.

In one embodiment, a method of using a metal organic framework (MOF) building block comprising a ligand component of a formula

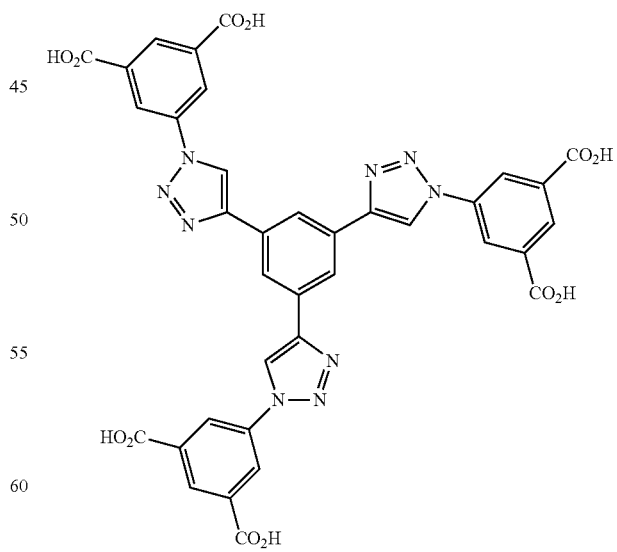

and salts thereof for methane storage. The method includes providing a MOF comprising a building block that includes a compound of a formula

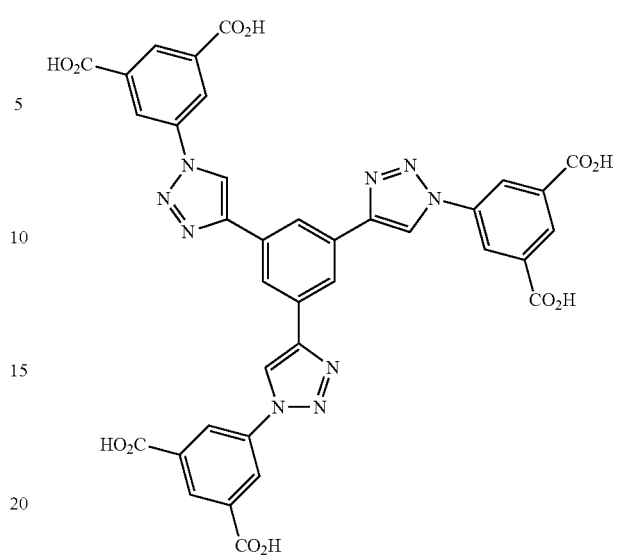

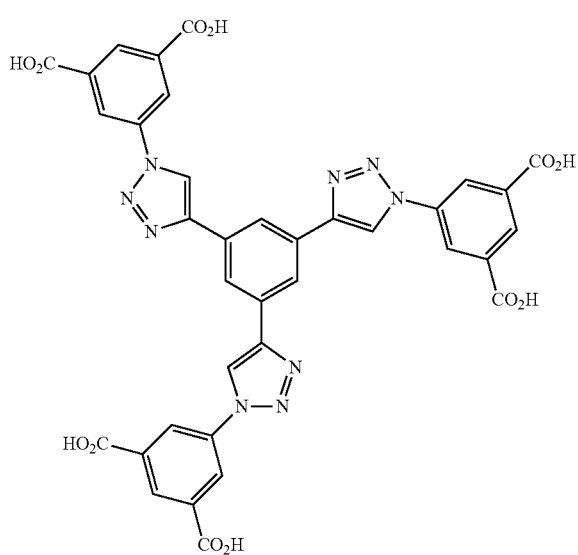 [SMILES: O=C(O)c1cc(C(=O)O)cc(-n2cc(-c3cc(-c4cn(-c5cc(C(=O)O)cc(C(=O)O)c5)nn4)cc(-c4cn(-c5cc(C(=O)O)cc(C(=O)O)c5)nn4)c3)nn2)c1]

and a metal component; and contacting said MOF and methane under at least one of a pressure and a temperature sufficient for methane storage with said MOF.

In one embodiment, a container for at least one of uptaking, storing and releasing at least one gas is provided. The container includes at least one of an inlet component and an outlet component; a pressure control component to maintain a gas under pressure in said container; and a metal organic framework material comprising a metal organic framework (MOF) that includes a polymeric crystalline structure comprising the coordination product of a metal component comprising a metal center selected from $Zn_4O$, $Zn_2$, $Cu_2$, $V_3O_3$ and $Zr_6O_6$, an organic ligand component selected from the ligands of FIGS. 3B-C and combinations thereof, and optionally a solvent, and optionally a gas.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The subject matter described herein will be better understood from reading the following description of non-limiting embodiments, with reference to the attached drawings, wherein below.

DETAILED DESCRIPTION

Figure 1:
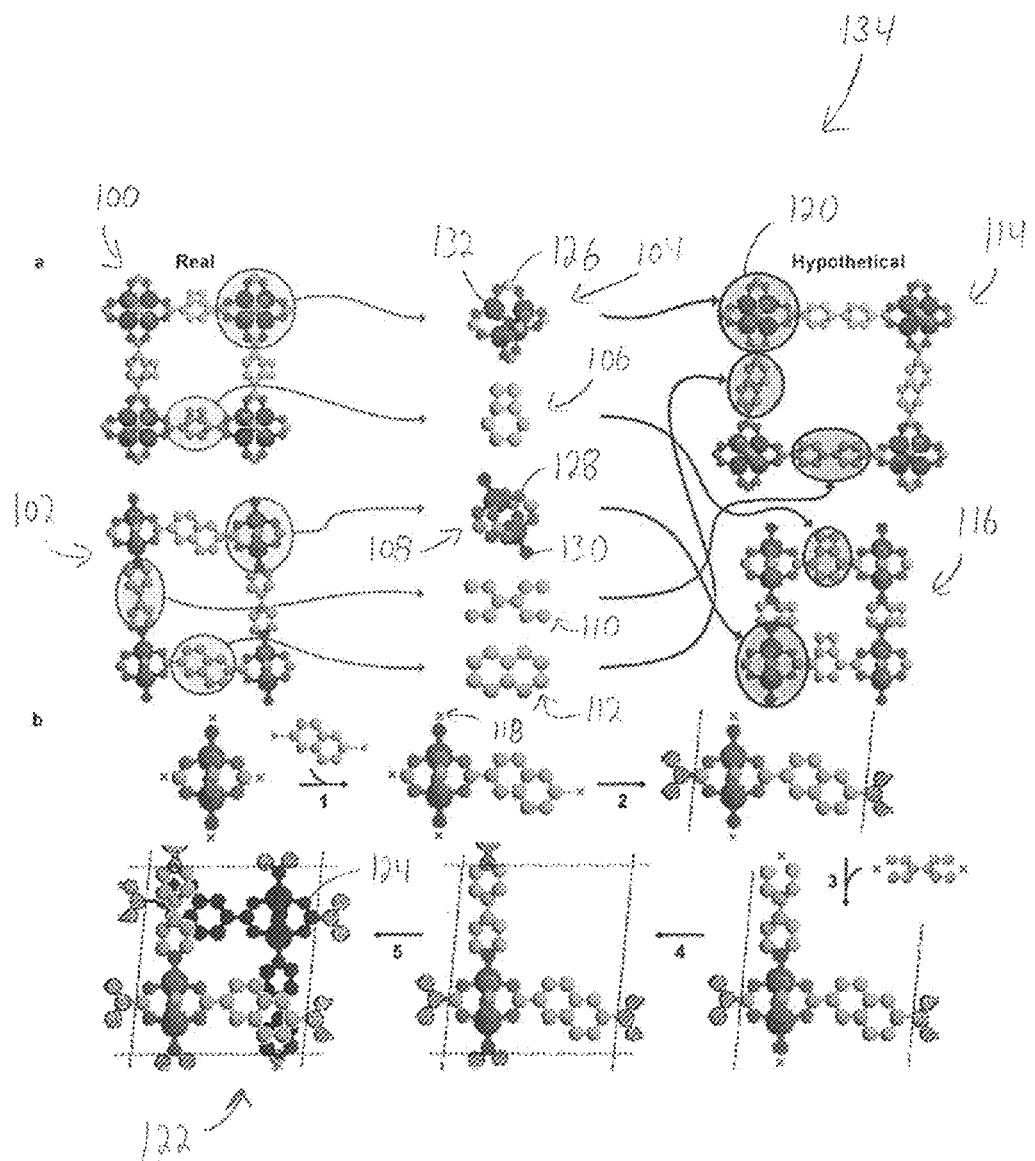
FIG. 1 is a schematic diagram that provides a visual summary of one embodiment of a hypothetical MOF generation strategy.

FIG. 1 is a schematic diagram that provides a visual summary of one embodiment of a hypothetical MOF generation strategy or process 134. With respect to FIG. 1, black circles or spheres 124 represent atoms belonging to one of two interpenetrated frameworks. Grey spheres 126, red spheres 128, blue spheres 130, and turquoise spheres 132 represent carbon, oxygen, nitrogen, and zinc atoms, respectively. However, other atoms may be included or used. Hydrogen atoms have been omitted from FIG. 1 for clarity.

Crystal structures of existing MOFs 100, 102 can be obtained from x-ray diffraction data and be divided into building blocks 104, 106, 108, 110, 112. The building blocks represent subsets or portions of the MOFs 100, 102. Alternatively, a building block can represent an entire MOF (e.g., where an entire MOF is combined with one or more additional building blocks or other MOFs to form a new potential MOF). The building blocks 104, 106, 108, 110, 112 can be computationally combined (e.g., by the system 1700 shown in FIG. 17) to form new, hypothetical MOFs 114, 116. The recombination process may occur by stepwise addition of the building blocks 104, 106, 108, 110, 112, which may be attached at their connection sites 118 (e.g., the X's in FIG. 1). The building blocks 104, 106, 108, 110, 112 may also be connected across periodic boundaries 120 (e.g., shown as hashed circles that indicate mirror images in FIG. 1). The process shown in FIG. 1 may repeat until all connection sites 118 or at least a predetermined fraction of the connection sites 118 is utilized. An interpenetrated MOF 122 may be generated if enough space exists.

In accordance with one embodiment, and as described in more detail below, a MOF generation procedure creates hypothetical MOFs by recombining building blocks derived from crystallographic data of previously synthesized MOFs. Atoms can be grouped into building blocks based on reagents used in the actual synthesis. A building block can combine with one or more other (e.g., different) building blocks provided that the geometry and chemical composition local to the point of connection between the building blocks is the same as or similar to in crystallographically determined structures. Building blocks may be combined stepwise, and when a collision occurs at particular step, a different building block may be chosen or a different connection site may be used, until all or at least a predetermined fraction of the possibilities are exhausted. While the total number of steps in each generation process can vary, there may be at least three steps when, instead of adding a building block, a periodic boundary is imposed by connecting any two building blocks (e.g., steps 2 and 4 in FIG. 1). When no more building blocks can be added, the crystal generation procedure may be complete. Note that no force field (or quantum mechanical) energy minimizations may be involved in one embodiment. Instead, the pieces may be connected according to the geometric rules that govern how the building blocks are connected in existing MOFs.

Figure 2:
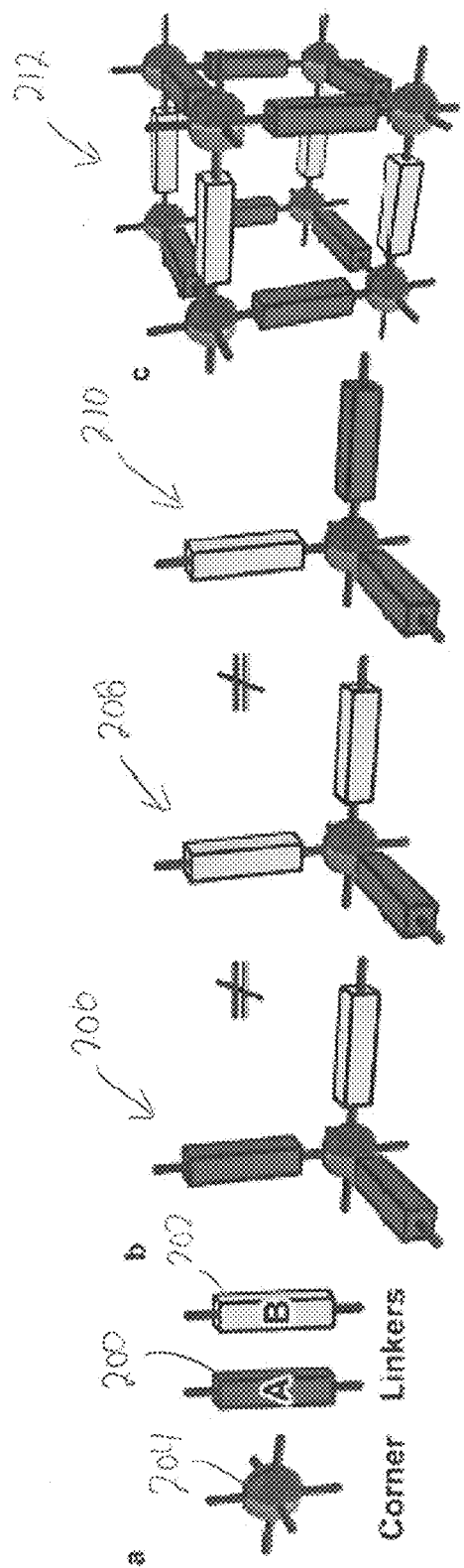
FIG. 2 is a schematic diagram of components of a hypothetical MOF in accordance with one embodiment.

FIG. 2 is a schematic diagram of components of a hypothetical MOF in accordance with one embodiment. Estimates on the number of possible hypothetical MOFs for a given library or corpus of modular building blocks can be obtained for hypothetical MOFs of no more than a finite or designated size (from here on assumed to be 100 building blocks or less, although a different number may be used) and by applying several simplifying assumptions. The system 1700 shown in FIG. 17 may be used to determine the hypothetical MOFs. First, consider the case of MOFs composed of only one type of inorganic building block and one type of organic building block. Let L be the number of organic building blocks (L as in "linkers") and C be the number of inorganic building blocks from which to choose (C as in "corners"). Linkers 200, 202 may connect with corners 204, and vice-versa. For example, linkers 200, 202 may not directly connect with each other and/or corners 204 may not directly connect with each other in one embodiment. The number of possible MOFs, N, may be represented as N=L×C, which corresponds, for example, to 900 for L=90 (e.g., 90 linkers 200, 202) and C=10 (e.g., 10 corners 204).

Now consider the case where a unit-cell of a MOF contains M linkers (not to be confused with L: the number of linker types), which can be either of two types: A or B. Here the diversity of possible structures spans two dimensions: the ratio of A-linkers to B-linkers, and the number of possible arrangements of A and B linkers at a fixed ratio.

As shown in FIG. 2, MOFs that include two distinct linkers (A-type, represented by 200, and B-type, represented by 202) may vary in the ratio of A to B linkers (e.g, MOF 206 versus MOF 208) or in the arrangement of those linkers at a fixed ratio (e.g., MOF 206 versus MOF 210). A larger fragment of a schematic MOF framework 212 is shown in FIG. 2 for clarity.

A lower bound on the number of unique crystals can be estimated by the number of ratios of component types (e.g., a unit-cell with two A-linkers 200 and one B-linker 202 may not be the same crystal as one with one A-linker 200 and two B-linkers 202). Calculating this lower bound can be similar to finding the number of unordered sets of M linkers of L linker types (the answer is: M+L−1 choose L−1). However, two crystals, both with two A-linkers 200 and one B-linker 202 but in different positions, can either be physically identical (e.g., related by a symmetry operation) or unique (for example, if the corner is asymmetrical as in FIG. 2). An upper bound on the number of possible crystals can be established by forming strings such as "BBA", "BAA", "BAB", and so forth. Thus, with a library of one corner 204 and two linkers 200, 202, the number, N of possible MOFs may be represented as follows:

$$\binom{M+L-1}{L-1} = \binom{3+2-1}{2-1} < N < 2^3 \quad \text{(Eqn. 1)}$$
$$= L^M$$

$$4 < N < 8 \quad \text{(Eqn. 2)}$$

If more corners 204 and linkers 200, 202 are included in the library (for example, C=10, L=90), but the constraint that MOFs may only use two linkers 200, 202 simultaneously is maintained, then a modified expression may be derived for the number N of possible MOFs:

$$C \times L \times \left[\binom{L-1}{2}\binom{3+2-1}{2-1} - L + 2\right] < N < C \times \quad \text{(Eqn. 3)}$$
$$L \times \left[\binom{L-1}{2}2^3 - L + 2\right]$$

$$81{,}000 < N < 241{,}200 \quad \text{(Eqn. 4)}$$

Finally, when it is considered that the linkers 200, 202 may be made from modular organic components, the number of hypothetical MOFs can increase considerably. A linker 200, 202 can be defined as a combination of a backbone (e.g., benzene-1,4-dicarboxylic acid) and a functional group (e.g., methyl). Let B and F represent the number of backbones and functional groups in the library, respectively. In general, a single choice of backbone and functional group may result in many possible linkers 200, 202, due to the number of ways the functional group may be arranged on the backbone (e.g., meta-, para-, and ortho-xylene) or simply due to the total number of functional groups (e.g., toluene vs. xylene). If it is conservatively estimated that every backbone has a limited number of possible arrangements for any given choice of functional group (e.g., two), then the number of linkers, L, can be given by:

$$L = B \times F \times 2 \quad \text{(Eqn. 5)}$$

Substituting Equation 5 into Equation 3, and assuming a library of 10 corners, 10 functional groups, and 80 backbones (100 building blocks total), the number of potential MOFs corresponds to a lower bound of 25,600,000 and an upper bound of 89,560,000. Note that all building blocks in this library are assumed to be chemically compatible so that every piece is interchangeable (which may be a reasonable assumption for an appropriately chosen chemical library). Alternatively, one or more constraints may be implemented to reduce the number of potential MOFs, such as by restricting one or more building blocks from being used with one or more other building blocks.

In one embodiment of the MOF generation procedure described herein, a library of 5 corners, 42 backbones, and 13 functional groups can be used, although not all of the corners, backbones, and/or functional groups may be chemically and/or geometrically compatible. If it were the case that all corners in the library could combine with all linkers (and all backbones with all functional groups, which may not be possible with all building blocks, such as building block 10 in FIG. 3), between ~5.9 and ~20.9 million entries can be expected in a database of potential MOFs, rather than approximately 137,000.

Figure 3A:
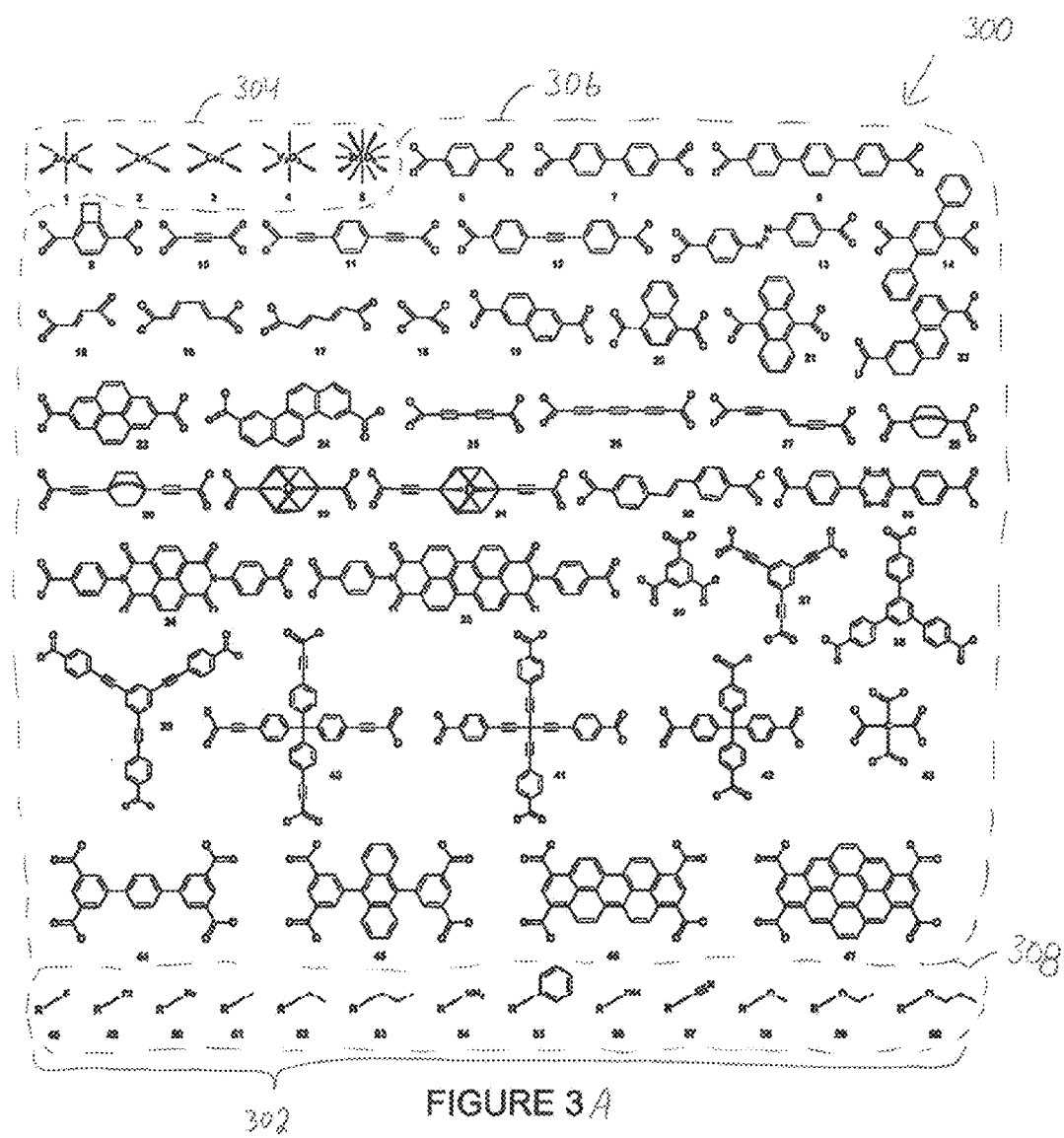
FIGS. 3A and 4 provide diagrams of a library of several building blocks that may be used to generate a database for hypothetical MOFs in accordance with one embodiment.
Figure 3B:
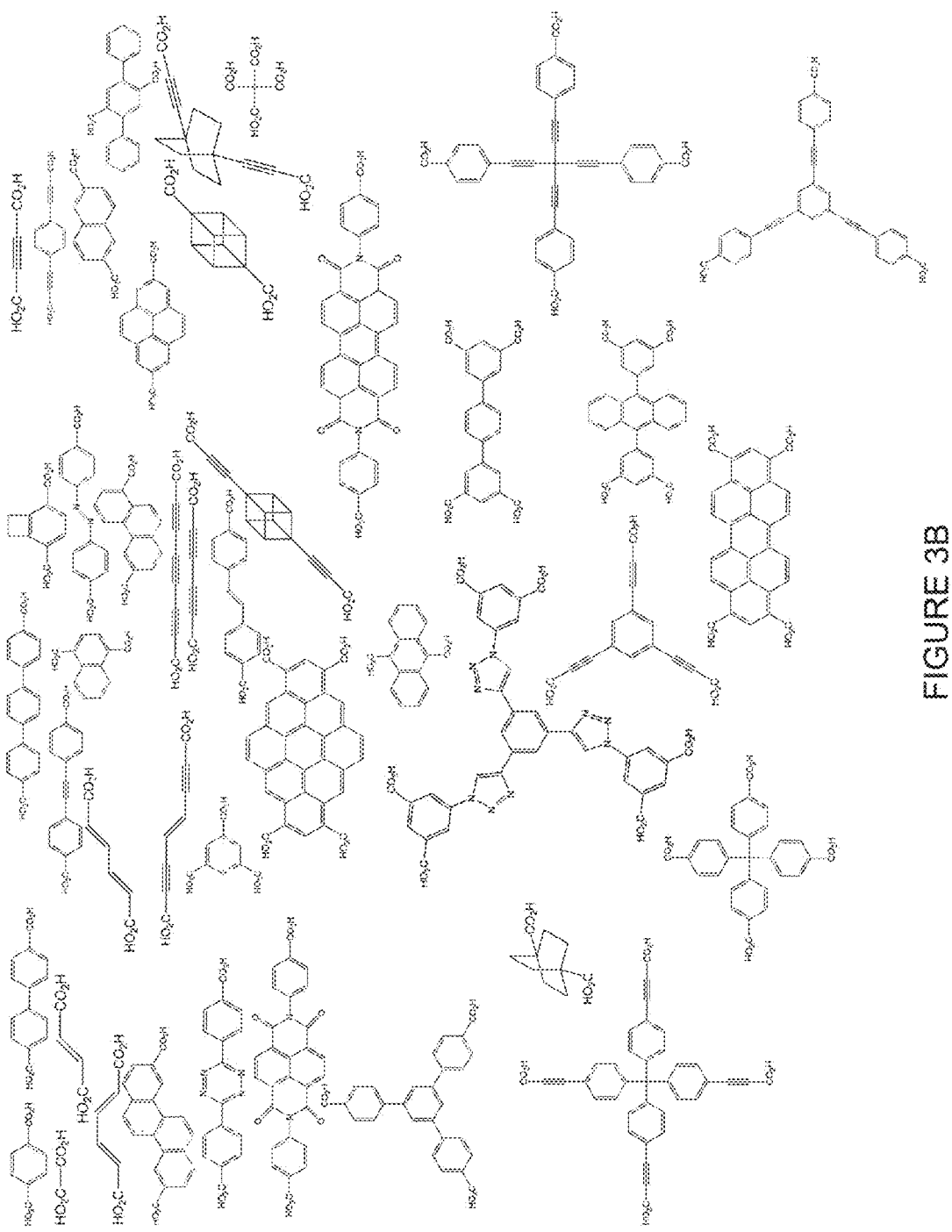
FIGS. 3B and 3C provide, respectively, non-limiting carboxy-terminated and analogous nitrogen-terminated linker/ligand components corresponding to the carboxylate building block components of FIG. 3A, as can be used in the generation and synthesis of one or more metal organic frameworks of the inventive subject matter.
Figure 3C:
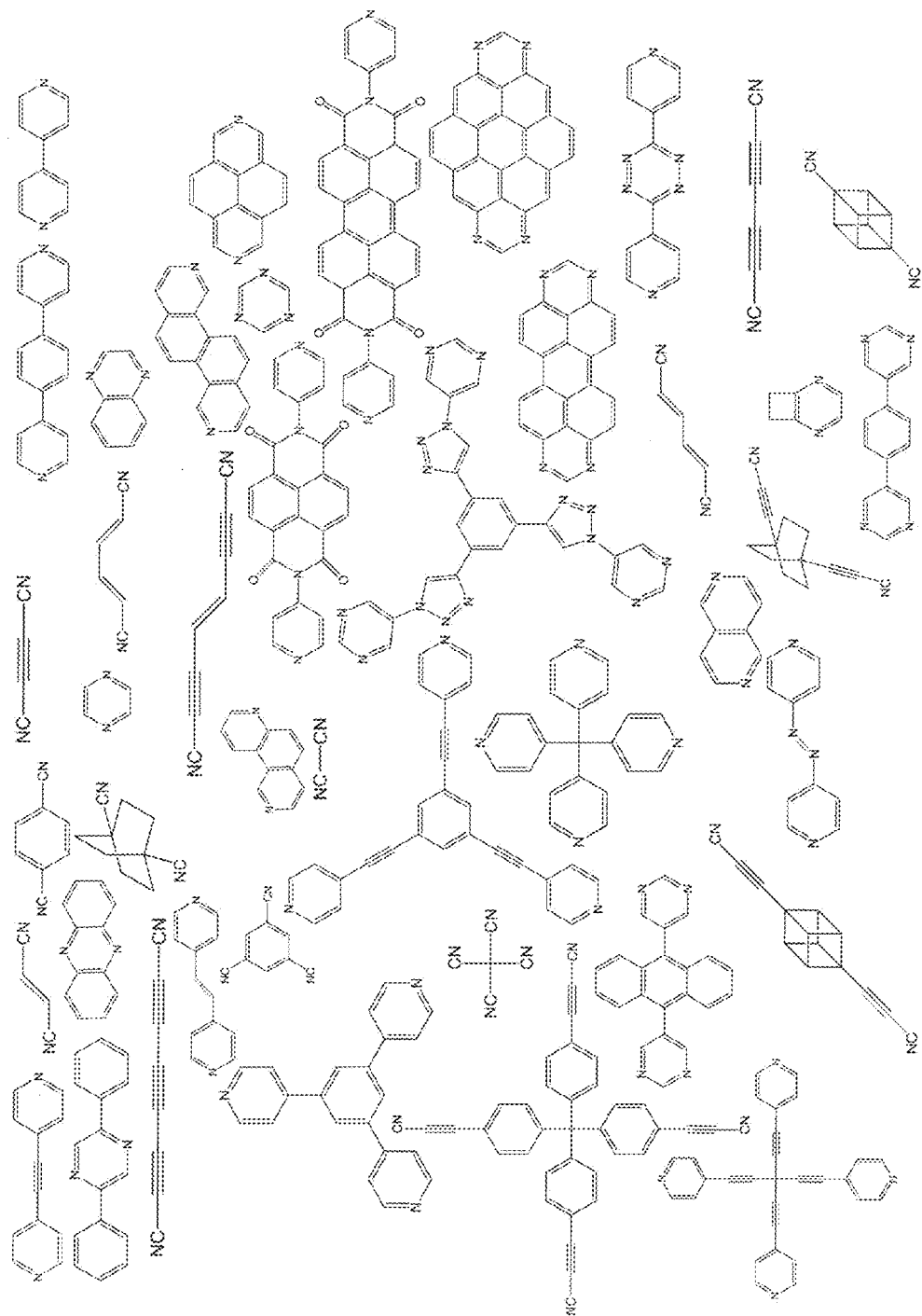

FIGS. 3A-C provide diagrams of a library 302 of several building blocks 300 that may be used to generate a database for hypothetical MOFs in accordance with one embodiment. The library 302 shown in FIG. 3 includes sixty building blocks 300, but alternatively may include a smaller or larger number of building blocks 300. The building blocks shown in FIG. 3 (including the nitrogen-terminated organic analogs; see FIG. 4) may be used to generate the database of approximately 137,000 hypothetical MOFs that are described above. The building blocks 300 numbered 1 through 5 are inorganic building blocks 304, the building blocks 300 numbered 6 through 47 are organic building blocks 306, and the building blocks 300 numbered 48 through 60 are functional groups 308. The inorganic building blocks 304 numbered 2 and 3 (referred to sometimes as paddlewheels) are able to coordinate to nitrogen containing compounds (e.g., pyrazine). Not shown then, in FIG. 3, are one or more of the analogous building blocks terminated by nitrogen atoms instead of carboxylic acid groups.

Figure 4:
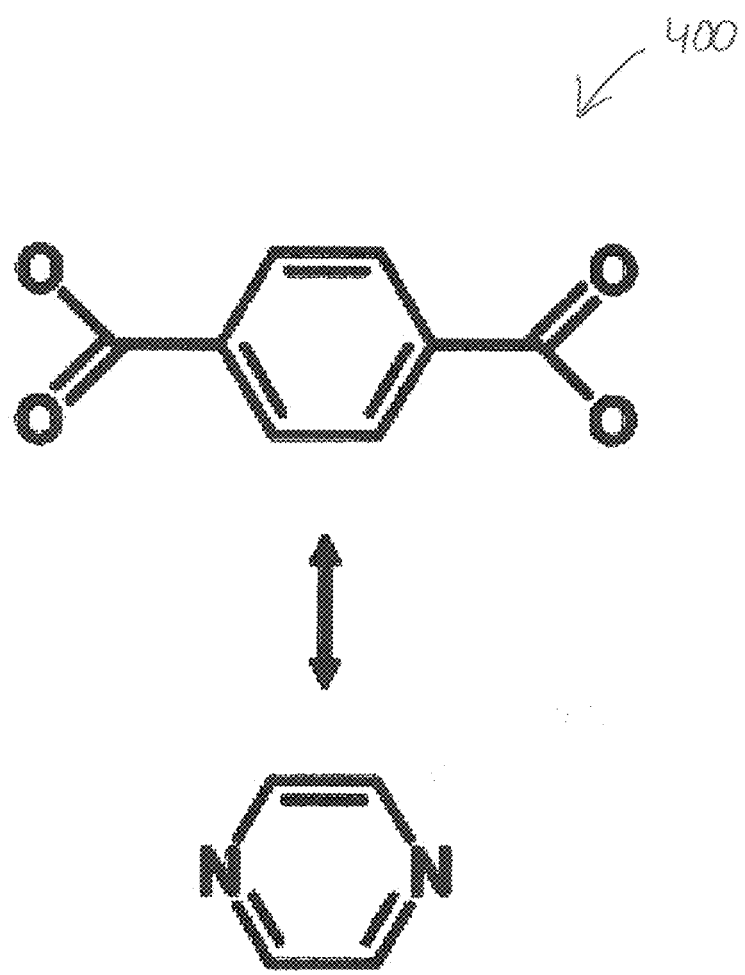

The building blocks 300 shown in FIG. 3 are shown with terminal carboxylate groups. In one embodiment, however, one or more of the building blocks 300 may also exist with a nitrogen terminated group, as well, for coordinating to paddlewheels 400, as shown in FIG. 4.

Figure 5:
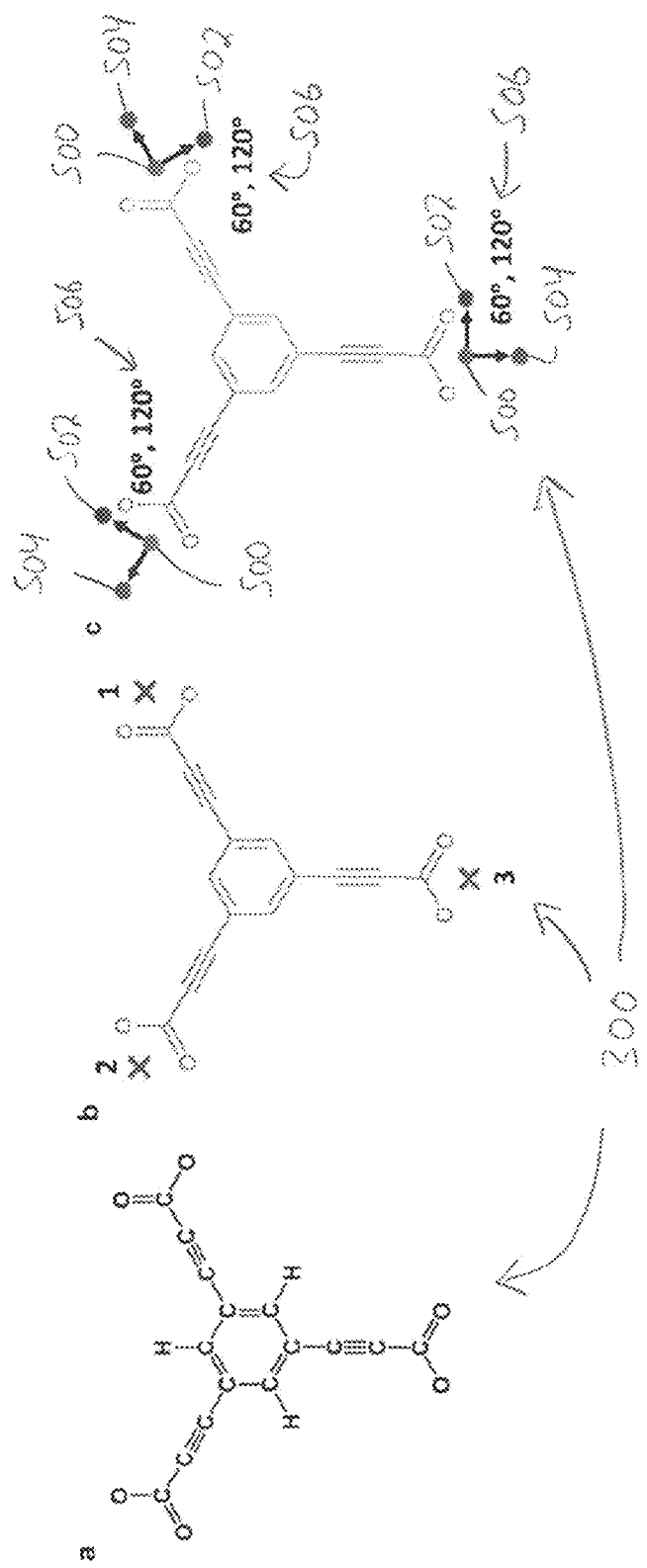
FIG. 5 illustrates examples of such topological information and geometrical information.

In order to recombine building blocks 300 into crystals, additional topological and geometrical information may be assigned to one or more of the building blocks 300 by a system 1700 shown and described below in connection with FIG. 17. FIG. 5 illustrates examples of such topological information and geometrical information. While FIG. 5 provides some examples, other types of information, and/or other types of topological and/or geometrical information that may be assigned to the building blocks by the system 1700. As shown in FIG. 5, encoded in the building blocks 300 in a database or other memory structure of the system 1700 may be the (a) atom composition and geometry, (b) topological information via numbered connection sites, and (c) geometrical information via pseudo-atoms (schematically shown as red dots 500, green dots 502, and blue dots 504 representative of R, G, and B pseudo atoms, respectively) and lists of angles 506 for alternative orientations.

The topological information may take the form of numbered connection sites so that a MOF generation algorithm used by the system 1700 (shown in FIG. 17) to generate the potential MOFs can interpret instructions such as "connect building block 2, site 3, to building block 10, site 1." Additionally, this information can be used as part of a termination criteria used by the system 1700 to determine when construction of a MOF is complete; such as by determining that a single MOF generation is complete when every connection site or at least a predetermined number or fraction of the connection sites has been connected. In one embodiment, the geometrical information takes the form of three "pseudoatoms" 500, 502, 504 and a list of angles 506 for every connection site (or at least a designated number of connection sites) in the building block 300. The pseudo-atoms 500, 502, 504 each possess a coordinate in 3d space, as well as a label (here referred to arbitrarily as red, green, or blue dots 500, 502, 504, or red, green, or blue dots R, G, or B. One purpose of the pseudoatoms 500, 502, 504 is to specify the relative orientation of two connected building blocks 300. For example, given two connection sites X and Y and their corresponding pseudo-atoms RX, GX, BX, and RY, GY, BY (where R represents the pseudo atoms of the first dots 500, G represents the pseudo atoms of the second dots 502, and B represents the pseudo atoms of the third dots 504), the building blocks 300 may be oriented correctly when the coordinates of RX equal RY, the coordinates of GX equal GY, and the vector RXBX is anti-parallel to the vector RYBY. Finally, if there are multiple "correct" orientations (for example, phenyl rings in a linear chain experience multiple energy minima of equal depth as a function of their relative orientations along the chain axis), the list of angles can specify alternate orientations, which may be equivalent to rotating the pseudoatoms about the RB axis by the specified angle.

Figure 17:
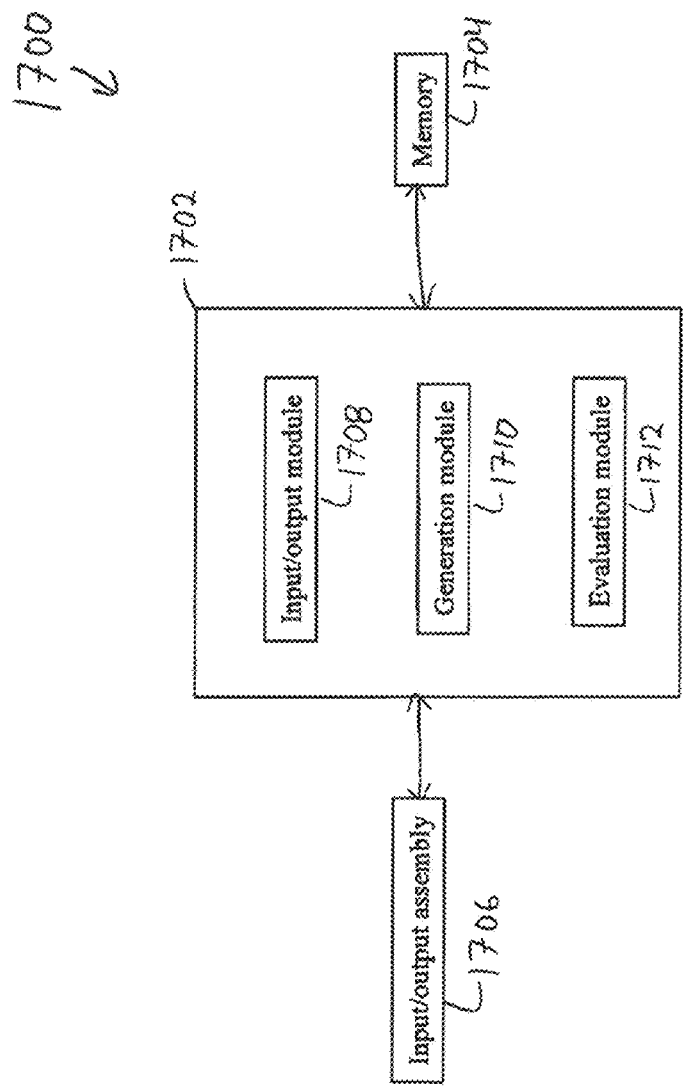
FIG. 17 is a schematic diagram of one embodiment of a system for generating potential metal-organic frameworks (MOFs)

The system 1700 shown in FIG. 17 can determine a variety of possible combinations of building blocks 300 in a variety of possible arrangements to identify potential MOFs. This can be possible because the building blocks may be numbered or otherwise separately identified in a database or other memory structure of the system 1700, and also because a variety of possible arrangements of building blocks 300 can be written or stored as enumerable strings in the database or other memory structure of the system 1700. For example, the string "1, 2-3-1-2-3" as stored in the system 1700 can mean:

"$\underline{1}$, 2-3-1-2-3"→place a building block of type 1 anywhere
"1, 2-$\underline{3}$-1-2-3"→select a building block of type 2 (not yet placed anywhere)
"1, 2-3-$\underline{1}$-2-3"→select its connection site 3
"1, 2-3-$\underline{1}$-2-3"→connect the selected building block to the $1^{st}$ building block placed
"1, 2-3-1-$\underline{2}$-3"→connect the selected connection site to the $2^{nd}$ connection site on the $1^{st}$ building block
"1, 2-3-1-2-$\underline{3}$"→rotate the selected building block using the $3^{rd}$ angle listed at the selected connection site This arrangement can lead to a nonsensical connection of two inorganic building blocks, and so the system 1700 may skip to the next arrangement, namely, "1, 2-3-1-2-4", and so-forth. One embodiment of the generation procedure is summarized in FIG. 6.

Figure 6:
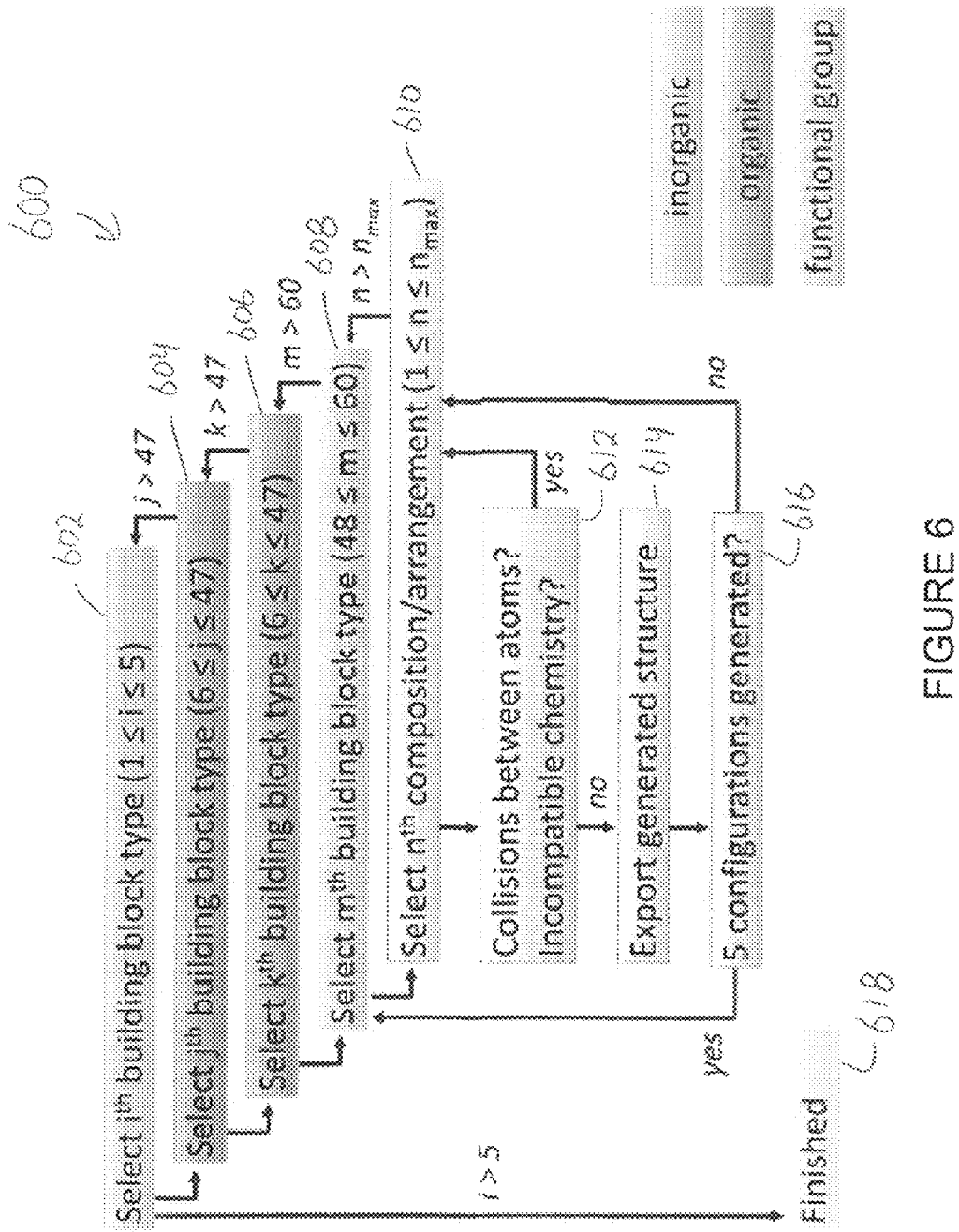
FIG. 6 illustrates a flowchart of a method for generating a hypothetical MOF in accordance with one embodiment.

FIG. 6 illustrates a flowchart of a method 600 for generating a hypothetical MOF in accordance with one embodiment. The method 600 can be implemented by the system 1700 shown in FIG. 17 to create a database of potential MOFs. The method 600 depicts how hypothetical MOFs can be enumeratively generated from a library of building blocks. At 602, 604, 606, and 608, various types of building blocks are selected for use in constructing potential MOFs. The upper and lower limits of i, j, k, and in can refer to the numbered building blocks in FIG. 3. The $i^{th}$ and $j^{th}$ building block types may be inorganic building blocks, and the $m^{th}$ building block type may be a functional group building block. At 610, a total number and arrangement of building blocks is encoded in an enumerable string. In one embodiment of a library of building blocks, functional groups could be connected in a variety of locations where a hydrogen atom is otherwise bonded to a carbon atom, provided no atomic collisions occur. At 612, a collision and/or incompatible chemistry between building blocks may be identified if any two atoms of the building blocks were closer than one angstrom apart in one embodiment. This distance was used so as not to discard potentially interesting MOFs due slight structural errors introduced in the generation process. Alternatively, another distance threshold other than one angstrom is used. If such a collision or incompatible chemistry is identified at 612, the potential MOF that is attempted to be formed by the colliding or incompatible building blocks may be discarded. Flow of the method 600 may return to 610, where the next building block is attempted to be combined and/or another potential MOF is constructed.

If no such collision or incompatible chemistry is identified, then flow of the method 600 may proceed to 614, where the potential MOF formed by the building blocks is exported, such as by storing the potential MOF in a memory of the system 1700, outputting (e.g., displaying, printing, or otherwise communicating) the potential MOF to a user of the system 1700, or the like.

In the above example, if "1, 2-3-1-2-3" was the nth arrangement, then "1, 2-3-1-2-4" could be called the $(n+1)^{th}$ arrangement. The number of possible arrangements for a set of a building blocks may be referred to as nmax. At 616, in one embodiment of a screening procedure used to generate the hypothetical MOFs, if no logical MOF structure could be generated (e.g., a potential MOF that satisfies the criteria at 612 such that the method 600 proceeds from 612 to 614) in the first 64,000 arrangements (or other number of arrangements) of the chosen building blocks, then the arrangement string was incremented by a large random value (e.g., "1, 2-3-1-2-4" might jump to "4, 1-3-2-4-4"). If no MOF structure could be found after 5 such increments (or another number of increments), then the next set of building blocks was chosen (see FIG. 6) in an attempt to build another, different potential MOF. As shown in FIG. 6, if no potential MOF is identified after the designated number of increments, then flow of the method 600 can return to 608, where another m type building block is selected in an attempt to build another potential MOF. Alternatively, if a potential MOF is identified within the designated number of increments, then flow of the method 600 may return to 610, where another compositional arrangement of building blocks is formed in an attempt to identify an additional potential MOF. In one embodiment, the method 600 may sequentially or randomly proceed through the different $i^{th}$, $j^{th}$, $k^{th}$, and/or $m^{th}$ building block types until all or a designated number of potential combinations of building blocks are examined as potential MOFs, as shown in FIG. 6. Once all or at least the designated number of combinations are examined, the method 600 may proceed to 618.

Hypothetical MOF structures generated in accordance with one embodiment can be investigated by comparing coordinates of the atoms in the MOF structures against the coordinates of the atoms in the experimental and energetically optimized structures. If the unit cell dimensions of two structures differed even only slightly, however, then the distance between corresponding atoms in either structure may eventually diverge. For at least this reason, fragments of crystals that shared one atom (chosen arbitrarily) identically at the origin may be compared. These fragments were superimposed using the feature by the same name in a software application or program such as Materials Studio provided by Accelrys. Fragments were defined by selecting a metal atom center and a variety of atoms that could be reached from the metal atom by traversing 7 bonds (an alternative approach would have been to include atoms within a specified radius of a chosen atom center, but this does not guarantee that each fragment has the same total number of atoms). The program orients and translates one fragment relative to the other such that the interatomic distances between the atoms of both fragments are reduced below a threshold or minimized. The degree to which one fragment matches the other is measured by the average root-mean-squared distance over all pairs of nearest atoms in one embodiment. Hydrogen atoms can be ignored as the hydrogen atoms are often missing from crystallographic data. Average differences in atomic positions were less than approximately 0.1 angstrom except in the case of the optimized PCN-14, although even in this case the methane adsorption isotherm may not be greatly affected (see FIG. 9 and accompanying discussion).

Table 1 below provides comparisons of generated versus empirical structures by matching interatomic distances. The table below shows average root-mean-squared distance between matched atoms.

TABLE 1

|  | Experimental vs. Pseudo | Experimental vs. Pseudo-Optimized | Fragment Size (# of atoms) |
| --- | --- | --- | --- |
| HKUST-1 | <0.001 Å | 0.004 Å | 74 |
| IRMOF-1 | 0.013 Å | 0.032 Å | 77 |
| PCN-14 | 0.113 Å | 0.696 Å | 74 |
| MIL-47 | 0.028 Å | 0.089 Å | 131 |

In one embodiment, these geometry optimizations were performed with the Forcite module of Materials Studio using an algorithm which is a cascade of the steepest descent, adjusted basis set Newton-Raphson, and quasi-Newton methods. The bonded and the short range (van der Waals) non-bonded interactions between the atoms were modeled using the Universal Force Field (UFF). In this force field, bond stretching can be described by a harmonic term, angle bending by a three-term Fourier cosine expansion, torsions and inversions by cosine-Fourier expansion terms, and the van der Waals interactions by the Lennard-Jones potential.

In one embodiment, there may be three primary concerns when generating hypothetical crystal structures: Are the structures in an energetic minimum or at a reduced energy? Do generated hypothetical structures agree with experimentally measured structures? How sensitive are predicted physical properties to structural inaccuracies? In order to address these concerns, a set of generated MOF structures can be compared to energetically relaxed counterparts of these MOF structures via force field relaxations or minimizations and also to experimentally measured MOF structures. The influence of the structural differences on predicted properties can be considered, such as the influence in methane adsorption by the structures.

By choosing the appropriate building blocks, crystal structures that resembled the MOFs HKUST-1 (e.g., from Chui et al., A chemically functionalizable nanoporous material [Cu$_3$(TMA)$_2$(H$_2$O)$_3$]n, *Science* 283, 1148-1150 (1999)), IRMOF-1 (e.g., from Li et al., Design and synthesis of an exceptionally stable and highly porous metal-organic framework, *Nature* 402, 276-279 (1999)), PCN-14 (e.g., from Ma et al., Metal-organic framework from an anthracene derivative containing nanoscopic cages exhibiting high methane uptake, *J. Am. Chem. Soc.* 130, 1012-1016 (2008)), and MIL-47 (e.g., from Barthelet et al., A breathing hybrid organic-inorganic solid with very large pores and high magnetic characteristics, *Angew. Chem. Int. Ed.* 41, 281-284 (2002)). These MOFs may significantly differ in their pore topology and chemical composition. The generated structures are referred to as pseudo-HKUST-1, pseudo-IRMOF-1, pseudo-PCN-14, and pseudo-MIL-47 to indicate that, albeit not hypothetical, they are nonetheless not identical to empirical structures. These pseudo-MOFs are then allowed to relax their structures energetically via the UFF implemented in the Forcite module in the Materials Studio software application, as described above. In both the relaxed and non-relaxed versions, superimposing the empirical and generated structures show that the atoms match very closely, with every atom in the pseudo-MOFs shifted from its measured position typically by an average of less than approximately 0.1 angstroms.

Figure 9:
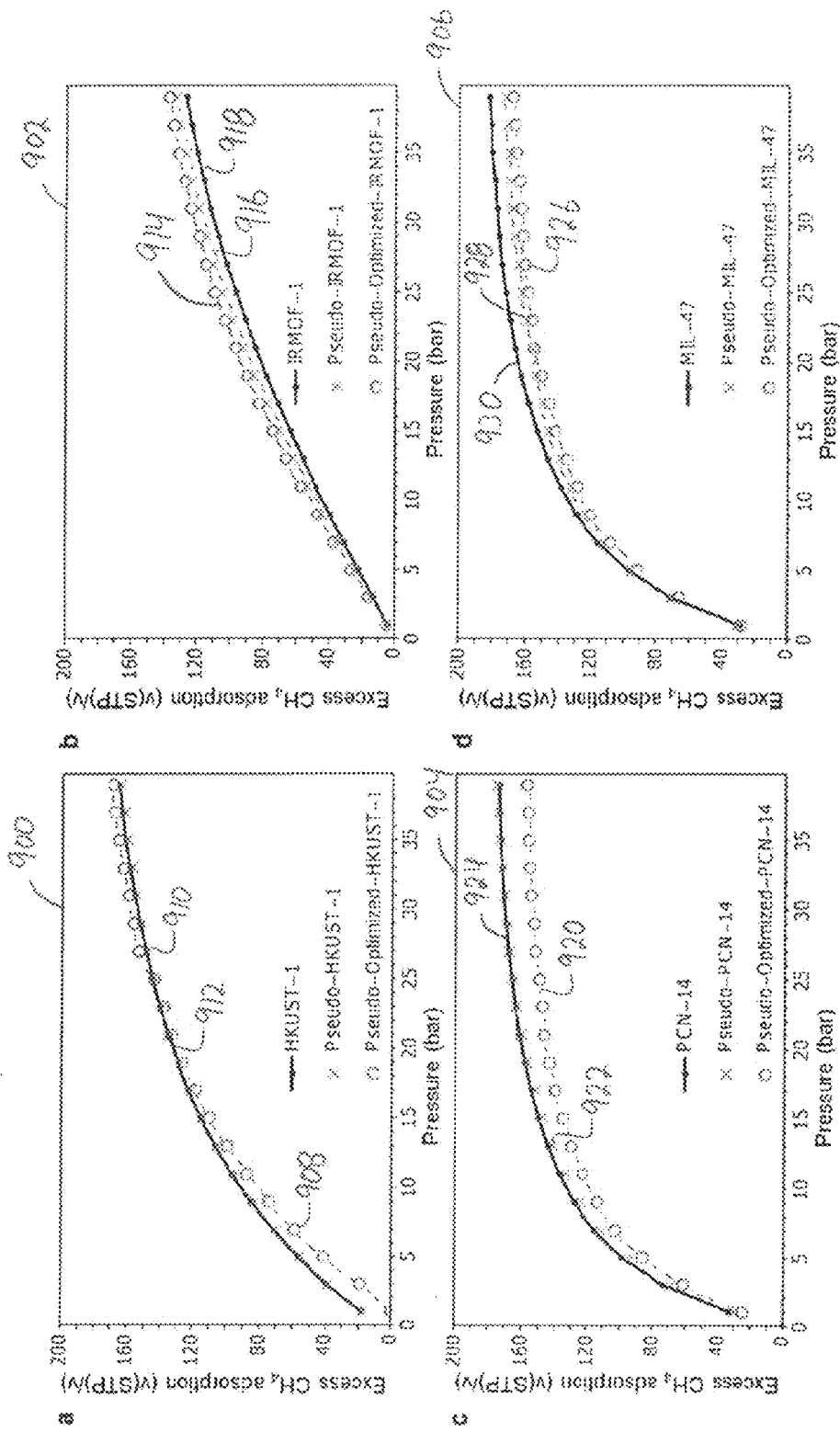
FIG. 9 illustrates comparisons of simulated methane adsorption isotherms at 298 K for experimental, pseudo and pseudo-optimized structures of (a) HKUST-1, (b) IRMOF-1, (c) PCN-14, and (d) MIL-47.

Systematic screening of hypothetical MOFs may depend directly on the accuracy of the predicted properties rather than indirectly on the accuracy of the crystal structures. In one embodiment, methane adsorption isotherms are computationally predicted for the hypothetical MOFs (experimental, pseudo, and pseudo after relaxation/optimization) at 298 K using grand canonical Monte Carlo (GCMC) simulations and in one or more of Snurr et al., Design of new materials for methane storage, *Langmuir* 20, 2683-2689 (2004) and/or Snurr et al., Assessment of isoreticular metal-organic frameworks for adsorption separations: A molecular simulation study of methane/n-butane mixtures, *J. Phys. Chem. B* 108, 15703-15708 (2004). The predicted methane adsorption isotherms matched very closely, particularly between the experimental and pseudo-MOFs where the discrepancies in the crystal structures were less than approximately 0.1 angstroms between atoms of each structure, as shown in FIG. 9. FIG. 9 illustrates comparisons of simulated methane adsorption isotherms at 298 K for experimental, pseudo and pseudo-optimized structures of (a) HKUST-1 (top left graph 900 of FIG. 9), (b) IRMOF-1 (top right graph 902 of FIG. 9), (c) PCN-14 (bottom left graph 904 of FIG. 9), and (d) MIL-47 (bottom right graph 906 of FIG. 9). The graph 900 illustrates a first curve 908 that represents simulated methane adsorption for pseudo-optimized-HKUST-1, a second curve 910 that represents simulated methane adsorption for pseudo-HKUST-1, and a third curve 912 that represents simulated methane adsorption for HKUST-1. The graph 902 illustrates a first curve 914 that represents simulated methane adsorption for pseudo-optimized-IRMOF-1, a second curve 916 that represents simulated methane adsorption for pseudo-IRMOF-1, and a third curve 918 that represents simulated methane adsorption for IRMOF-1. The graph 904 illustrates a first curve 920 that represents simulated methane adsorption for pseudo-optimized-PCN-14, a second curve 922 that represents simulated methane adsorption for pseudo-PCN-14, and a third curve 924 that represents simulated methane adsorption for PCN-14. The graph 906 illustrates a first curve 926 that represents simulated methane adsorption for pseudo-optimized-MIL-47, a second curve 928 that represents simulated methane adsorption for pseudo-MIL-47, and a third curve 930 that represents simulated methane adsorption for MIL-47.

FIG. 17 is a schematic diagram of one embodiment of a system 1700 for generating and/or screening potential MOFs. The system 1700 may be used to determine one or more potential MOFs for various uses. For example, the system 1700 may be used to predict a library or database of potential MOFs, as described above. In one embodiment, the system 1700 is used to carry out one or more operations described above in connection with the method 600 shown in FIG. 6.

The system 1700 includes an input/output assembly 1706, such as a system or assembly having an input device (e.g., electronic mouse, stylus, touchscreen, microphone, and the like) and an output device (e.g., the touchscreen or other display monitor or printer). The input/output assembly 1706 is coupled with a processor 1702, such as a computer processor, controller, or other logic-based device that operates based on one or more sets of instructions (e.g., software applications) stored on a memory 1704 and/or hard-wired into the circuitry of the processor 1702. The memory 1704 can include a tangible and non-transitory computer readable storage medium, such as a computer hard drive, flash drive, CD, DVD, and the like. A database (e.g., a list, table, or other logical structure of information) may be stored on (or represented by) the memory 1704 that includes the library of building blocks, the topological and/or geographical information associated with the building blocks, the pseudo atoms and/or angles associated with connection sites of the building blocks, identified potential MOFs, and the like. The processor 1702 includes or represents several functional modules, which may be embodied in a single processor 1702 and/or multiple processors 1702 operating based on sets of instructions to perform various functions.

The processor 1702 includes an input/output module 1708 that receives input from the input/output assembly 1706 and directs the input/output assembly 1706 to present data to a user of the system 1700. For example, the input/output module 1708 may receive a user input selection of a plurality of building blocks from which the hypothetical or potential MOFs may be formed by the system 1700. As other or additional input, the module 1708 can receive topological and/or geometric information associated with building blocks, pseudo atoms and/or angles associated with connection sites of the building blocks, identified potential MOFs, and the like.

A generation module 1710 creates one or more potential MOFs based on the input received from the input/output module 1708 and/or from a library or database of building blocks stored on the memory 1704. As described above in connection with the method 600 shown in FIG. 6, the generation module 1710 may create the potential MOFs based on a variety of inorganic building blocks, organic building blocks, and/or functional groups. The generation module 1710 may receive topological and/or geometrical information assigned to the various building blocks from the input/output module 1708 and/or from the memory 1704 and use such information to form the potential MOFs, as described above. The generation module 1710 may direct the input/output module 1708 to present the user with one or more of the potential MOFs (e.g., images of the MOFs) on the input/output assembly 1706. For example, the assembly 1706 may visually display the potential MOFs to the user, may print out a hard copy image of the potential MOFs, or the like. At least one technical effect of the system 1700 is to take, as input, various building blocks and to output potential MOFs that can be created after attempting various combinations of the building blocks to identify those MOFs that are feasible. This output may be an electronically presented output, such as graphics, text, and the like, presented on a graphical user interface of a computing device, a hard copy printed version of the graphics, text, and the like, an audibly presented recitation of the potential MOF structures, or some other output.

An evaluation module 1712 examines one or more of the potential MOFs to estimate one or more properties of the potential MOFs. These properties can include chemical and/or mechanical characteristics of the potential MOFs. Alternatively or additionally, these properties can include an estimate cost for actually creating the potential MOFs. For example, the building blocks that are used by the system 1700 to identify the potential MOFs may be associated with estimated costs for acquiring, storing, dispensing, combining, and the like, the building blocks. These costs may be associated with the building blocks in the memory of the system 1700. The costs can be used to generate an estimated production cost for producing each (or one or more of) the potential MOFs should a user of the system 1700 desire to manufacture the potential MOF. The estimated production costs can be presented to the user with the potential MOFs to allow the user to compare the potential MOFs in order to decide which MOFs to produce. The evaluation module 1712 may estimate the chemical characteristics, mechanical characteristics, and/or costs in order to allow for the user to determine which of the potential MOFs may be useful for, or better than one or more other MOFs for, providing a function, such as gas storage. As described above, the evaluation module 1712 may estimate one or more of surface area, pore volume, pore size distribution, powder x-ray diffraction pattern, methane adsorption capability, or the like, associated with each of the potential MOFs. The evaluation module 1712 can use a variety of calculations to determine the material properties of the MOFs. By way of example, the evaluation module 1712 may use an atomistic grand canonical Monte Carlo simulation to estimate adsorption isotherms of methane in the potential MOFs. The evaluation module 1712 can output the characteristics to the input/output assembly 1706 via the input/output module 1708 so that the user can view and/or determine which potential MOF to synthesize for a particular purpose, such as methane or other gas storage.

In one embodiment, once potential MOFs are identified from a library of building blocks as described above, a systematic screening process may be used to identify promising MOFs for one or more uses, such as methane storage in one example. For the generation procedure used by the system 1700 to identify potential MOFs, a library of 60 building blocks that varied significantly in their geometries, number of connection sites, and chemical composition were used. The system 1700 may systematically screen the potential MOFs that are identified for a variety of other applications, such as hydrogen storage, hazardous gas storage, or the like. In one embodiment, the evaluation module 1712 can examine one or more of the potential MOFs that may be useful for the storage of hazardous gases, which may include (but is not limited to) acetylene, arsine, hydrogen selenide, or the like.

Figure 26:
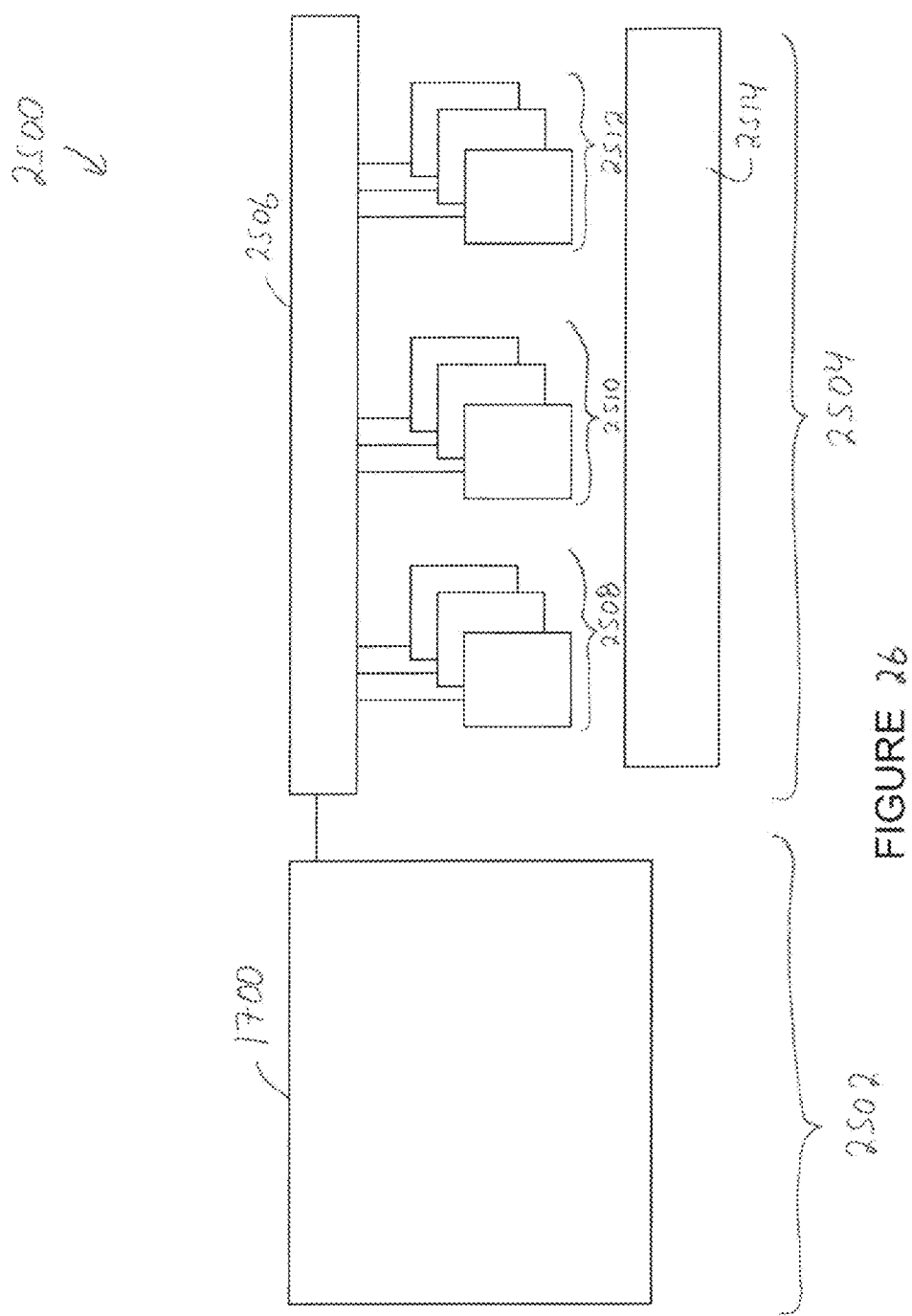
FIG. 26 is a schematic diagram of one embodiment of a MOF generation system.

FIG. 26 is a schematic diagram of one embodiment of a MOP generation system 2500. The generation system 2500 includes a front end component 2502 that includes the system 1700 for generating potential MOFs based on one or more libraries of building blocks, as described above. The generation system 2500 includes a back end component 2504 that represents a fabrication system for creating actual MOFs from the potential MOFs generated by the system 1700. The back end component 2504 includes a control unit 2506 that is communicatively coupled with the system 1700 by one or more wired and/or wireless communication connections. The control unit 2506 is communicatively coupled with one or more sources 2508, 2510, 2512 of building blocks from which the MOFs identified by the system 1700 can be fabricated. For example, the sources 2508 may include containers, tanks, or other receptacles that store and dispense inorganic building blocks, the sources 2510 may include containers, tanks, or other receptacles that store and dispense building blocks, and the sources 2512 may include containers, tanks, or other receptacles that store and dispense functional group building blocks. Alternatively, one or more other sources or the sources shown in FIG. 26 may include catalysts or other species used to create the MOFs identified by the system 1700.

The system 1700 outputs one or more potential MOFs that are identified as described above to the control unit 2506. The system 1700 may notify the control unit 2506 as to which building blocks are used to create the potential MOFs. Using this information, the control unit 2506 directs or controls the sources 2508, 2510, 2512 to dispense the appropriate building blocks (or compounds having the appropriate building blocks) into a receptacle 2514 or other volume. The building blocks may be combined (e.g., either automatically under control of the control unit 2506 or manually under control of a human user) in the receptacle 2514 to create the potential MOF identified by the system 1700. Alternatively or additionally, the system 1700 may output to the user (e.g., by visually displaying, playing audible instructions, printing onto paper, and the like) instructions on how to create the potential MOFs that are identified by the system 1700.

Figure 10:
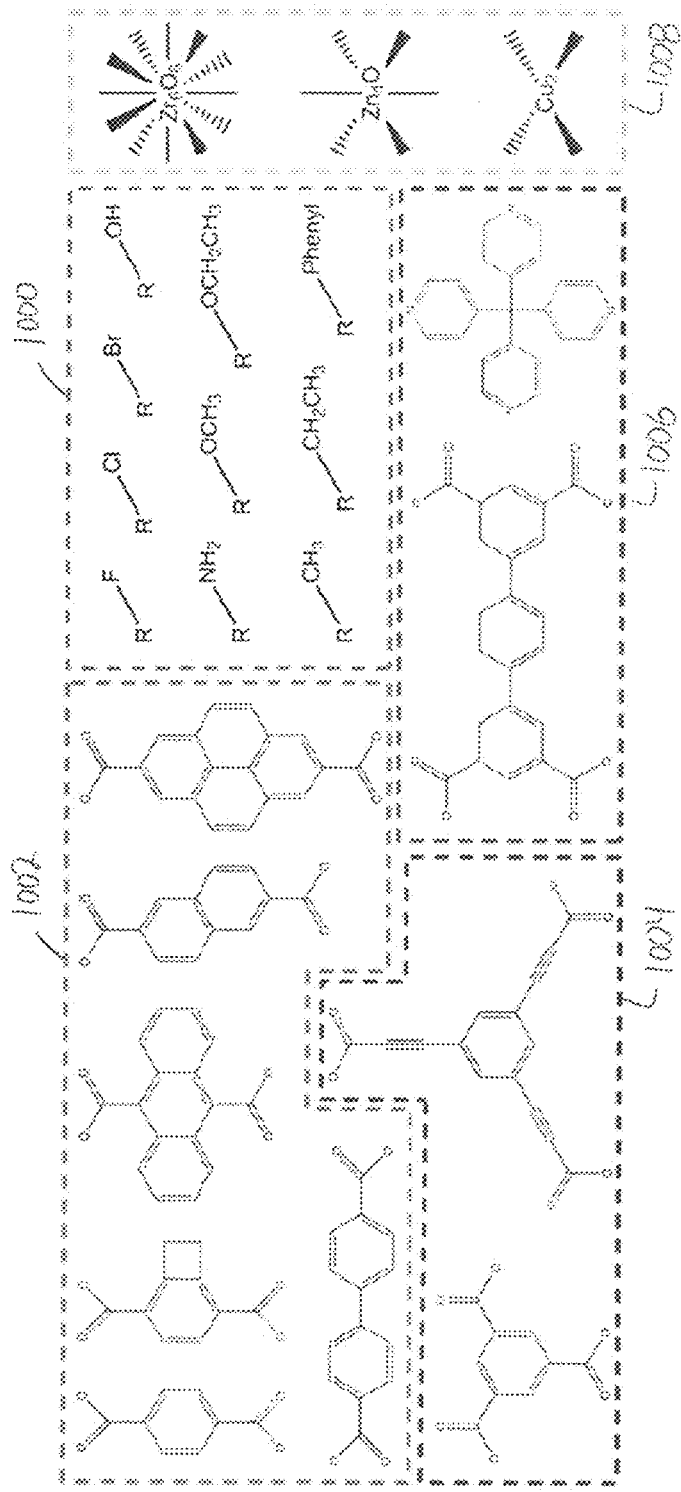
FIG. 10 provides a partial list of the building blocks used for screening the promising MOFs for high pressure methane storage.

FIG. 10 provides a partial list of the building blocks used for screening the promising MOFs for high pressure methane storage. The building blocks shown in FIG. 3 may provide additional building blocks. A purple group 1000, a red group 1002, a green group 1004, and a blue group 1006 show examples of 1-, 2-, 3- and 4-connected building blocks, respectively. The 1-connected building blocks are functional groups while the others (that do not contain metals) are organic building blocks. An orange group 1008 shows three inorganic buildings blocks that are 4-, 6- and 12-connected.

The building blocks may fall conceptually into three groups: inorganic, organic and functional groups. Although the generation algorithm used by the system 1700 is normally blind to these distinctions, it was constrained in one embodiment to produce crystals with at most one kind of inorganic building block, two kinds of organic building blocks, and one kind of functional group. This constraint resulted in MOFs that were reasonable synthetic targets. This constraint may be removed to investigate, for example, the "multivariate" MOFs reported in Deng et al., Multiple functional groups of varying ratios in metal-organic frameworks, *Science* 327, 846-850 (2010), that include up to nine unique building blocks within one crystal.

Atomistic grand canonical Monte Carlo (GCMC) simulations can be performed by the system 1700 to estimate the adsorption isotherms of methane ($CH_4$) in the hypothetical MOFs. Interaction energies between non-bonded atoms can be computed through the Lennard-Jones (LJ) potential represented by:

$$V_{ij} = 4\varepsilon_{ij}\left[\left(\frac{\sigma_{ij}}{r_{ij}}\right)^{12} - \left(\frac{\sigma_{ij}}{r_{ij}}\right)^{6}\right] \quad \text{(Eqn. 6)}$$

where i and j are interacting atoms, and is the distance between atoms i and j, $\varepsilon_{ij}$ and $\sigma_{ij}$ are the LJ well depth and diameter, respectively. LJ parameters between atoms of different types can be calculated using the Lorentz-Berthelot mixing rules (e.g., geometric average of well depths and arithmetic average of diameters). LJ parameters for framework atoms can be obtained from the Universal Force Field (UFF) described in Rappé et al., UFF, a full periodic table force field for molecular mechanics and molecular dynamics simulations, J. Am. Chem. Soc. 114, 10024-10035 (1992). The methane molecules may be modeled using the TraPPE2 force field, which was originally fit to reproduce the vapor-liquid coexistence curve of methane. In this force field, methane is modeled as a single sphere (parameters shown in Table 2 below). Table 2 provides LJ parameters for methane and framework atoms in hypothetical MOFs.

TABLE 2

| Atom type | $\sigma$ (Å) | $\epsilon/k_B$ (K) |
|---|---|---|
| C | 3.43 | 52.83 |
| O | 3.12 | 30.19 |
| H | 2.57 | 22.14 |
| N | 3.26 | 34.72 |
| F | 25.16 | 2.997 |
| Cl | 3.517 | 114.23 |
| Br | 3.73 | 126.30 |
| Zn | 2.46 | 62.40 |
| Cu | 3.114 | 2.516 |
| V | 2.80 | 8.05 |
| Zr | 2.783 | 34.72 |
| $CH_4$ | 3.75 | 148.0 |

Framework parameters may be taken from the Dreiding force field, Mayo et al., A generic force field for molecular simulations, J. Phys. Chem. 94, 8897-8909 (1990), and from UFF when a parameter did not exist in Dreiding. Alternatively, only parameters from UFF may be used. The effect of using parameters from Dreiding and/or UFF or using parameters only from UFF can be examined by comparing methane simulations using both parameter sets (Dreiding UFF versus UFF only) on six MOFs that are diverse in chemical composition and geometry (see FIG. 8).

Figure 8:
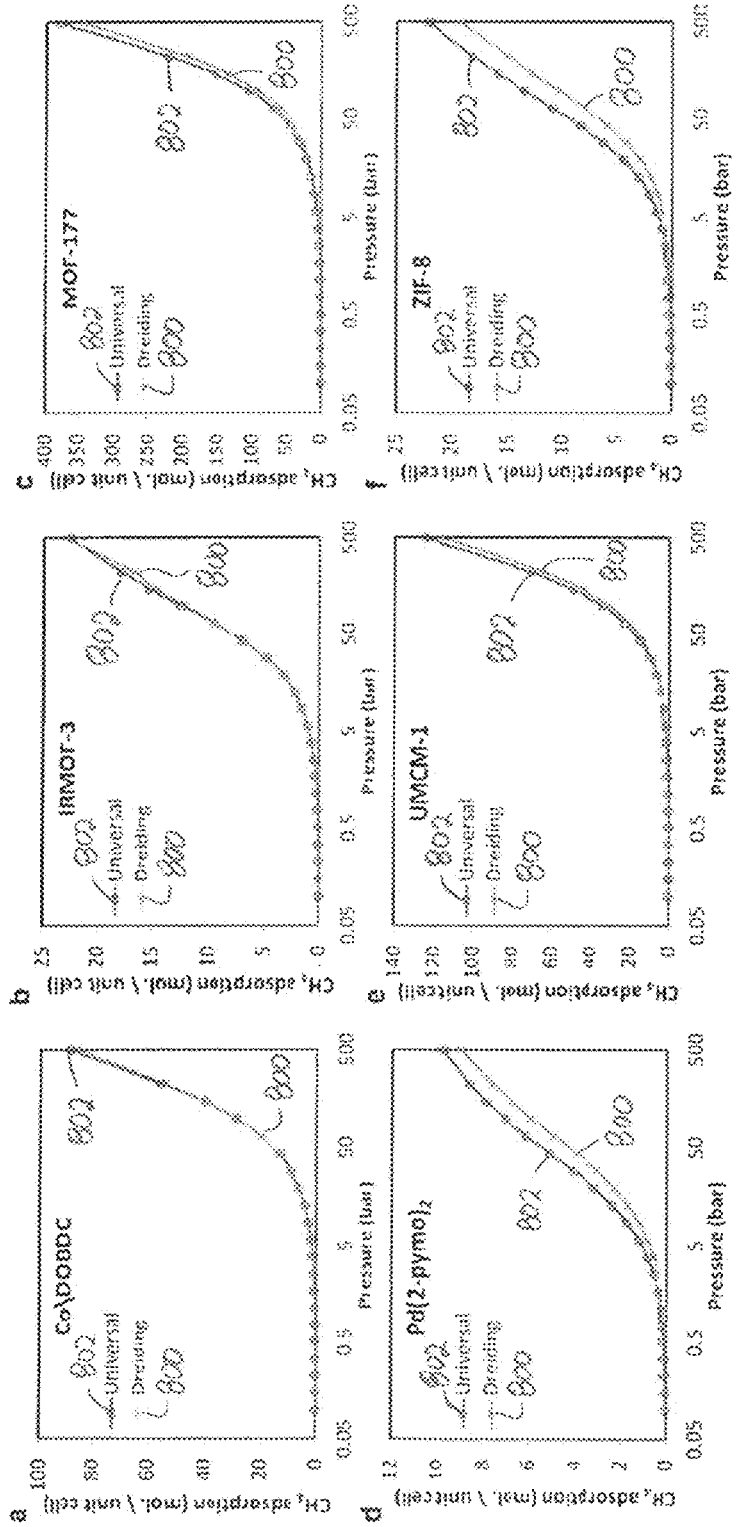
FIG. 8 illustrates a comparison of absolute methane adsorption isotherms at 298 K for six diverse MOFs, using two different sets of force field parameters.

FIG. 8 illustrates a comparison of absolute methane adsorption isotherms at 298 K for six diverse MOFs, using two different sets of force field parameters. The red symbols and curves 800 represent data obtained using framework parameters taken from Dreiding when available and otherwise with using framework parameters from UFF. The blue symbols and curves 802 represent data obtained using framework parameters taken from UFF only. The MOF structures used include Co\DOBDC (e.g., from Dietzel et al., An in situ high-temperature single-crystal investigation of a dehydrated metal-organic framework compound and field-induced magnetization of one-dimensional metal-oxygen chains, *Angew. Chem. Int. Ed.* 44, 6354-6358 (2005)), IRMOF-3 (e.g., from Eddaoudi, Systematic design of pore size and functionality in isoreticular MOFs and their application in methane storage, *Science* 295, 469-472 (2002)), MOF-177 (e.g., from Chae et al., A route to high surface area, porosity and inclusion of large molecules in crystals, *Nature* 427, 523-527 (2004)), Pd(2-pymo)$_2$ (e.g., from Navarro et al., H$_2$, N$_2$, CO, and CO$_2$ sorption properties of a series of robust sodalite-type microporous coordination polymers, *Inorganic Chemistry* 45, 2397-2399 (2006)), UMCM-1 (Koh et al., A crystalline mesoporous coordination copolymer with high microporosity, *Angew. Chem. Int. Ed.* 47, 677-680 (2008)), and ZIF-8 (e.g., from Park et al., Exceptional chemical and thermal stability of zeolitic imidazolate frameworks, *Proc. Natl. Acad. Sci. U.S.A.* 103, 10186-10191 (2006)). Agreement was generally good, with UFF predicting higher adsorption capacity on average. For the purpose of large-scale screening, the UFF parameters may be sufficient to use.

Figure 11:
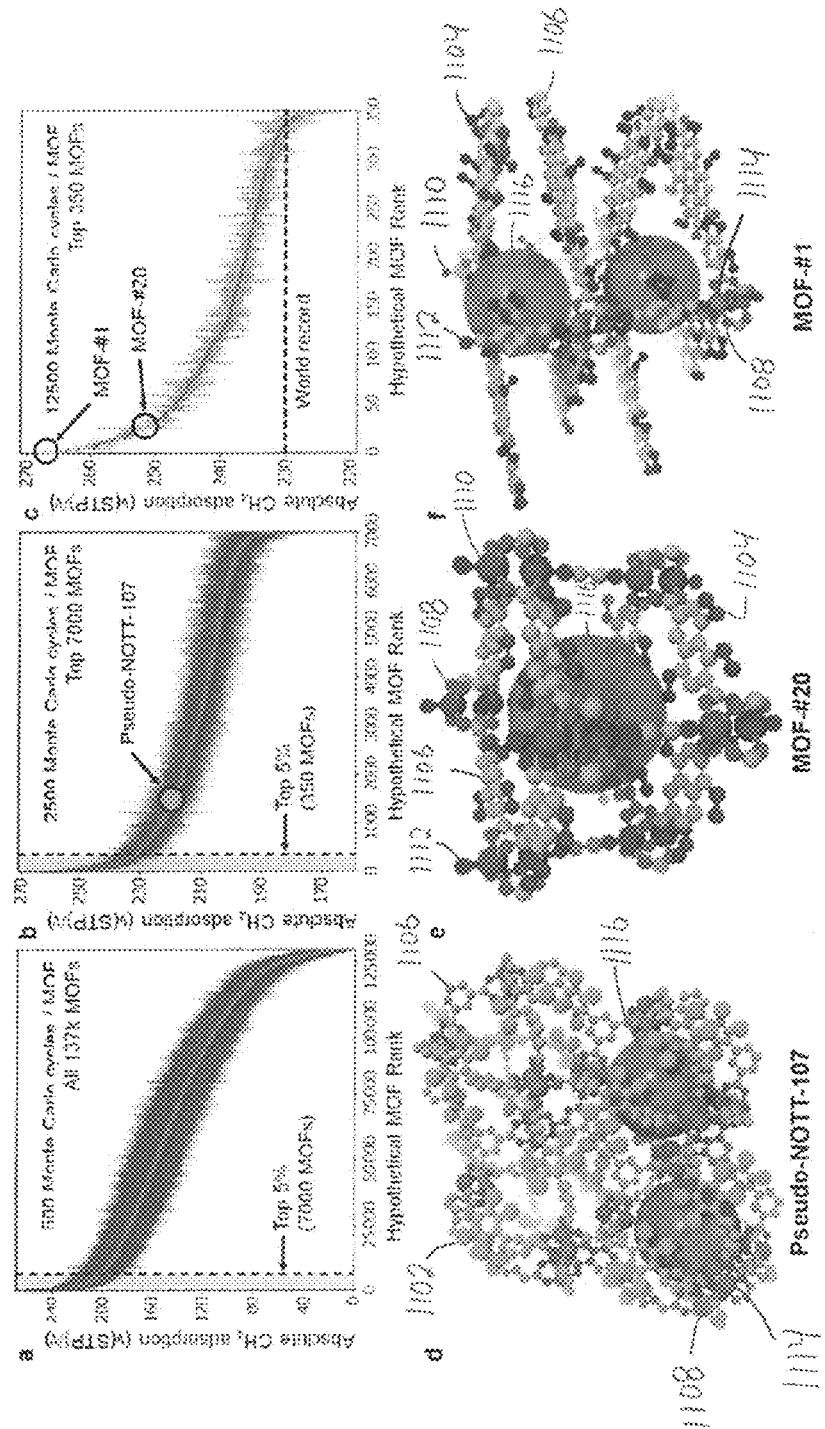
FIG. 11 illustrates the methane adsorption versus hypothetical MOF rank for various MOFs in accordance with one or more embodiments.

The GCMC simulations of methane adsorption included an M-cycle equilibration period followed by an M-cycle production run, where M was 500, 2500, or 12,500 as described below (as shown in FIG. 11). A cycle consists of n Monte Carlo steps; where n is equal to the number of molecules (which fluctuates during a GCMC simulation). The simulations included random insertion, deletion, and translation moves of molecules with equal probabilities. Atoms in the MOF were held fixed at their crystallographic positions. An LJ cutoff distance of 12.8 angstroms was used for the simulations. A 2×2×2 unit cell of every crystal was used for the simulations.

Methane adsorption was simulated at a single pressure, 35 bar, at 298 K for all crystals. In addition, a complete isotherm was calculated (over a wide range of pressures) for the four MOFs (HKUST-1, IRMOF-1, PCN-14, and MIL-47) described in FIG. 9. Fugacities needed to run the GCMC simulations were calculated using the Peng-Robinson equation of state. GCMC simulations report the absolute adsorption data, which are then used to compute the excess adsorption data for comparison with experimental data using the relation:

$$N_{total} = N_{excess} + \rho_{gas} \times V_p \qquad (\text{Eqn. 7})$$

where $\rho_{gas}$ is the bulk density of the gas at simulation conditions, calculated with the Peng-Robinson equation of state, and $V_p$ is the pore volume calculated by the helium insertion method as described in Snurr et al., Effects of surface area, free volume, and heat of adsorption on hydrogen uptake in metal-organic frameworks, *J. Phys. Chem. B* 110, 9565-9570 (2006).

The structure labeled "MOF-#1" in (f) of FIG. 11 (described below) is composed of building blocks 3, 31 (nitrogen terminated), 35, and 52, as shown in FIG. 3. The structure labeled "MOF-#20" in (e) of FIG. 11 is composed of building blocks 2, 19, 25 (nitrogen terminated) and 52 as depicted in FIG. 3. CIF structures also are available along with others.

The methane adsorption isotherm was simulated for the PCN-14 structure as described in the above method, but at 290 K to better represent the experiment conducted by Ma et al., Metal-organic framework from an anthracene derivative containing nanoscopic cages exhibiting high methane uptake, *J. Am. Chem. Soc.* 130, 1012-1016 (2008). A BET surface area was calculated as described in Snurr et al., Applicability of the BET method for determining surface areas of microporous metal-organic frameworks, *J. Am. Chem. Soc* 129, 8552-8556 (2007), over a pressure range of 0.003<P/P$_0$<0.1 from a simulated N$_2$ isotherm at 77 K (shown in FIG. 14 on the right side of the figure) using the same parameters as above and 5000 cycles per data point.

Figure 14:
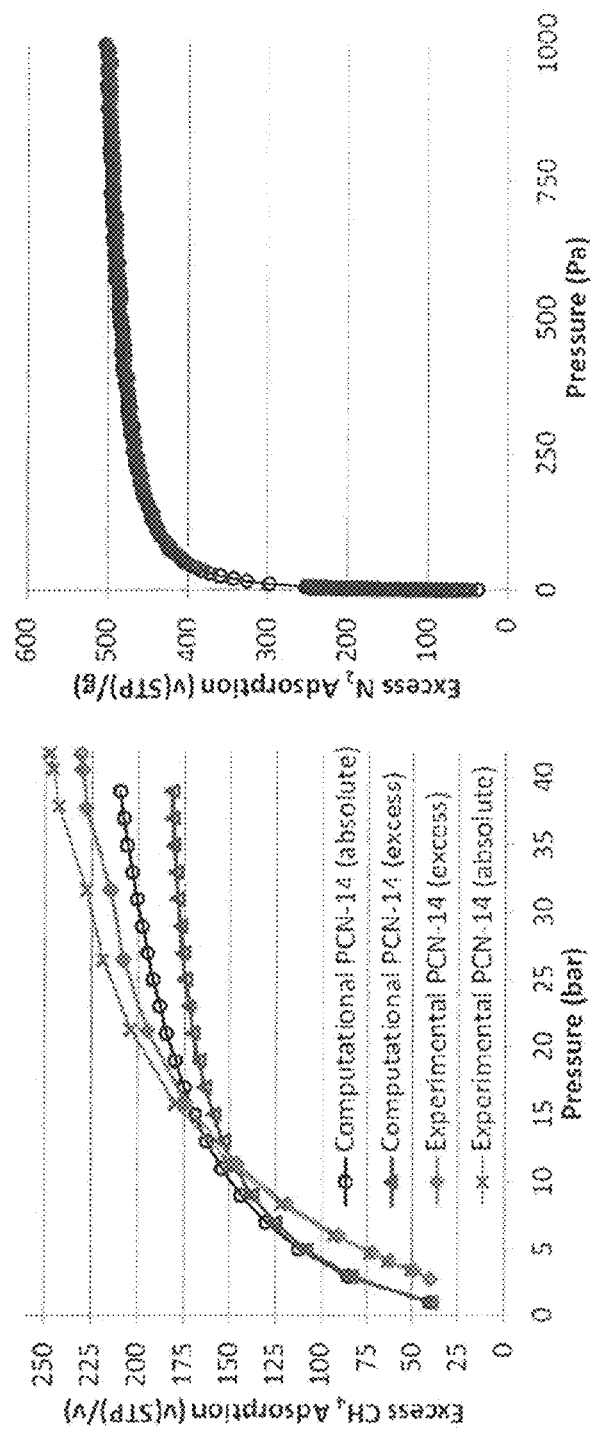
FIG. 14 illustrates simulated and experimental methane adsorption isotherms for PCN-14 at 290 K and N2 isotherm at 77K.

FIG. 14 illustrates simulated and experimental methane adsorption isotherms for PCN-14 at 290 K and the simulated N$_2$ isotherm at 77 K. The simulated and experimental methane adsorption is shown in the left side of FIG. 14 (experimental data from Ma et al.), and the simulated N$_2$ isotherm is shown on the right side of FIG. 14.

By attempting several combinations of building blocks subject to the above constraints, a total of 137,953 hypothetical MOF structures are generated in one embodiment. These hypothetical MOF structures can be screened (e.g., examined) for methane storage at 35 bar and 298 K, and/or other properties can be calculated, such as surface area, void fraction, pore size distribution, and powder x-ray diffraction pattern. Screening may be performed in three stages: each MOF was subject to short 500 cycle GCMC simulations, then the top 7000 MOFs were subjected to 2500 cycle simulations, and finally the top 350 from the second stage were subjected to 12500 cycles simulations.

FIG. 11 illustrates the methane adsorption versus hypothetical MOF rank for various MOFs in accordance with one or more embodiments. In the initial stage, approximately 137 k MOFs were screened for methane storage at 35 bar via short simulations (e.g., the left graph (a) in FIG. 11). The top 5% of the first stage (e.g., shown in the middle graph (b) in FIG. 11) and then the top 5% of the second stage (e.g., shown in the right graph (c) in FIG. 11) were recalculated using successively longer simulations, which reduced the statistical error significantly each time. In graphs (a) through (c), the MOFs are rank-ordered (best to worst runs from left to right in FIG. 11) with statistical error indicated via bars 1100.

In (d) of FIG. 11, Pseudo-NOTT-107 was generated automatically by the system 1700 and method 600 described above ("pseudo" to distinguish from the empirical structure) and shows good methane storage capacity. In (e) and (f) of FIG. 11, additional examples of hypothetical MOFs are provided with very high methane storage at 35 bar; the highest value was 267 v(STP)/v. In (d) through (f) of FIG. 11, orange spheres 1102 and green spheres 1104 represent the carbon atoms of methyl and ethyl functional groups, respectively, and grey spheres 1106, red spheres 1108, blue spheres 1110, turquoise spheres 1112, and brown spheres 1114 represent carbon, oxygen, nitrogen, zinc and copper atoms, respectively. Largest pore diameters are indicated by purple spheres 1116 and hydrogen atoms have been omitted for clarity.

The third stage (e.g., highest quality) GCMC predictions indicate that approximately 300 MOFs have higher methane storage capacity at 35 bar than one or more currently known storage capacities, such a known capacity of 230 v(STP)/v. For example, one hypothetical MOF (shown in (f) of FIG. 11) is predicted to store approximately 267 v(STP)/v methane at 298 K.

In addition to identifying promising candidates for methane storage, trends among various potential MOFs may be identified. For example, a clear linear relationship (or other relationship) may exist between volumetric methane adsorption and volumetric surface area, but not between volumetric methane adsorption and gravimetric surface area. Increasing or maximizing gravimetric surface area can be a common strategy in MOF design, but going past an "optimal" point, such as a gravimetric surface area of approximately 2500 to 3000 m²/g, may worsen the methane storage capability of the MOF. Despite diverse topological and chemical differences, some of the best hypothetical MOFs share a relatively narrow cusp of optimal void fractions around approximately 0.8 (as shown in (c) of FIG. 12, described below). Similar to gravimetric surface area, a pore volume that is larger than an "optimal" point may have a steeply negative effect on methane storage. MOFs with methyl, ethyl and propyl functional groups dominate the best performers; over 75% of MOFs with adsorption over 205 v(STP)/v may include methyl, ethyl, or propyl functional groups, as shown in (d) and (e) of FIG. 12.

Figure 7:
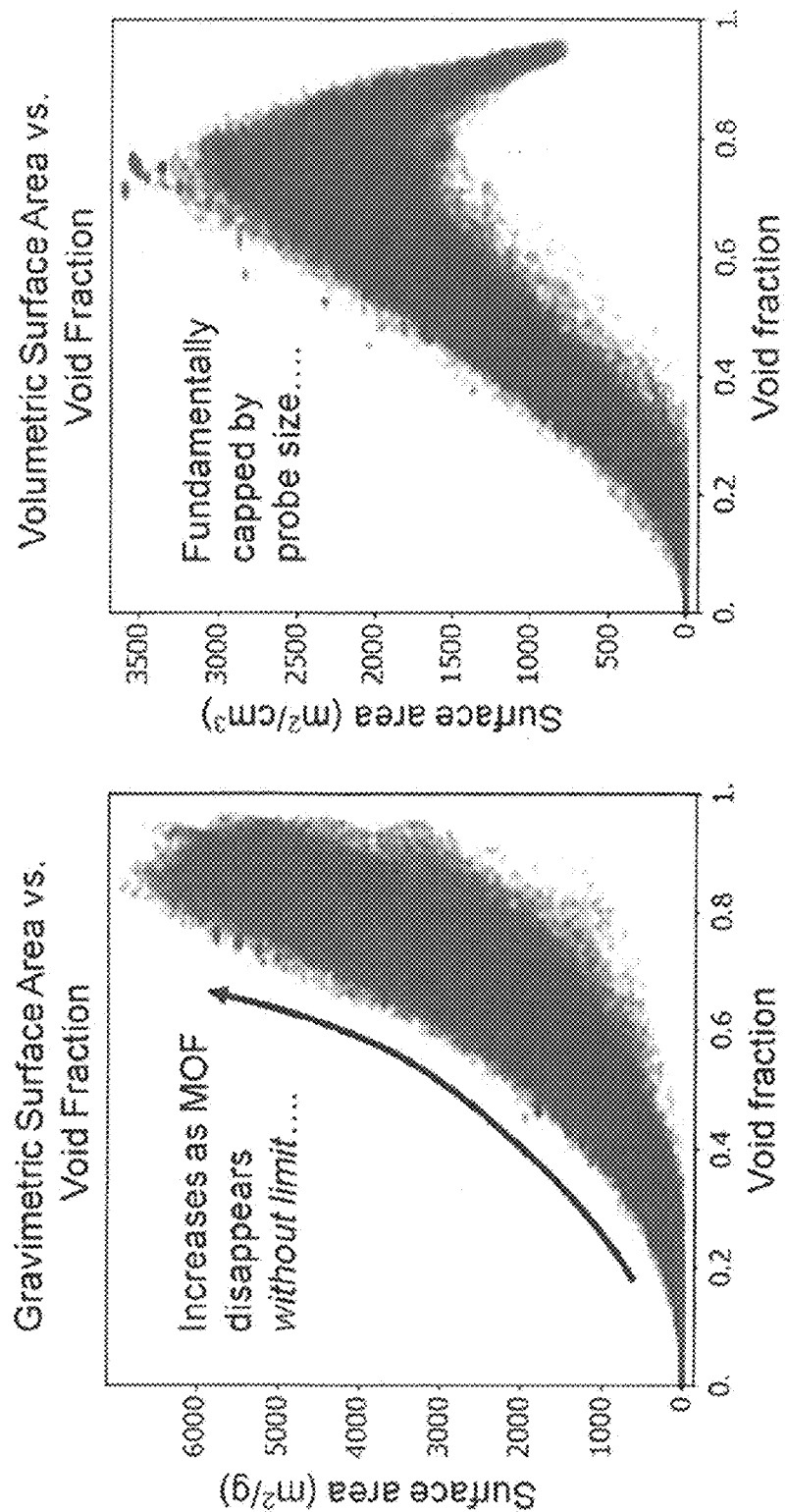
FIG. 7 illustrates two structure-property relationships found in a database of the MOFs generated using the techniques described above that are geometric in nature.

FIG. 7 illustrates two structure-property relationships found in a database of the MOFs generated using the techniques described above that are geometric in nature. The data shown in FIG. 7 suggests that volumetric surface area may be fundamentally capped to a value determined by the probe size used, whereas gravimetric surface area may not show a clear limit.

Figure 12:
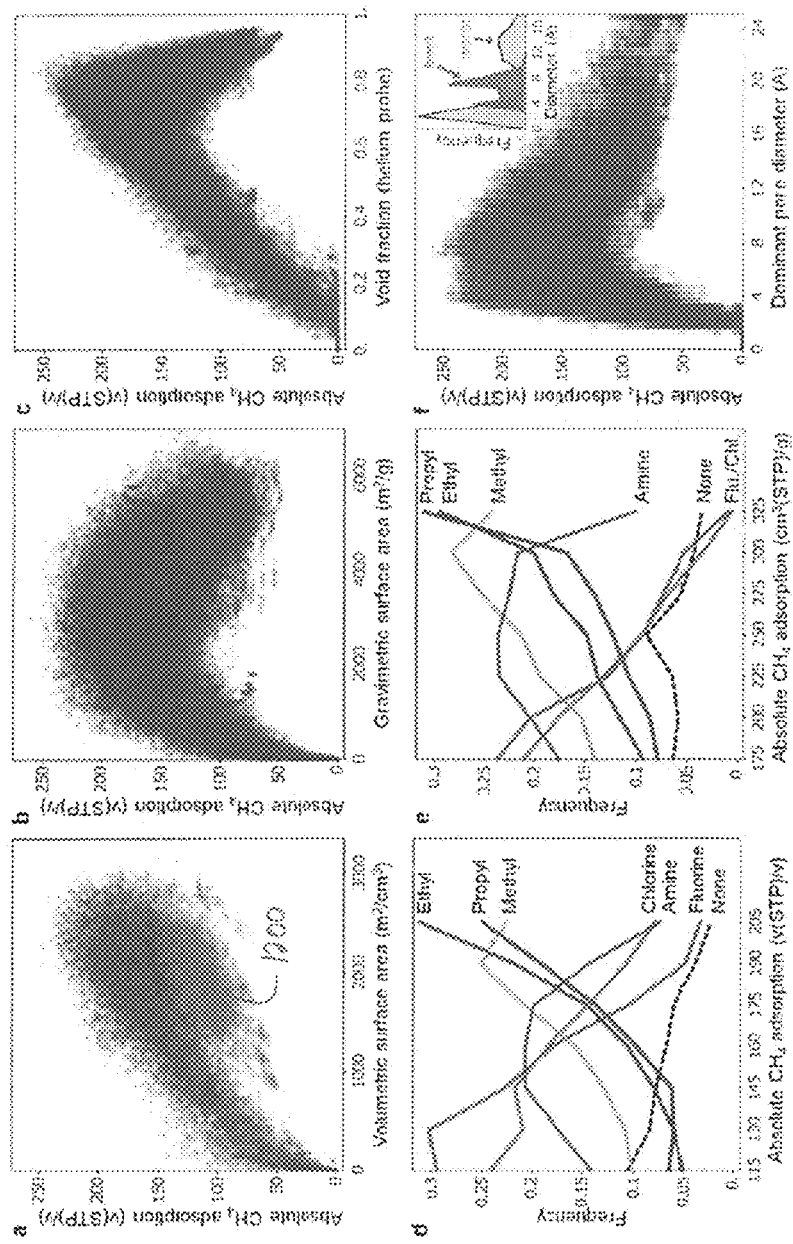
FIG. 12 illustrates structure-property relationships obtained from a database of hypothetical MOFs in accordance with one embodiment.

FIG. 12 illustrates structure-property relationships obtained from a database of hypothetical MOFs in accordance with one embodiment. As shown in FIG. 12, the volumetric methane adsorption may show a clear linear relationship with volumetric surface area (e.g., as shown in (a) of FIG. 12), but may not show such a relationship between volumetric methane adsorption and gravimetric surface area (e.g., as shown in (b) of FIG. 12). In FIG. 12, red dots 1200 correspond to MOFs that have enough space to interpenetrate, but are not interpenetrated. With respect to (b) in FIG. 12, methane adsorption initially increases with gravimetric surface area, but then begins to decrease with the optimal gravimetric surface area approximately 2500-3000 m²/g. With respect to (c) in FIG. 12, a void fraction of approximately 0.8 may be optimal or better than one or more other void fractions for volumetric methane uptake at 35 bar. As shown in (d) and (e) of FIG. 12, methyl, ethyl and propyl groups occur more frequently in MOFs that have volumetric and gravimetric methane adsorption greater than 205 v(STP)/v and 325 cm³ (STP)/g, respectively. Halogen functional groups may be suboptimal for methane storage and may be weakly represented amongst the best MOFs for volumetric storage and completely absent from the top MOFs by gravimetric adsorption. With respect to (f) of FIG. 12, MOFs in the database have a range of dominant pore sizes. The inset in FIG. 12 shows that pore sizes of 4 angstroms and 8 angstroms are more common in the "best" MOFs, while the "worst" MOFs specifically exclude pore sizes in the range of 4 to 8 angstroms. The term "best" refers to MOFs having methane adsorption greater than 220 v(STP)/v, but may or may not include the highest methane adsorptions. The term "worst" refers to MOFs having methane adsorption less than 120 v(STP)/v, but may or may not include the lowest methane adsorptions.

Since methyl-functionalized MOFs generally have high methane uptake (see (d) in FIG. 12) and NOTT-107 has four methyl groups per organic linker, NOTT-107 can be investigated as a candidate methane storage material. NOTT-107 is in the top 2% of MOFs in the database described above, and it also may be attractive to study because NOTT-107 can be easily compared to PCN-14, a MOF that is currently reported to have the highest methane storage at 35 bar or a methane storage at 35 bar that is higher than one or more other MOFs.

Figure 13:
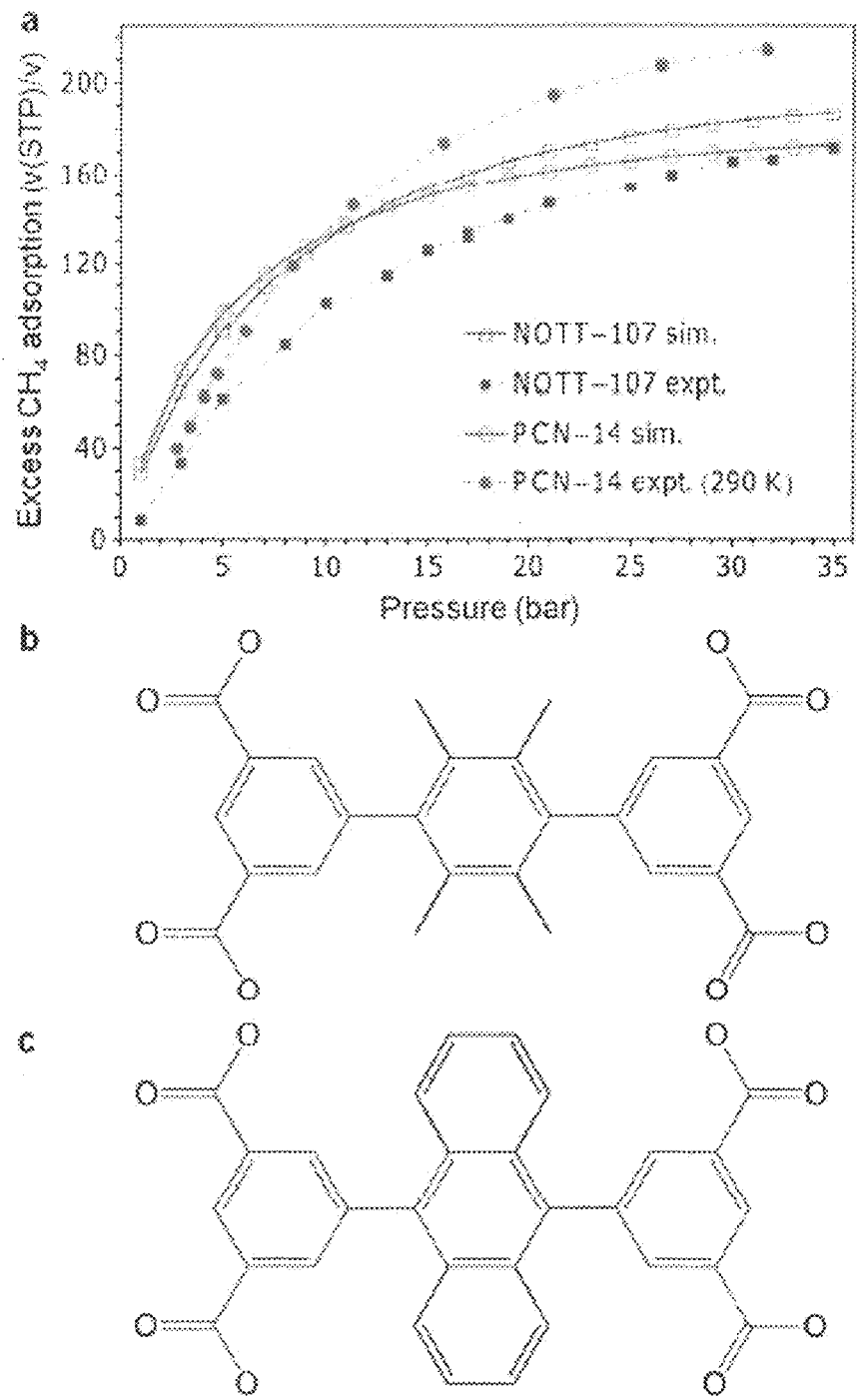
FIG. 13 illustrates a comparison of excess methane adsorption isotherms of NOTT-107 (ligand 13b) and PCN-14 (ligand 13c) in accordance with one embodiment.

FIG. 13 illustrates a comparison of excess methane adsorption isotherms of NOTT-107 and PCN-14 in accordance with one embodiment. The isotherm data is at 298 K except experimental data for PCN-14, which is taken from Ma et al., Metal-organic framework from an anthracene derivative containing nanoscopic cages exhibiting high methane uptake, *J. Am. Chem. Soc.* 130, 1012-1016 (2008) and is at 290 K. In one embodiment, NOTT-107 is structurally identical to PCN-14 except for the organic building block, which has four methyl groups (e.g., as shown in (b) of FIG. 13) in the place of two fused aromatic rings (e.g., as shown in (c) of FIG. 13). *J. Am. Chem. Soc.*, 131, 2159 (2009).

These MOFs (NOTT-107 and PCN-14) may use the same inorganic building block and have identical topologies and differ in the organic building block used (as shown in FIG. 13). Although MOFs with many aromatic rings have relatively high methane uptake, methyl functional groups can have a greater effect. GCMC simulations show NOTT-107 to be a slightly better methane storage material than PCN-14 at 298 K as shown in FIG. 13. Absolute storage quantities for NOTT-107 and PCN-14 at 35 bar were calculated to be 213 v(STP)/v and 197 v(STP)/v, respectively. Note that FIG. 13 displays the excess adsorption, which is more directly measured in adsorption experiments.

From experimental measurements, simulations may overpredict methane storage by approximately 9% at 35 bar for NOTT-107. This may partly be attributed to incomplete pore activation, which is corroborated by a difference between the simulated BET surface area (2207 m2/g) (e.g., from Snurr et al., Applicability of the BET method for determining surface areas of microporous metal-organic frameworks, *J. Am. Chem. Soc* 129, 8552-8556 (2007)) versus the measured BET surface area (1770 m2/g). The experimentally measured methane adsorption for PCN-14 by Ma et al., Metal-organic framework from an anthracene derivative containing nanoscopic cages exhibiting high methane uptake, *J. Am. Chem. Soc,* 130, 1012-1016 (2008), at 290 K, however, is significantly higher than a model predicts, which can be surprising given the similarity of the PCN-14 and NOTT-107 structures (predicted adsorption isotherms of the two MOFs are very similar, see (a) in FIG. 13). Taking the 8 K lower temperature into account can increase the simulated absolute adsorption to 205 v(STP)/v (from 197), but this is still well below the reported value: 230 v(STP)/v (as described above in connection with the disclosed simulations).

In the future one can also imagine the structure generation process being more adaptive and creative. For example, adding propyl building blocks to the library of building blocks based on positive results using methyl and ethyl functional groups; similar insights could lead to the design of new building blocks which could subsequently be fed back into the generator as an iterative optimization strategy.

It should be noted that the methods described herein may be limited to rigid frameworks in one embodiment. However, the space of possible rigid frameworks is very large and the screening strategy described herein can greatly accelerate its exploration.

While several structure-property relationships are described herein, many others may exist and are not excluded from the scope of the inventive subject matter described herein. The screening method described herein may be used for applications beyond methane storage and subsequently synthesizing improved materials for applications such as carbon capture, hydrogen storage, and chemical separations, among other uses.

All air- or water-sensitive reactions used to provide the results described herein were carried out under a dry nitrogen atmosphere using standard Schlenk techniques. Reagents and reagent-grade solvents were purchased from either VWR, Strem, or Aldrich Chemical Company and used as received. Silica gel was purchased from Sorb. Tech. $^1$H and $^{13}$C NMR spectra were recorded on a Bruker 500 FT-NMR spectrometer (499.773 MHz for $^1$H, 125.669 MHz for $^{13}$C). $^1$H NMR data are reported as follows: chemical shift (multiplicity (b=broad singlet, s=singlet, d=doublet, dd=doublet of doublets, ddd=doublet of doublets of doublets, t=triplet, q=quartet, and m=multiplet), integration, and peak assignments, coupling constants). $^1$H and $^{13}$C chemical shifts are reported in ppm from TMS with residual solvent resonances as internal standards. Powder X-ray diffraction (PXRD) data were recorded on a Rigaku ATX-G diffractometer using nickel-filtered Cu Kα radiation. Data were collected over the range of 5°<2(θ)<40° in 0.05° steps at a scan rate of 2°/min. Supercritical CO2 processing was performed with a Tousimis™ Samdri® PVT-30 critical point dryer. All manipulations of activated samples were done in an argon atmosphere glove box to avoid contact with water. Surface area calculations used nitrogen adsorption isotherms measured at 77.3 K on a Tristar 3020 by Micromeritics. The BET surface area was calculated between $0.003<P/P_0<0.1$ and the correlation was 0.99993 and the intercept positive. An activated sample (28 mg) was placed into a preweighed glass holder. Analysis temperature was held at a constant 77.3 K in a liquid nitrogen bath. High pressure (1 to about 65 bar) methane adsorption measurements were carried out on an HPVA-100 from VTI Instruments. The sample was held at 298 K in a circulating water bath. A 2 cc stainless steel sample holder was loaded with the activated sample (258 mg) in an argon atmosphere glove box and sealed prior to analysis. All gases (He, N2, and CH4) used for analysis were of ultra-high purity grade (>99.99% pure) from Airgas and were used without further purification. Microwave heating was carried out using an automatic single-mode synthesizer (Initiator™ 2.0) from Biotage, which produces a radiation frequency of 2.45 GHz.

Figure 15:
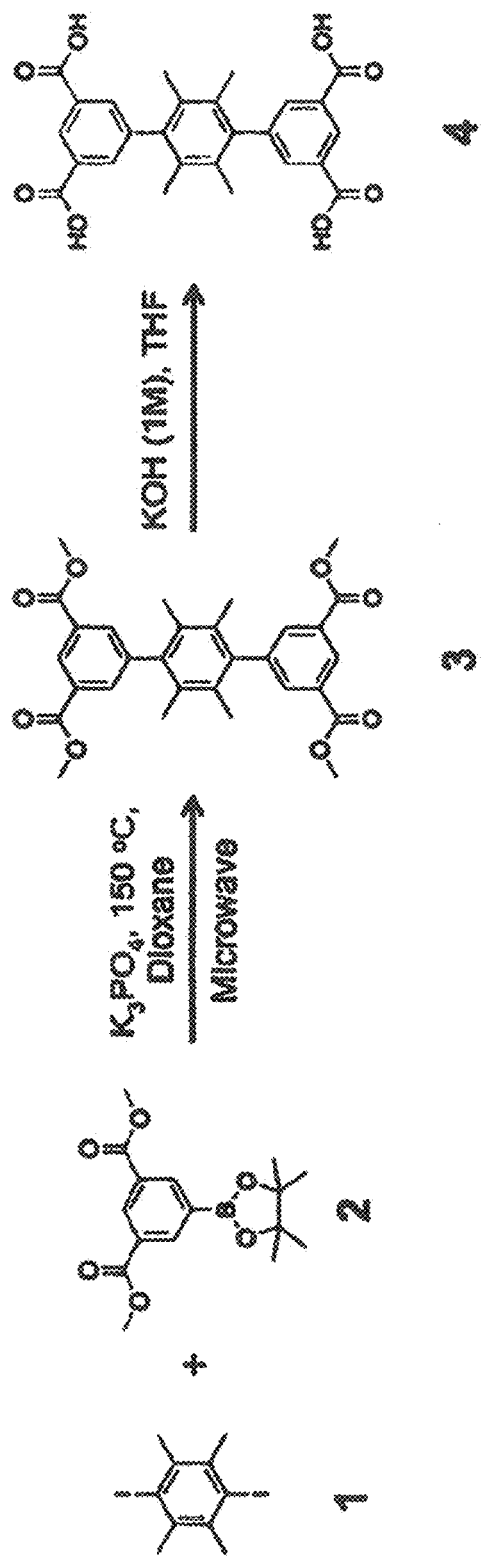
FIG. 15 illustrates synthesis of tetracarboxylate ligand 4 in accordance with one embodiment.

FIG. 15 illustrates synthesis of tetracarboxylate ligand 4 in accordance with one embodiment. The synthesis of (3) shown in FIG. 15 includes, in one embodiment, combining 1,4-diiodo-2,3,5,6-tetramethylbenzene (shown as (1) in FIG. 15 and can be purchased from VWR) (0.60 g, 1.55 mmol) and 3,5-Bis(methoxycarbonyl) phenylboronic acid pinacol ester (shown as (2) in FIG. 15 and prepared following Chen et al., A new multidentate hexacarboxylic acid for the construction of porous metal-organic frameworks of diverse structures and porosities, *Cryst. Growth Des.* 10, 2775-2779 (2010) (1.09 g, 3.41 mmol), $K_3PO_4$ (1.97 g, 9.30 mmol) and dioxane (15 ml) in 10-20 ml capacity microwave vials and degassed for 10 min with nitrogen. $Pd(PPh_3)_4$ (0.040 g, 0.03 mmol) was added and the vial was microwave heated with stirring at 150° C. for 6 hours. After cooling, $CH_2Cl_2$ (30 mL) was added and the organic layer was washed with water (20 mL×3). The organic layer was dried over $MgSO_4$ and evaporated under vacuum. The resulting solid was washed with MeOH and then dried under vacuum to give a white solid (0.56 g, 70%). $^1$H NMR (500 MHz, $CDCl_3$): 8.73 (t, J=1.5 Hz 2H), 8.10 (d, J=1.6 Hz, 4H), 3.99 (s, 12H), 1.94 (s, 12H); $^{13}$C NMR (125 MHz, $CDCl_3$) δ 166.4, 143.4, 139.8, 134.8, 132.0, 130.9, 129.1, 52.5, 18.2.

For the synthesis of (4) shown in FIG. 15, to a stirring solution of 3 (1 g, 1.93 mmol) in THF (50 mL), KOH (120 mL of a 1 M aqueous solution, 120 mmol) was added. The mixture was refluxed for 15 hours until it became clear. THF was removed using a rotary evaporator and the remaining aqueous solution was acidified to pH 2 using concentrated HCl (15 mL of a 37% aqueous solution). The resulting precipitate was collected via filtration, washed with $H_2O$ (200 mL), and dried under high vacuum to afford (4) shown in FIG. 15 as a white solid (0.80 g 90%). $^1$H NMR (500 MHz, $DMSOd_6$): δ 8.51 (s, 2H), 7.91 (s, 4H), 1.88 (s, 12H); $^{13}$C NMR (125 Mz, $CDCl_3$) δ 166.5, 142.6, 139.3, 133.9, 131.7, 131.4, 128.4, 17.9.

In order to synthesize NOTT-107, in accordance with one embodiment, a mixture of $Cu(NO_3)_2.2.5H_2O$ (600 mg, 2.6 mmol) and (4) shown in FIG. 15 (360 mg, 0.78 mmol) was dissolved in a mixture of DMF (60 mL) in a beaker. Then 60 ml of ethanol and 24 drops of conc. HCl were added to the solution and mixed well. This solution was divided between 15 6-dram vials. The vials were capped and placed into an oven at 80° C. for 24 hours. The resulting teal crystalline powder was combined and washed with DMF.

For the activation of NOTT-107, prior to drying, DMF/EtOH-solvated MOF samples were soaked in absolute ethanol, replacing the soaking solution every 24 hours for 3 days. After soaking, the ethanol-containing samples were placed inside the supercritical $CO_2$ dryer and the ethanol was exchanged with $CO_2$(liq.) over a period of 8 hours. During this time, the liquid $CO_2$ was vented under positive pressure for three minutes every two hours. The rate of venting of $CO_2$(liq.) was kept below the rate of filling so as to maintain a full or relatively full drying chamber.

Then the chamber was sealed and the temperature was raised to 38° C. (i.e., above the critical temperature for carbon dioxide), at which time the chamber was slowly vented over the course of 15 hours. The color of the MOF changed from teal to dark blue. The collected MOF sample was then stored inside an inert-atmosphere glovebox until further analysis. Prior to sorption measurements, the sample was evacuated at room temperature for three hours, then brought to 110° C. over four hours.

Figure 16:
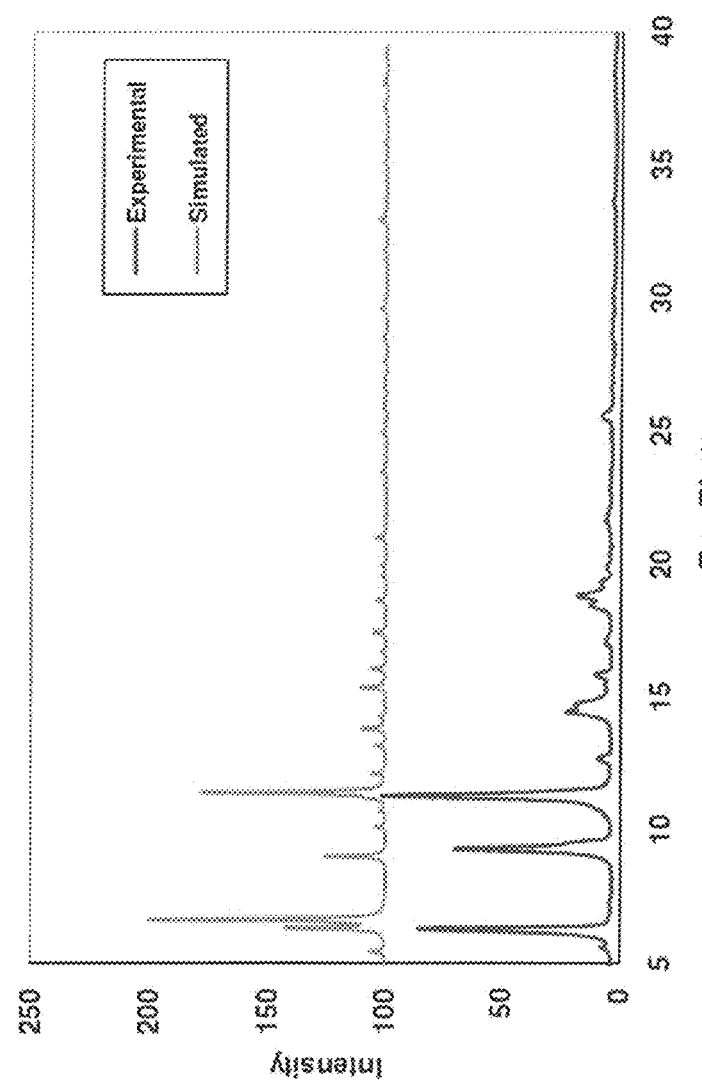
FIG. 16 provides powder x-ray diffraction patterns of NOTT-107, including both experimental (below) and simulated (above) in accordance with one embodiment.

FIG. 16 provides powder x-ray diffraction patterns of NOTT-107, including both experimental (below) and simulated (above) in accordance with one embodiment.

The MOFs disclosed herein can be considered in the context of coordination of an inorganic metal center block component with one or more organic linker/ligand block components comprising terminal carboxy (e.g., via coordination with a carboxylate group, such group in the presence of a suitable counter ion such as but not limited to an alkaline or alkaline-earth metal ion) and/or analogous nitrogenous groups, such linker/ligand block components of the sort represented in FIGS. 3A-C. Specific examples of metals contemplated include, but are not limited to, any oxidation state of magnesium, calcium, strontium, barium, radium, aluminum, gallium, indium, thallium, silicon, germanium, tin, lead, arsenic, antimony, scandium, titanium, vanadium, chromium, manganese, iron, cobalt, nickel, copper, zinc, yttrium, zirconium, niobium, molybdenum, technetium, rubidium, rhodium, palladium, silver, cadmium, hafnium, tantalum, tungsten, rhenium, osmium, iridium, platinum, gold, mercury, lanthanum, cerium, praseodymium, neodymium, promethium, samarium, europium, gadolinium, terbium, dysprosium, holmium, erbium, thulium, and ytterbium. Metal components that can coordinate to such ligands comprise metal ions such as but not limited to $Mg^{2+}$, $Ca^{2+}$, $Sr^{2+}$, $Ba^{2+}$, $Sc^{3+}$, $Y^{3+}$, $Ti^{4+}$, $Zr^{4+}$, $Hf^{4+}$, $V^{4+}$, $V^{3+}$, $V^{2+}$, $Nb^{3+}$, $Ta^{3+}$, $Cr^{3+}$, $Mo^{3+}$, $W^{3+}$, $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $C^{2+}$, $Rh^{2+}$, $Rh^{+}$, $Ir^{2+}$, $Ir^{+}$, $Ni^{2+}$, $Ni^{+}$, $Pd^{2+}$, $Pd^{+}$, $Pt^{2+}$, $Pt^{+}$, $Cu^{2+}$, $Cu^{+}$, $Ag^{+}$, $Au^{+}$, $Zn^{2+}$, $Cd^{2+}$, $Hg^{2+}$, $Al^{3+}$, $Ga^{3+}$, $In^{3+}$, $Tl^{3+}$, $Si^{4+}$, $Si^{2+}$, $Ge^{4+}$, $Ge^{2+}$, $Sn^{4+}$, $Sn^{2+}$, $Pb^{4+}$, $Pb^{2+}$, $As^{5+}$, $As^{3+}$, $As^{+}$, $Sb^{5+}$, $Sb^{3+}$, $Sb^{+}$, and $Bi^{5+}$, $Bi^{3+}$, and $Bi^{+}$. Such metal ions are available through corresponding metal salts, in conjunction with any acceptable counter ion(s), such as but not limited to nitrate. In certain non-limiting embodiments, such metals can be transition metals, such as any oxidation state of vanadium, copper, zinc and zirconium. Specific metals and oxidation states contemplated for use in the MOFs disclosed herein include, but are not limited to, $Zr^{4+}$, $V^{4+}$, $V^{3+}$, $Cu^{2+}$, $Cu^{+}$, and $Zn^{2+}$. Without limitation, as can relate to various MOFs illustrated herein, metal centers associated with inorganic block components can include Cu2, Zn40, Zn2, V3O3, and Zr6O6.

As used herein, the term "polymeric crystalline structures" can refer to polymers of inorganic metal center block components coordinated to one or more organic linker/ligand block components. The materials produced herein can be "crystalline," which refers to the ordered definite crystalline structure such a material which is unique and thus identifiable by a characteristic X-ray diffraction pattern.

In some cases, the MOFs disclosed herein are substantially free of solvents. As used herein "substantially free" means that solvents are present in the MOF at levels less than 1 wt % by weight of the MOF, and preferably from 0 wt % to about 0.5 wt % by weight of the MOF. The solvent can be removed from the MOF by exposing the MOF to elevated temperatures under reduced pressure, or by soaking the MOF in a low boiling solvent to exchange the coordinated solvent for the low boiling solvent, then exposing the MOF to reduced pressure. The amount of solvent in the MOF can be determined by elemental analysis or other known analytical techniques.

The pore size of the MOFs disclosed herein can be altered depending upon the number of solvent molecules coordinated or partially coordinated to the metal center. Typically, the pore size of the MOF will be about 3 Å to about 11 Å, but can be about 4 Å to about 8 Å. The Brunauer, Emmett, and Teller (BET) surface area of the MOFs disclosed herein can be about 100 to about 3500 $m^2/g$. In some cases, the BET surface area is about 100 to about 2500 $m^2/g$, about 150 to about 2000 $m^2/g$, about 150 to about 1500 $m^2/g$, about 150 to about 1000 $m^2/g$, and about 100 to about 250 $m^2/g$.

As mentioned, above, one or more embodiments of the inventive subject matter can be directed to compositions comprising MOFs of the sort disclosed herein. Such compositions can include one or more MOF and a binder, an organic viscosity-enhancing compound, and/or a liquid for converting the MOF into a paste. Such compositions can, optionally, be molded, extruded, co-extruded, foamed, spray dried and/or granulated or otherwise processed to form a shaped body. Possible configurations of such a shaped body include but are not limited to pellets, pills, spheres, granules and extrudates, and the like. Alternatively, such compositions can be deposited or coated on or otherwise coupled to a substrate such as but not limited to a porous support. Such a composition can then be used as a means of storing gas, by exposing the composition to a gas and allowing the MOF of the composition to uptake gas.

A number of inorganic compounds known in the art can be used as binders. Non-limiting examples include titanium dioxide, hydrated titanium dioxide, hydrated alumina or other aluminum-containing binders, mixtures of silicon and aluminum compounds, silicon compounds, clay minerals, alkoxysilanes, and amphiphilic substances. Other binders are in principle all compounds used to date for the purpose of achieving adhesion in powdery materials. Compounds, in particular oxides, of silicon, of aluminum, of boron, of phosphorus, of zirconium and/or of titanium are preferably used. Of particular interest as a binder is silica, where the $SiO_2$ may be introduced into the shaping step as a silica sol or in the form of tetraalkoxysilanes. Oxides of magnesium and of beryllium and clays, for example montmorillonites, kaolins, bentonites, halloysites, dickites, nacrites and anauxites, may furthermore be used as binders. Specific examples include tetramethoxysilane, tetraethoxysilane, tetrapropoxysilane and tetrabutoxysilane, the analogous tetraalkoxytitanium and tetraalkoxyzirconium compounds and trimethoxy-, triethoxy-, tripropoxy- and tributoxy-aluminum. The binder may have a concentration of from 0.1 to 20% by weight. Alternatively, no binder is used.

In addition, organic viscosity-enhancing substances and/or hydrophilic polymers, e.g. cellulose or polyacrylates can be used. The organic viscosity-enhancing substance used may likewise be any substance suitable for this purpose. Those preferred are organic, in particular hydrophilic polymers, e.g., cellulose, starch, polyacrylates, polymethacrylates, polyvinyl alcohol, polyvinylpyrrolidone, polyisobutene and polytetrahydrofuran.

There are no restrictions with regard to the optional liquid which may be used to create a paste-like composition of the MOFs disclosed herein. In addition to water, alcohols may be used. Accordingly, both monoalcohols of 1 to 4 carbon atoms and water-miscible polyhydric alcohols may be used. In particular, methanol, ethanol, propanol, n-butanol, isobutanol, tert-butanol and mixtures of two or more thereof are used.

Amines or amine-like compounds, for example tetraalkylammonium compounds or aminoalcohols, and carbonate-containing substances, such as calcium carbonate, may be used as further additives in the disclosed compositions. Such further additives are described in EP-A 0 389 041, EP-A 0 200 260 and WO 95/19222, which are incorporated fully by reference in the context of the present application.

Most, if not all, of the additive substances mentioned above may be removed from such a composition by drying or heating, optionally in a protective atmosphere or under vacuum. In order to keep the MOF intact, the composition is preferably not exposed to temperatures exceeding 300° C. Heating/drying the composition under the mild conditions, in particular drying in vacuo, preferably well below 300° C., is sufficient to at least remove organic compounds out of the pores of the MOF. Generally, the conditions are adapted and chosen depending upon the additive substances used.

The order of addition of the components (optional solvent, binder, additives, MOF material) is not critical. It is possible either to add first the binder, then, for example, the MOF material and, if required, the additive and finally the mixture containing at least one alcohol and/or water or to interchange the order with respect to any of the aforementioned components.

Generally, as would be understood by those skilled in the art, MOFs based upon the present inorganic metal center and organic linker/ligand block components can be prepared by known solvothermal methods, as follows. A ligand component is mixed with a metal salt (e.g., a metal nitrate) corresponding to a desired metal center (e.g., a transition metal) in a molar proportion of about 1:n, where n is greater than or equal to 1, in an organic solvent or mixture of organic solvents, such as dimethylformamide, diethylformamide, ethanol, isopropanol, methanol, butanol, or pyridine. The mixture is reacted until crystalline material is formed. Then, the solvent is decanted, and the resulting MOF is collected and washed one or several times with organic solvent to afford the desired MOF material. As described above, an MOF can then be further modified by removing coordinated solvent molecules under elevated temperature and reduced pressure. Confirmation of removal of all solvent molecules from the MOF can be confirmed via elemental analysis.

More specifically, regarding the synthesis of MOF-#1, a molar excess of a metal salt precursor of metal center $Cu_2$ and a combination of dinitrile-terminated, ethyl-substituted cubane and N,N-dicarboxyphenyl-, ethyl-substituted arylene diimide linker/ligand components (see components 31 and 35 of FIG. 3) are mixed in a suitable solvent, such as DMF, with subsequent introduction of ethanol and/or HCl. After reaction at elevated temperatures for up to about 24 hours or more, MOF-#1 material is isolated. (Reference is made to the synthesis of NOTT-107, above.)

Likewise, with reference to the synthesis of MOF-#20, a molar excess of a metal salt precursor of metal center $Zn_2$ and a combination of ethyl-substituted naphthalene dicarboxylate and ethyl-substituted dinitrile linker/ligand components (see, components 19 and 25 of FIG. 3) are mixed in a suitable solvent, such as DMF, with subsequent introduction of ethanol and/or HCl. After reaction at elevated temperatures for up to 24 hours or more, MOF-#20 material is isolated. (Reference is, again, made to the synthesis of NOTT-107, above.)

Figure 18A:
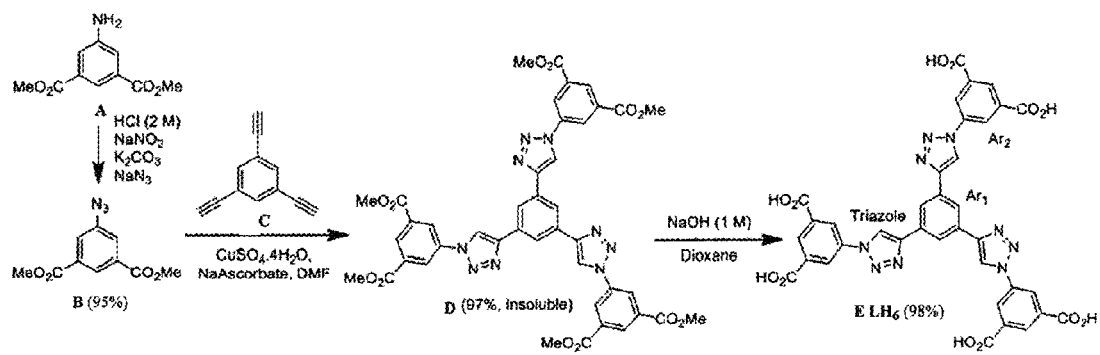
FIGS. 18A-B provide, in accordance herewith, (A) a schematic synthesis of the triazolyl ligand 5,5',5"-(4,4',4"-(benzene-1,3,5-triyl)tris(1H-1,2,3-triazole-4,1-diyl))triisophthalic acid (and salts thereof), as can be used (B) in the generation and synthesis of one or more metal organic frameworks of the inventive subject matter, with a representative metal center.

Regarding metal organic framework NU-125, a synthesis for the triazolyl ligand E ($LH_6$) is schematically presented in FIG. 18A. Compound A (20 g, 95.6 mmol) was dissolved in aqueous HCl (2 M, 1 l) in a 2 L round bottom flask equipped with a magnetic stir bar. The flask was cooled on an ice bath to 0 C and aqueous $NaNO_2$ (8.57 g, 124 mmol, dissolved in 100 ml $H_2O$) was added slowly to this solution. Reaction mixture was stirred for 30 minutes and neutralized using $K_2CO_3$. Then, aqueous $NaN_3$ (14 g, 215 mmol, dissolved in 100 ml $H_2O$) was added slowly to the mixture and the solution was stirred for additional 20 min. Then, reaction mixture was filtered and washed with $H_2O$. Remaining precipitate was dissolved in $CH_2Cl_2$ and filtered and filtrate was evaporated giving orange solid, which was redissolved in a minimum amount of $CH_2Cl_2$, and column chromatographed over silica gel using $CH_2Cl_2$ to give B as a white solid, which was dried under high vacuum. Yield=20.1 g (95%). $^1$H NMR (500 MHz, $CDCl_3$): δ 3.94 (s, 6H, —$CO_2CH_3$), 7.82 (d, J=1.5 Hz, 2H, Ar—H), 8.40 (t, J=1.5 Hz, 1H, Ar—H). $^{13}$C NMR (126 MHz, $CDCl_3$): δ 52.74, 124.09, 126.94, 132.32, 141.31, and 165.45.

1,3,5-acetylenebenzene (C, 1.75 g, 11.7 mmol), compound B (10 g, 45.2 mmol), $CuSO_4.4H_2O$ (10 g, 45.2 mmol), and sodium ascorbate (10 g, 45.2 mmol) were added in 1 L Schlenk flask equipped with a magnetic stir bar and a rubber stopper. The mixture was taken into a drybox and dry DMF (600 ml) was added into this solution. The solution was capped and taken out of drybox then stirred for 24 h at 90° C., giving a pinkish solution with large amount of precipitate. This suspension was filtered and the precipitate was washed with successively with DMF (300 ml), $H_2O$ (300 ml), and acetone (300 ml). Remaining solid was collected and dried under high vacuum to give the product D as off white solid. Yield 9.9 g (97%). Product is very insoluble so NMR spectra could not be collected. Isolated product was used in the following step without further purification.

Compound D (9.6 g, 11.2 mmol) is dissolved in Dioxane (100 ml) in 2 L round bottom flask equipped with a magnetic stir bar. Then, NaOH (800 ml, 3.13 M aqueous solution, 2.5 mol) added to this solution, which turned into a suspension. This suspension is refluxed for 48 h at 100° C. until it become clear. Dioxane was removed using rotary evaporator and the remaining aqueous solution was acidified to pH 2 using concentrated HCl (200 mL of a 37% aqueous solution). The resulting precipitate was collected via centrifugation (6500 rpm), washed with $H_2O$ (200 mL), and dried under high vacuum to afford E ($LH_6$) as off white solid. Yield=8.5 g (98%). $^1$H NMR (500 MHz, DMSO-$d_6$): 8.52 (s, 3H, $Ar_2$—H), 8.58 (s, 3H, $Ar_1$—H), 8.70 (s, 6H, $Ar_2$—H), 9.68 (s, 3H, Triazole-H). $^{13}$C NMR (126 MHz, DMSO-$d_6$): δ 119.6, 121.71, 123.14, 129.20, 131.04, 132.94, and 165.55.

Figure 18B:
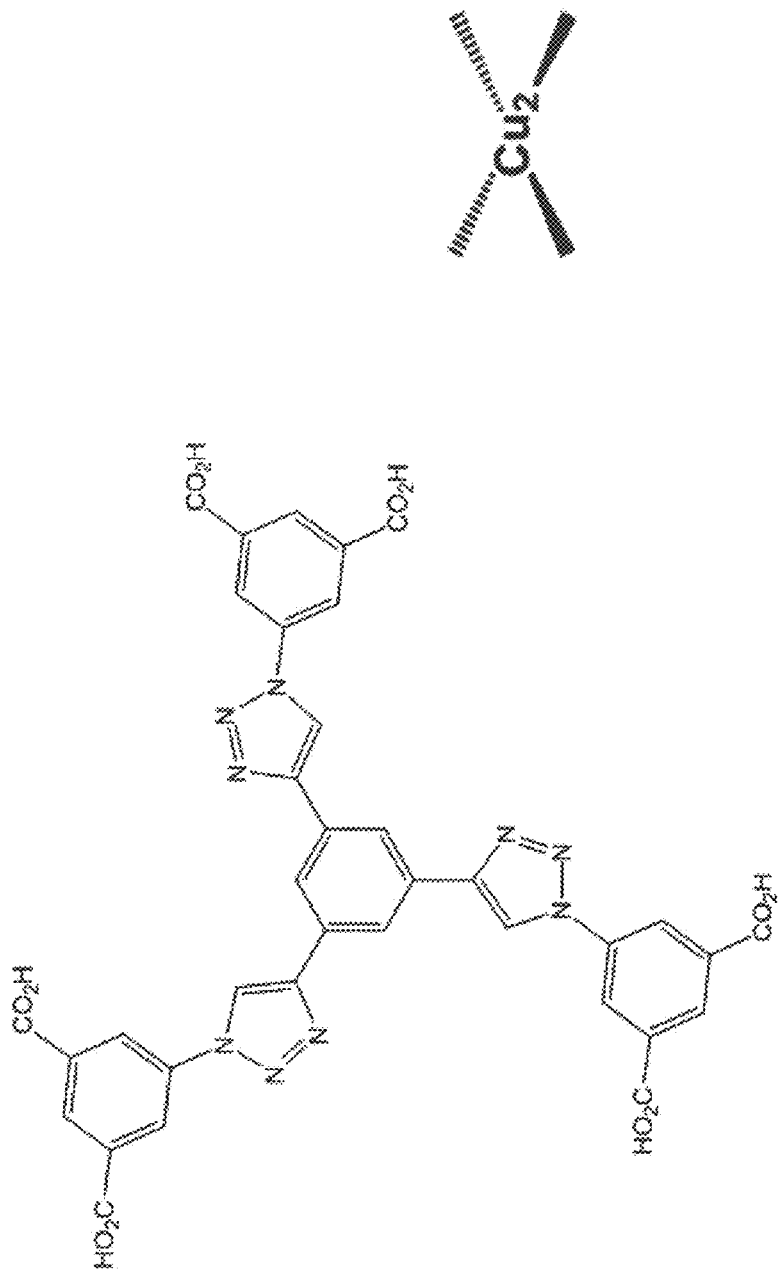

Regarding the synthesis of NU-125, reference is made to FIG. 18B. A mixture of $Cu(NO_3)_2.2.5H_2O$ (1.00 g) and 5,5',5"-(4,4',4"-(benzene-1,3,5-triyl)tris(1H-1,2,3-triazole-4,1-diyl))triisophthalic acid (Ligand E, above, 0.40 g) was dissolved in a mixture of DMF (100 mL) in a 250 ml jar. Then 50 drops of conc. $HBF_4$ were added to the solution and mixed well. The jar was capped and placed into an oven at 80° C. for 24 h. The resulting teal crystalline powder was combined and washed with DMF.

Prior to drying, DMF-solvated MOF NU-125 was soaked in ethanol, replacing the soaking solution every 24 h for 3 days. After soaking, the ethanol-containing samples were placed inside the supercritical $CO_2$ dryer and the ethanol was exchanged with $CO_2$(liq.) over a period of 10 h. During this time the liquid $CO_2$ was vented under positive pressure for three minutes every two hours. The rate of venting of $CO_2$ (liq.) was always kept below the rate of filling so as to maintain a full drying chamber. Then the chamber was sealed and the temperature was raised to 38° C. (i.e., above the critical temperature for carbon dioxide), at which time the chamber was slowly vented over the course of 15 h. The color of the MOF changed from teal to dark blue. The collected MOF sample was then stored inside an inert-atmosphere glovebox until further analysis.

Figure 19B:
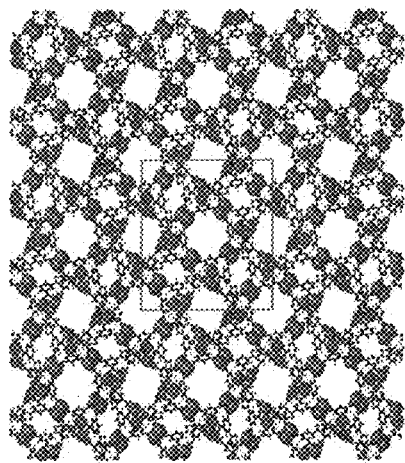
FIGS. 19A-C provide experimental crystal structures of a non-limiting representative metal organic framework of the inventive subject matter, NU-125.
Figure 19C:
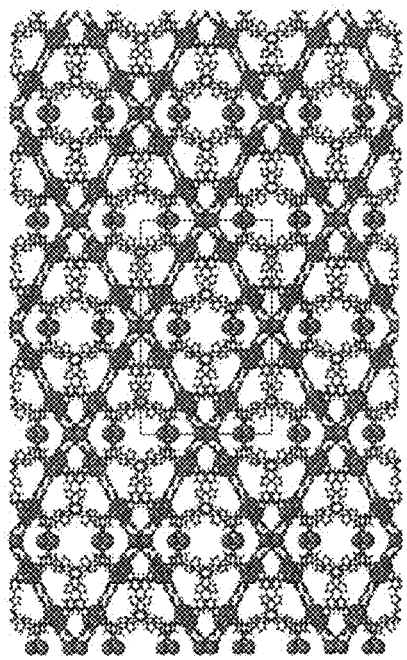
Figure 19A:
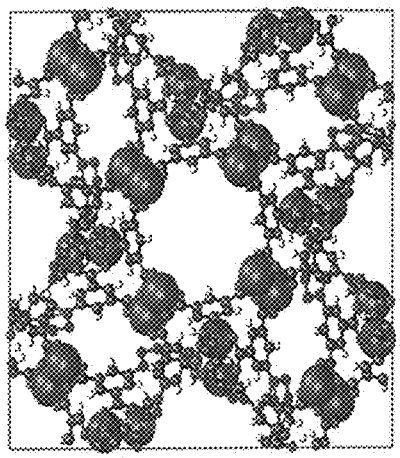
Figure 20:
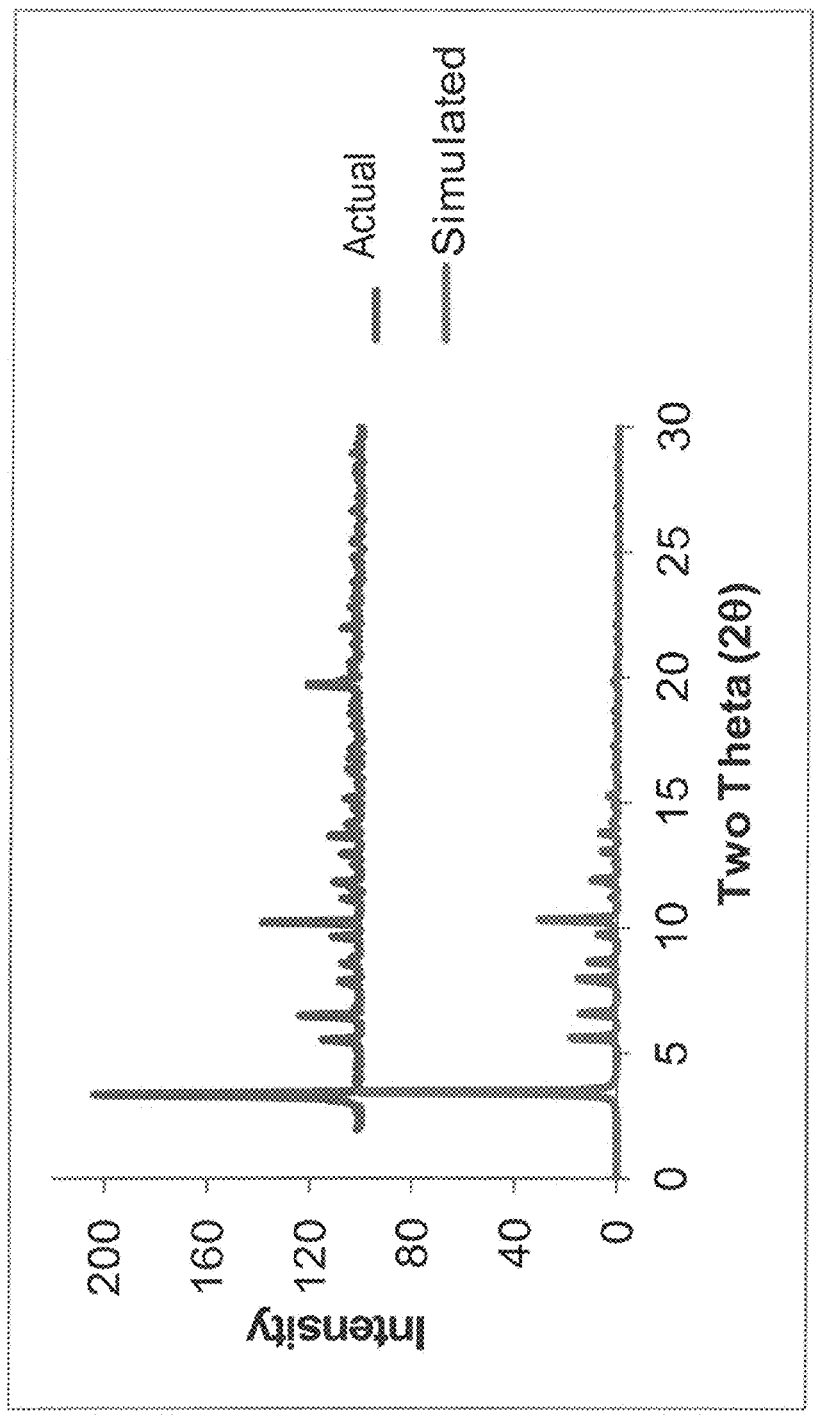
FIG. 20 compares simulated and actual PXRD patterns of NU-125.

Prior to sorption measurements, the sample was evacuated at room temperature for two hours, then brought to 110° C. over four hours. XRD data were used to generate corresponding crystal structures (FIGS. 19A-C) and provide a unit cell formula of $C_{576}H_{240}N_{144}O_{192}Cu_{48}$ with a density (calcd) of 0.578 g/cm$^3$. Crystal data is summarized in Table 3, below. The values for the cell parameters (angles alpha, beta, and gamma; spacings a, b, and c in Angstrom) represent the space group shown. PXRD analysis of synthesized NU-125 provided a diffraction pattern (FIG. 20) conforming to that simulated by and thereby validating the methods and systems of the inventive subject matter.

TABLE 3

Summary of Crystal Data for NU-125

| | |
|---|---|
| symmetry_space_group_name_H-M | 'P1' |
| _symmetry_cell_setting | triclinic |
| _symmetry_equiv_pos_as_xyz | x, y, z |
| _cell_length_a | 31.3109 |
| _cell_length_b | 31.3109 |
| _cell_length_c | 44.8070 |
| _cell_angle_alpha | 90.0000 |
| _cell_angle_beta | 90.0000 |
| _cell_angle_gamma | 90.0000 |

Figure 21:
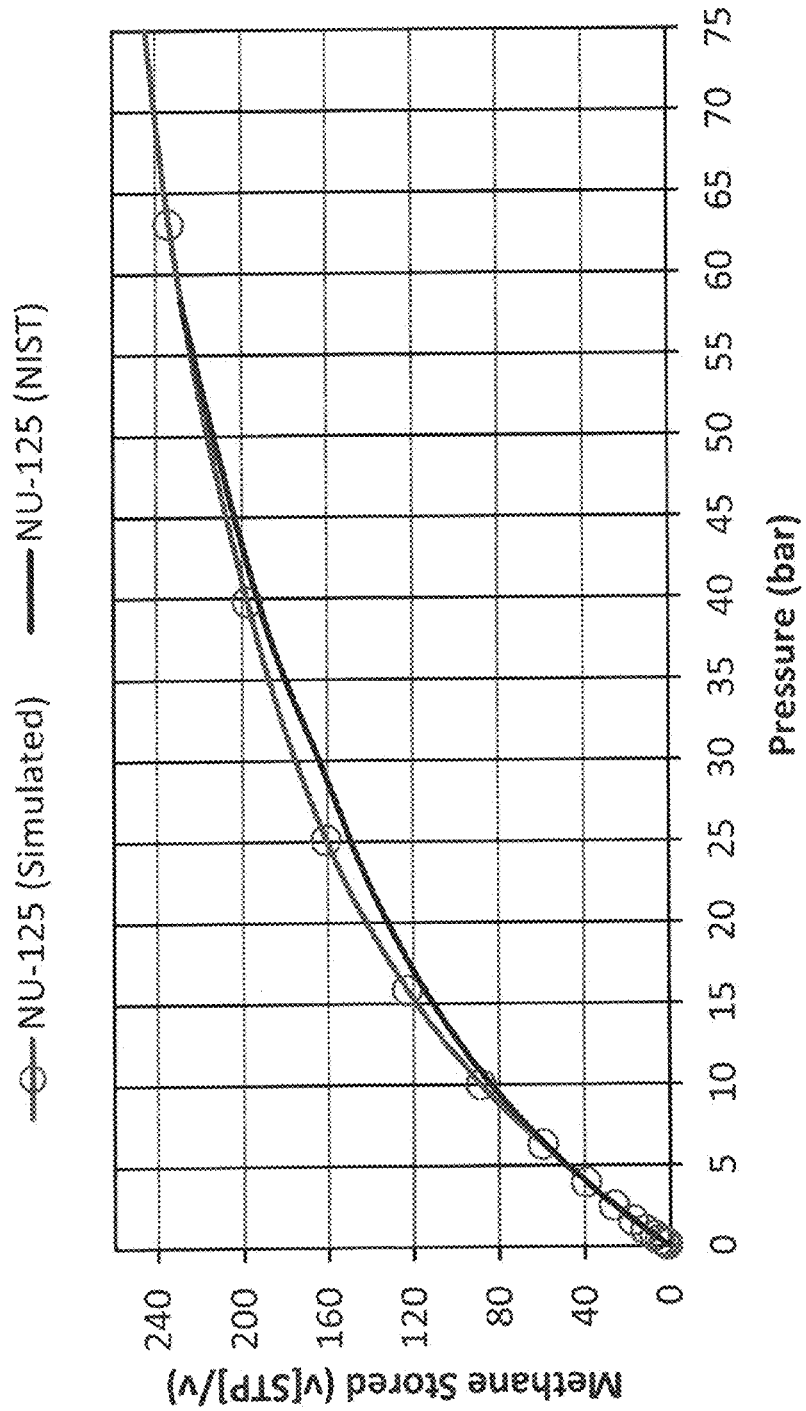
FIG. 21 shows methane sorption measurements, per the National Institute of Standards and Technology (NIST) and, by comparison, methane sorption simulated by the inventive subject matter.

Methane adsorption measurements for NU-125 were taken as described elsewhere herein. FIG. 21 compares storage predicted (simulated) with NIST measurements, confirming that metal organic framework of NU-125 achieves parity with compressed natural gas (CNG) storage (~240v[STP]/v) at ~65 bar.

Figure 22:
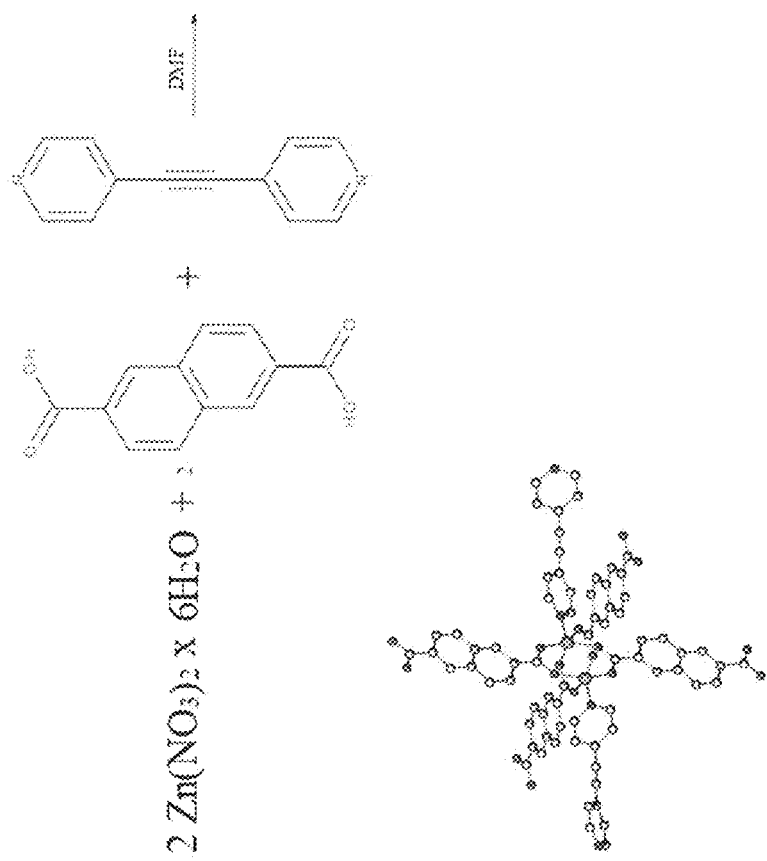
FIG. 22 provides a schematic synthesis of a representative non-limiting metal organic framework of the inventive subject matter, wMOF-1.

Regarding the synthesis of wMOF-1 and with reference to FIG. 22, a mixture of $Zn(NO_3)_2 \times 6H_2O$ (1.00 g) and 2,6-naphthalenedicarboxylic acid (0.728 g) was sonicated in DMF (50 mL) in a 250 ml conical flask until solution became clear. Then a solution of 1,2-di(4-pyridyl)acetylene (0.303 g) in DMF (10 mL) was added and resulting mixture was sonicated for additional 5 min. The mother solution was divided into 4 capped 8-dram vials and placed into an oven at 80° C. for 24 h. The resulting colorless rectangular shaped crystals were combined and washed with DMF.

Prior to drying, DMF-solvated wMOF-1 was soaked in ethanol, replacing the soaking solution every 24 h for 3 days. After soaking, the ethanol-containing samples were placed inside the supercritical CO2 dryer and the ethanol was exchanged with CO2(liq.) over a period of 10 h. During this time the liquid CO2 was vented under positive pressure for three minutes every two hours. The rate of venting of CO2 (liq.) was always kept below the rate of filling so as to maintain a full drying chamber. Then the chamber was sealed and the temperature was raised to 38° C. (i.e., above the critical temperature for carbon dioxide), at which time the chamber was slowly vented over the course of 15 h. The collected MOF sample was then stored inside an inert-atmosphere glovebox until further analysis.

Figure 23:
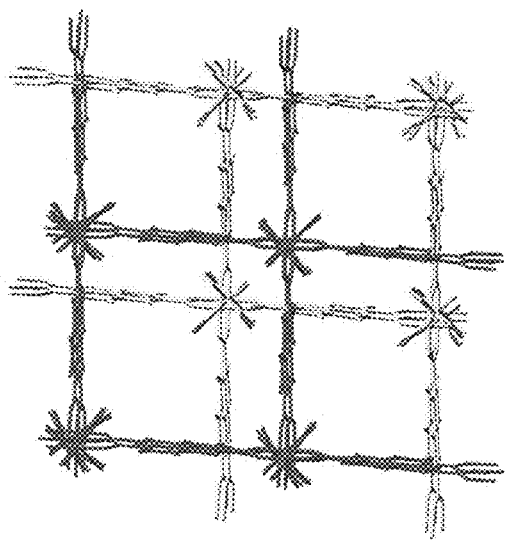
FIG. 23 provides experimental crystal structures of wMOF-1.
Figure 24:
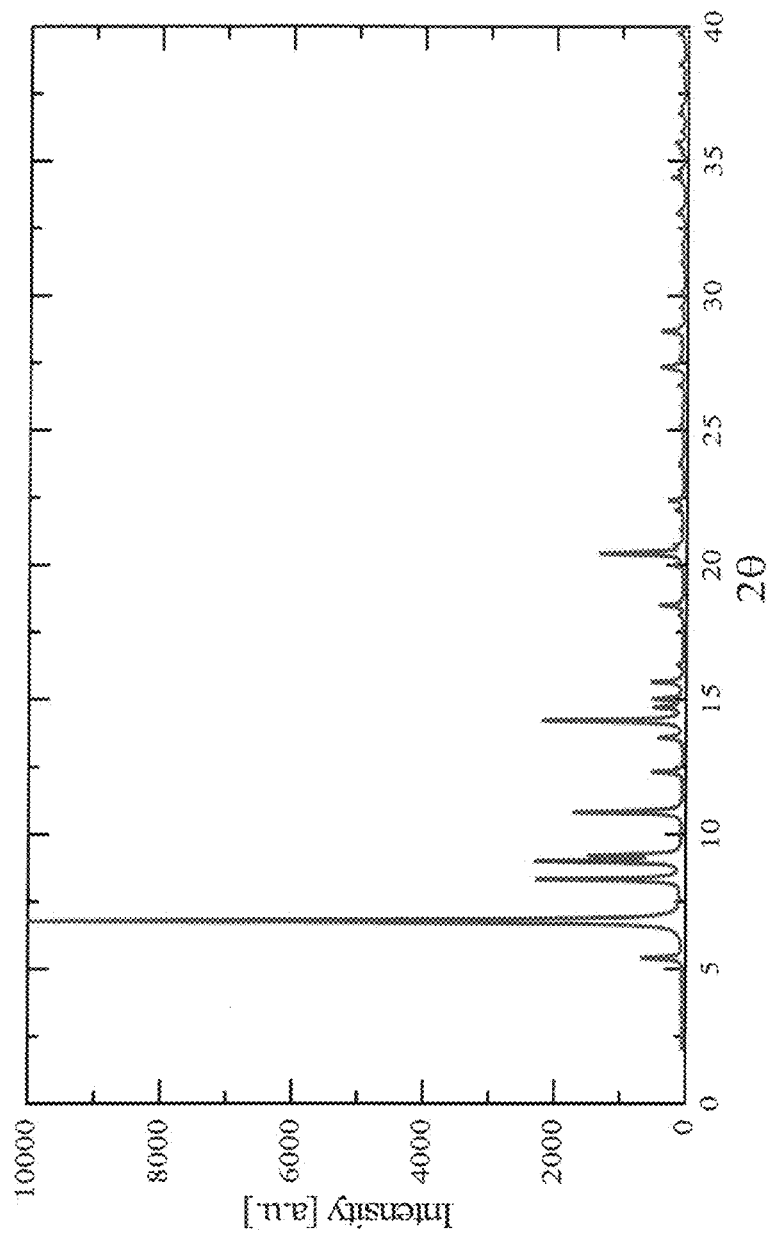
FIG. 24 provides a simulated PXRD pattern of wMOF-1, in accordance with the inventive subject matter.
Figure 25:
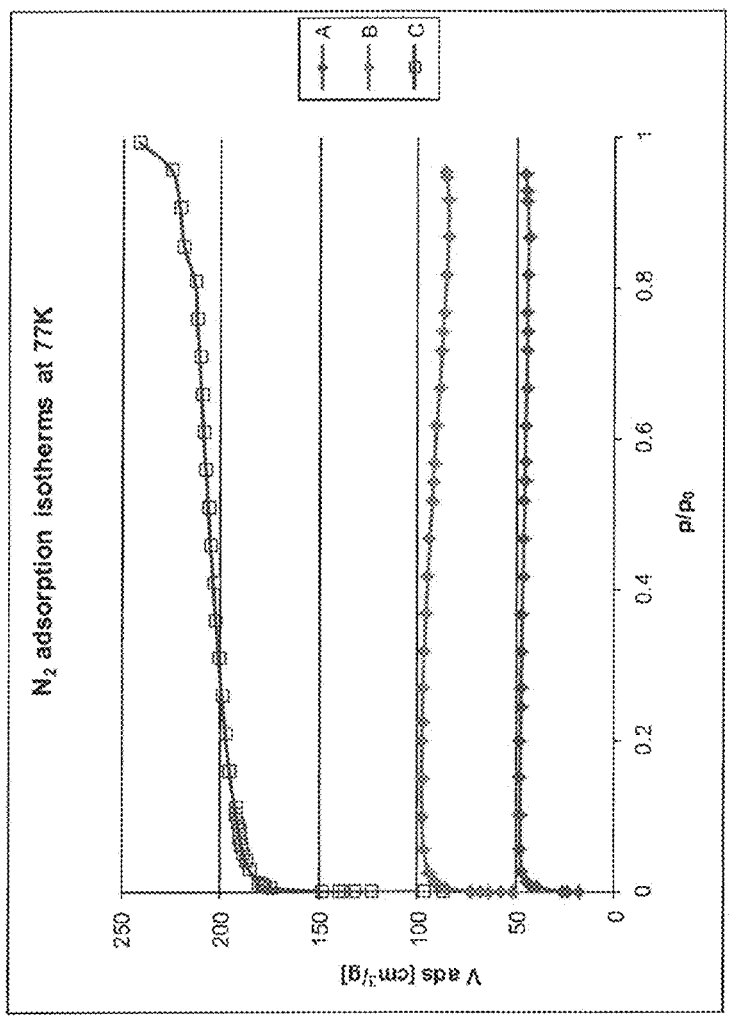
FIG. 25 shows BET surface area measurements for wMOF-1.

Prior to sorption measurements, the sample was evacuated at room temperature for one hour. XRD data was used to generate the crystal structure shown in FIG. 23 and provide a unit cell formula of $C_{576}H_{320}N_{32}O_{128}Zn_{32}$ with a density (calcd) of 0.878 g/cm$^3$. Crystal data is summarized in Table 4, below. The values for the cell parameters (angles alpha, beta, and gamma; spacings a, b, and c in Angstrom) represent the space group shown. The PXRD diffraction pattern (simulated) for wMOF-1 is provided in FIG. 24. BET surface area measurements for the metal organic framework of wMOF were taken as described elsewhere herein. FIG. 25 shows comparative N$_2$ adsorption isotherms.

TABLE 4

Summary of Crystal Data for wMOF-1.

| | |
|---|---|
| _symmetry_space_group_name_H-M | 'P1' |
| _symmetry_cell_setting | triclinic |
| _symmetry_equiv_pos_as_xyz | x, y, z |
| _cell_length_a | 26.2067 |
| _cell_length_b | 26.2067 |
| _cell_length_c | 32.8534 |
| _cell_angle_alpha | 94.2596 |
| _cell_angle_beta | 94.2596 |
| _cell_angle_gamma | 94.0435 |

Metal organic frameworks of this invention, such as but not limited to NU-125 and wMOF-1, can be incorporated into a container, as discussed elsewhere herein. For instance, NU-125 powder or a related material is placed in a container before closure. One or more gases are then introduced from an external supply source, through an inlet component using techniques understood by those skilled in the art. Such a gas includes but is not limited to those disclosed elsewhere herein. In accordance with this inventive subject matter, under a given pressure, considerably more gas (e.g., methane), is stored in a container, as compared to a container of essentially the same volume absent a metal organic framework of the inventive subject matter.

The preceding, non-limiting examples and data illustrate various aspects and features relating to the MOFs, compositions and/or methods of one or more embodiments of the inventive subject matter described herein. While the utility of one or more embodiments of this inventive subject matter is illustrated through the use of several MOF compounds/compositions and block components and groups and/or moieties thereof which can be used in MOF synthesis, it will be understood by those skilled in the art that comparable results are obtainable with various other MOFs/compositions and block components/groups/moieties, as are commensurate with the scope of one or more embodiments of the inventive subject matter, including the building block components illustrated in FIG. 3. Accordingly, any such MOF and/or composition comprising an MOF can be prepared according to procedures of the sort described herein or would otherwise be understood by those skilled in the art, such MOFs/compositions limited only by available metal center block, linker/ligand and substituent group components, such components as are commercially-available or can be prepared with suitable precursors through synthetic procedures known in the art. Regardless, such MOF compounds and related compositions can be prepared using procedures of the sort described in U.S. Pat. Nos. 7,824,473, 7,862,647, and 7,744,842—each of which, together with the references cited therein, is incorporated herein by reference in its entirety.

Nonetheless, with respect to the compounds, compositions and/or methods of one or more embodiments of the inventive subject matter, such MOF compounds can suitably comprise, consist of, or consist essentially of any of the aforementioned metal center components, linker/ligand components and moieties and/or functional/substituent groups thereof. Each such compound, component or moiety/group thereof is compositionally distinguishable, characteristically contrasted and can be utilized in conjunction with one or more embodiments of the inventive subject matter separate and apart from another. Accordingly, it should be understood that the inventive compounds, compositions and/or methods, as illustratively disclosed herein, can be practiced or utilized in the absence of any one compound, component or moiety/group thereof and/or step, such compound, component, moiety/group and/or step which may or may not be specifically disclosed, referenced or inferred herein, the absence of which may or may not be specifically disclosed, referenced or inferred herein.

In one or more embodiments, a container for up-taking, storing and/or releasing at least one gas is provided, such a container as can comprise at least one of an inlet component and an outlet component, a pressure control component to maintain such a gas under pressure within such a container, and a metal organic framework material comprising a metal organic framework (MOF) of the inventive subject matter, and optionally a gas. Such a gas or gases can be under a pressure up to about 10 bar, up to about 50 bar, up to about 100 bar or up to about 200 bar or more inside such a container. As discussed elsewhere herein, such a container can comprise a porous metal organic framework material comprising a metal center component and one or more linker/ligand components of the sort described herein coupled with or coordinated to such a metal center component. In certain embodiments, one or more such containers can be incorporated with a gas storage system and/or a gas delivery system. In certain other embodiments, one or more such containers can be incorporated with a fuel cell. Regardless, such a container and/or system can be used in conjunction with a fuel cell and/or fuel tank for supplying power to stationary and/or mobile and/or mobile portable applications such as but not limited to power plants, automotive vehicles (e.g., without limitation, cars, trucks and buses) and cordless power tools. For example, the container may include a MOF that stores a gas used to power one or more devices. Such a container may be a fuel cell (e.g., a device that uses an electrochemical reaction involving the stored gas to produce energy for powering one or more devices), a fuel tank (e.g., a chamber that stores the gas for supply to a device that consumes the gas for generating energy and/or power), and the like.

The volume of such a container can be a matter of choice and adapted to the specific needs of the respective application for which such a container is used. For purpose of non-limiting examples, the volume of such a container, as can be used with a fuel cell on a passenger car, can be about 300 l or less. In certain such embodiments, the volume of such a container can be about 150 l or about 100 l or less. Alternatively, such a container used with a fuel cell of a truck, can be about 500 l or less. In certain other embodiments, the volume of such container can be about 400 l or about 300 l or less. Regardless, any such container can be, for instance, used in conjunction with a gas storage or gas delivery system—for example, as in a gas station where the volume of such a container may be within the aforementioned parameters, but may well exceed such volumes.

As would be understood by those skilled in the art, the geometry or configuration of such a container can be cylindrical. Nonetheless, such containers relating to the inventive subject matter can comprise a non-cylindrical geometry or configuration. Accordingly, a non-cylindrical container, together with related storage systems and/or fuel cells can have a geometry or configuration adapted to a particular end-use application. For example, in automotive vehicles, a space or cavity otherwise unusable can be occupied with a container, storage system and/or fuel cell of the inventive subject matter.

Regardless of geometry or configuration, a container of the inventive subject matter can be manufactured from a material stable when exposed to pressures of the sort discussed above. Materials can vary depending upon a gas(es) to be uptaken and/or stored and/or released. Such materials include but are not limited to stainless steel and aluminum, together with various synthetic materials composite materials, fiber reinforced synthetic materials, fiber reinforced composite materials, carbon fiber composite materials and combinations thereof, the manufacture thereof as would be known to those skilled in the art made aware of the inventive subject matter. Without limitation, such containers can be designed and constructed to meet one or more recognized standards, in particular, such containers can meet ISO 11439 and/or NGV2 standards for natural gas storage and use in conjunction with automotive vehicles, each such standard as is incorporated herein by reference in its entirety.

In one embodiment, a system for generating and/or screening one or more potential metal-organic frameworks (MOFs) is provided. The system includes a generation module that is configured to receive identifications of building blocks for determining if the building blocks can be used to form one or more of the potential MOFs. The generation module is further configured to determine which of the potential MOFs that can be formed by simulating a combining of the building blocks in different arrangements.

In another aspect, the system also includes a fabrication system coupled with the generation module. The fabrication system includes one or more sources of actual building blocks that are identified for the generation module. The fabrication system is configured to automatically combine the actual building blocks that are used to form the potential MOFs as simulated by the generation module.

In another aspect, the building blocks include inorganic building blocks, organic building blocks, and functional groups.

In another aspect, the generation module is configured to connect the inorganic building blocks with the organic building blocks.

In another aspect, the generation module is configured to simulate the combining of the building blocks that are identified based on at least one of topological information or geometrical information assigned to the building blocks.

In another aspect, the generation module is configured to determine whether two or more of the building blocks that are identified cannot be combined with each other without resulting in collisions between atoms of the building blocks in the simulating of the combining of the building blocks.

In another aspect, the system also includes an evaluation module configured to calculate one or more material properties of the potential MOFs.

In another aspect, the one or more material properties include one or more of surface area, pore volume, pore size distribution, powder x-ray diffraction pattern, or adsorption capability.

In another aspect, the evaluation module is configured to perform an atomistic grand Monte Carlo simulation to calculate at least one of the one or more material properties.

In one embodiment, a method for generating and/or screening one or more potential metal-organic frameworks (MOFs) is provided. The method includes receiving building blocks used to form one or more of the potential MOFs, determining which of the potential MOFs that can be formed by simulating a combining of different arrangements of the building blocks, and outputting an identification of the potential MOFs that can be formed from the building blocks based on the simulating of the combining of the building blocks.

In another aspect, the method also includes outputting instructions to a fabrication system for automatically creating one or more of the potential MOFs from one or more sources of the building blocks.

In another aspect, the building blocks include inorganic building blocks, organic building blocks, and functional groups.

In another aspect, determining which of the potential MOFs can be formed includes combining the building blocks based on at least one of topological information or geometrical information assigned to the building blocks.

In another aspect, the method also includes calculating one or more material properties of the potential MOFs.

In another aspect, the one or more material properties include surface area, pore volume, pore size distribution, powder x-ray diffraction pattern, or adsorption capability.

In another aspect, calculating the one or more material properties includes performing an atomistic grand Monte Carlo simulation to calculate at least one of the one or more material properties.

In one embodiment, a computer readable storage medium for a system having a processor is provided. The computer readable storage medium includes one or more sets of instructions that are configured to direct the processor to receive an identification of building blocks for one or more of the potential MOFs, determine which of the potential MOFs that can be formed by performing a simulation of combining of the building blocks, and output an identification of the potential MOFs that can be formed from the building blocks based on the building blocks that can be combined with each other in the simulation.

In another aspect, the computer readable storage medium is a tangible and non-transitory computer readable storage medium.

In another aspect, the one or more sets of instructions are configured to direct the processor to automatically direct a fabrication system having one or more sources of the building blocks to create one or more of the potential MOFs.

In another aspect, the building blocks include inorganic building blocks, organic building blocks, and functional groups.

In another aspect, the one or more sets of instructions are configured to direct the processor to combine the inorganic building blocks with the organic building blocks.

In another aspect, the one or more sets of instructions are configured to direct the processor to combine the building blocks based on at least one of topological information or geometrical information assigned to the building blocks.

In another aspect, the one or more sets of instructions are configured to direct the processor to calculate one or more material properties of the potential MOFs.

In another aspect, the one or more material properties include one or more of surface area, pore volume, pore size distribution, powder x-ray diffraction pattern, or adsorption capability.

In another aspect, the one or more sets of instructions are configured to direct the processor to perform an atomistic grand Monte Carlo simulation to calculate at least one of the one or more material properties.

In one embodiment, a metal organic framework (MOF) is provided. The MOF includes a polymeric structure of an inorganic metal center block component; an organic linker block component; and, optionally a solvent, said linker block component comprising a plurality of terminal groups selected from carboxy groups and nitrogenous groups coupled by R, wherein R is selected from a covalent bond and moieties selected from C, arylene moieties, arylene tetracarboxydiimide moieties, fused arylene moieties, fused arylenetetrayl moieties, heteroarylene moieties, di-valent multicyclo moieties, ethynylene moieties and ethenylene moieties and combinations of said moieties coupled one to another.

In another aspect, the MOF is substantially absent a solvent.

In another aspect, a said linker component is substituted with at least one group selected from halo, $C_1$-$C_3$ alkyl, amino, phenyl, hydroxy, cyano, and $C_1$-$C_3$ alkoxy groups and combinations thereof.

In another aspect, the metal of a said metal center block component is selected from a component comprising $Mg2+$, $Ca2+$, $Sr2+$, $Ba2+$, $Sc3+$, $Y3+$, $Ti4+$, $Zr4+$, $Hf4+$, $V4+$, $V3+$, $V2+$, $Nb3+$, $Ta3+$, $Cr3+$, $Mo3+$, $W3+$, $Mn3+$, $Mn2+$, $Re3+$, $Re2+$, $Fe3+$, $Fe2+$, $Ru3+$, $Ru2+$, $Os3+$, $Os2+$, $Co3+$, $C2+$, $Rh2+$, $Rh+$, $Ir2+$, $Ir+$, $Ni2+$, $Ni+$, $Pd2+$, $Pd+$, $Pt2+$, $Pt+$, $Cu2+$, $Cu+$, $Ag+$, $Au+$, $Zn2+$, $Cd2+$, $Hg2+$, $Al3+$, $Ga3+$, $In3+$, $Tl3+$, $Si4+$, $Si2+$, $Ge4+$, $Ge2+$, $Sn4+$, $Sn2+$, $Pb4+$, $Pb2+$, $As5+$, $As3+$, $As+$, $Sb5+$, $Sb3+$, $Sb+$, and $Bi5+$, $Bi3+$, and $Bi+$.

In another aspect, said metal center block component is selected from $Zn_4O$, $Zn_2$, $Cu_2$, $V_3O_3$ and $Zr_6O_6$.

In another aspect, said metal center is $Cu_2$.

In another aspect, the MOF includes nitrogenous linker component

and linker component

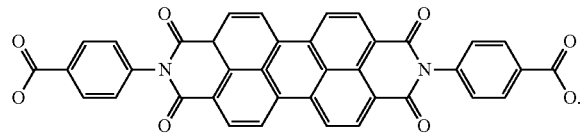

In another aspect, at least one said linker component is substituted with at least one ethyl group.

In another aspect, each said linker component is substituted with a plurality of ethyl groups, and the pore size is about 4-about 8 Å.

In another aspect, said metal center is $Zn_2$.

In another aspect, the MOF includes linker component

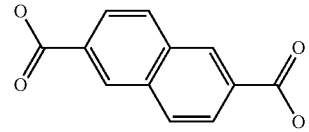 [SMILES: O=C(O)c1ccc2cc(C(=O)O)ccc2c1]

and nitrogenous linker component NC-CN.

In another aspect, at least one said linker component is substituted with at least one ethyl group.

In another aspect, each said linker component is substituted with a plurality of ethyl groups, and the pore size is about 4-about 8 Å.

In another aspect, the MOF is in a composition comprising one or more of a binder, an organic viscosity-enhancing agent and a liquid.

In one embodiment, a metal organic framework (MOF) includes a polymeric crystalline structure comprising the coordination product of a metal component selected from $Zn_4O$, $Zn_2$, $Cu_2$, $V_3O_3$ and $Zr_6O_6$, an organic ligand component selected from the ligands of FIGS. 3B-C and combinations thereof, and optionally a solvent.

In another aspect, said metal component is selected from $Cu_2$ and $Zn_4O$.

In another aspect, the MOF is in a composition comprising one or more of a binder, an organic viscosity-enhancing agent and a liquid.

In another aspect, the MOF is substantially absent a solvent.

In one embodiment, a metal organic framework (MOF) includes a polymeric crystalline structure of a $Cu_2$ metal component, a ligand component of a formula

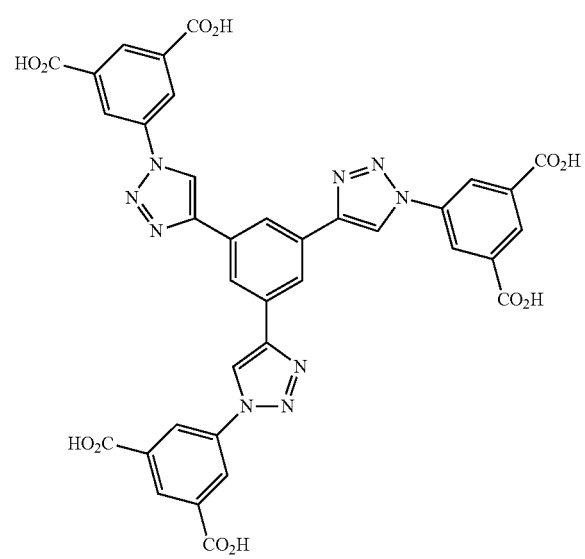 [SMILES: O=C(O)c1cc(C(=O)O)cc(-n2cc(-c3cc(-c4cn(-c5cc(C(=O)O)cc(C(=O)O)c5)nn4)cc(-c4cn(-c5cc(C(=O)O)cc(C(=O)O)c5)nn4)c3)nn2)c1]

and optionally a solvent.

In another aspect, the MOF is substantially absent a solvent.

In another aspect, the MOF is a composition comprising one or more of a binder, an organic viscosity-enhancing agent and a liquid.

In one embodiment, a metal organic framework (MOF) includes a polymeric crystalline structure of a $Zn_4O$ metal component, a first ligand component of a formula

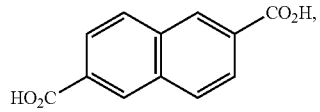

a second ligand component of a formula

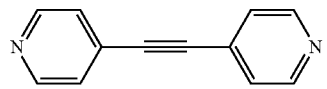

and optionally a solvent.

In another aspect, the MOF is substantially absent a solvent.

In another aspect, the MOF is in a composition comprising one or more of a binder, an organic viscosity-enhancing agent and a liquid.

In another embodiment, a compound of a formula

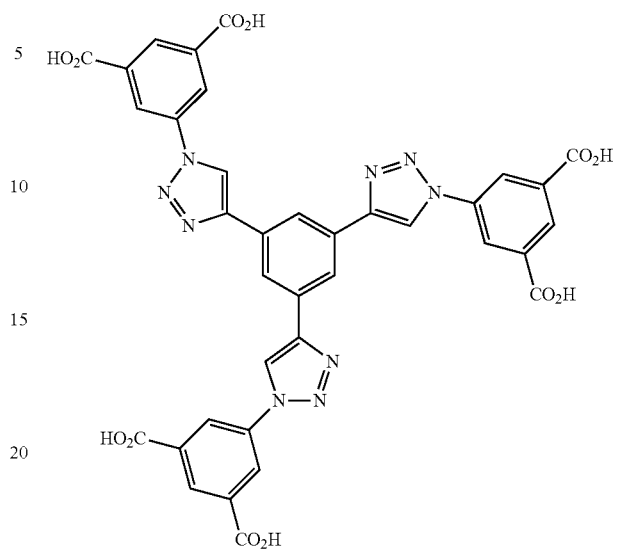

and salts thereof is provided.

In another embodiment, a metal organic framework (MOF) building block comprising a compound of a formula

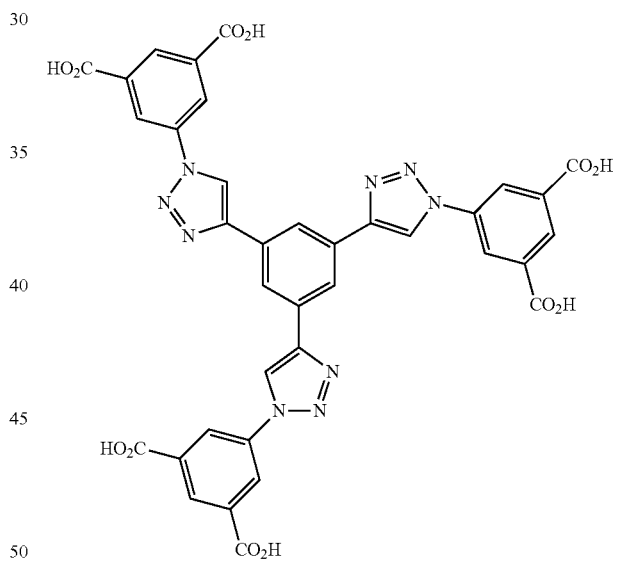

and a metal component is provided.

In another aspect, the metal component is $Cu_2$.

In one embodiment, a method of gas sorption is provided. The method includes providing a metal organic framework (MOF) comprising a polymeric crystalline structure comprising the coordination product of a metal component selected from $Zn_4O$, $Zn_2$, $Cu_2$, $V_3O_3$ and $Zr_6O_6$, an organic ligand component selected from the ligands of FIGS. 3B-C and combinations thereof, and optionally a solvent. The method also includes contacting said MOF and a gas under at least one of a pressure and a temperature sufficient for gas sorption with said MOF.

In another aspect, said gas comprises methane.

In one embodiment, a method of using a metal organic framework (MOF) includes building block comprising a ligand component of a compound of a formula

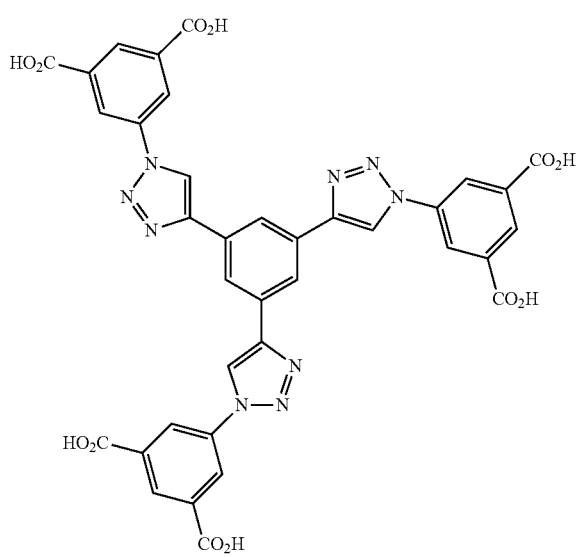 [SMILES: O=C(O)c1cc(C(=O)O)cc(-n2cc(-c3cc(-c4cn(-c5cc(C(=O)O)cc(C(=O)O)c5)nn4)cc(-c4cn(-c5cc(C(=O)O)cc(C(=O)O)c5)nn4)c3)nn2)c1]

and salts thereof for methane storage. The method includes providing a MOF comprising a building block of a compound of a formula

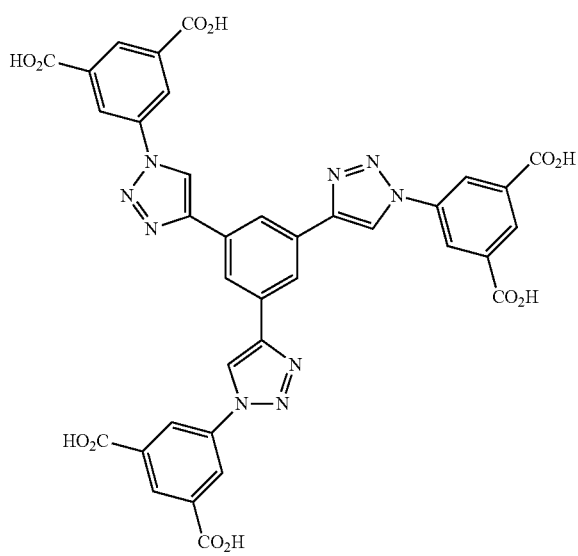 [SMILES: O=C(O)c1cc(C(=O)O)cc(-n2cc(-c3cc(-c4cn(-c5cc(C(=O)O)cc(C(=O)O)c5)nn4)cc(-c4cn(-c5cc(C(=O)O)cc(C(=O)O)c5)nn4)c3)nn2)c1]

and a metal component, and contacting said MOF and methane under at least one of a pressure and a temperature sufficient for methane storage with said MOF.

In another aspect, said metal component of said building block is $Cu_2$.

In another aspect, said methane storage is about 240v [STP]/v at about 65 bar.

In one embodiment, a metal organic framework (MOF) is provided. The MOF comprises a polymeric crystalline structure including the coordination product of a metal component comprising a metal center selected from $Zn_4O$, $Zn_2$, $Cu_2$, $V_3O_3$ and $Zr_6O_6$, an organic ligand component selected from the ligands of FIGS. 3B-C and combinations thereof, and optionally a solvent.

In another aspect, said metal center is selected from $Cu_2$ and $Zn_4O$.

In another aspect, the MOP is in a composition comprising one or more of a binder, an organic viscosity-enhancing agent, and a liquid.

In another aspect, the MOF is substantially absent a solvent.

In another aspect, the embodiment includes a sorbed gas selected from hydrogen, oxygen, nitrogen, the noble gases, acetylene, methane, ethane, propane, natural gases, synthesis gases, carbon monoxide, carbon dioxide, arsine, hydrogen selenide, and combinations thereof.

In another aspect, the embodiment includes sorbed natural gas.

In one embodiment, a metal organic framework (MOF) is provided that includes a polymeric crystalline structure of a $Cu_2$ metal component, a ligand component of a formula

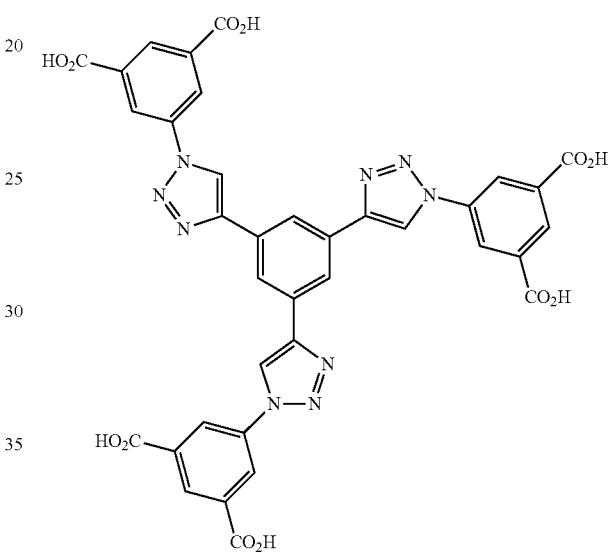

and optionally a solvent.

In another aspect, the MOF is substantially absent a solvent.

In another aspect, the MOF is in a composition comprising one or more of a binder, an organic viscosity-enhancing agent, and a liquid.

In another aspect, the embodiment includes a sorbed gas selected from hydrogen, oxygen, nitrogen, the noble gases, acetylene, methane, ethane, propane, natural gases, synthesis gases, carbon monoxide, carbon dioxide, arsine, hydrogen selenide, and combinations thereof.

In another aspect, the embodiment includes sorbed natural gas.

In another embodiment, a metal organic framework (MOF) is provided that includes a polymeric crystalline structure of a $Zn_4O$ metal component, a first ligand component of a formula

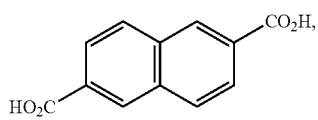 [SMILES: O=C(O)c1ccc2cc(C(=O)O)ccc2c1]

a second ligand component of a formula

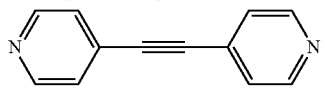

and optionally a solvent.

In another aspect, the MOF is substantially absent a solvent.

In another aspect, the MOF is in a composition comprising one or more of a binder, an organic viscosity-enhancing agent, and a liquid.

In one embodiment, a compound of a formula

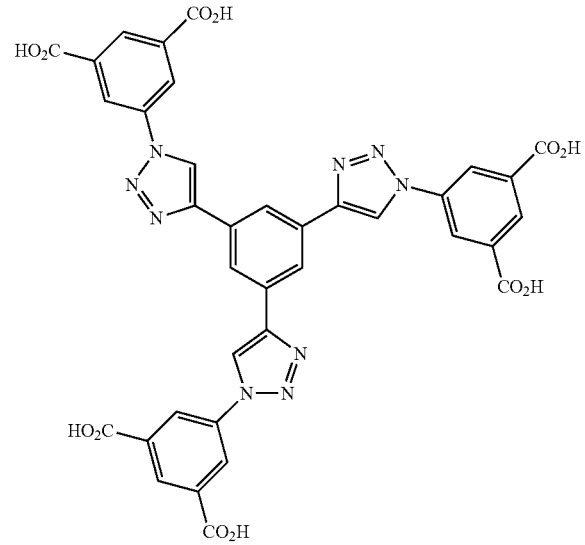 [SMILES: O=C(O)c1cc(C(=O)O)cc(-n2cc(-c3cc(-c4cn(-c5cc(C(=O)O)cc(C(=O)O)c5)nn4)cc(-c4cn(-c5cc(C(=O)O)cc(C(=O)O)c5)nn4)c3)nn2)c1]

and salts thereof is provided.

In one embodiment, a metal organic framework (MOF) building block is provided that includes a compound of a formula

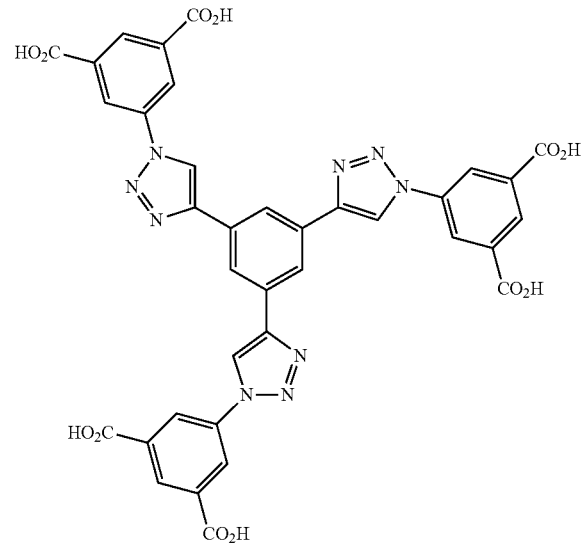 [SMILES: O=C(O)c1cc(C(=O)O)cc(-n2cc(-c3cc(-c4cn(-c5cc(C(=O)O)cc(C(=O)O)c5)nn4)cc(-c4cn(-c5cc(C(=O)O)cc(C(=O)O)c5)nn4)c3)nn2)c1]

and a metal component.

In another aspect, said metal component is $Cu_2$.

In one embodiment, a method of gas sorption is provided. The method includes providing a metal organic framework (MOF) that includes a polymeric crystalline structure comprising the coordination product of a metal component comprising a metal center selected from $Zn_4O$, $Zn_2$, $Cu_2$, $V_3O_3$ and $Zr_6O_6$, an organic ligand component selected from the ligands of FIGS. 3B-C and combinations thereof, and optionally a solvent. The method also includes contacting said MOF and a gas under at least one of a pressure and a temperature sufficient for gas sorption with said MOF.

In another aspect, the MOF includes comprising a sorbed gas selected from hydrogen, oxygen, nitrogen, the noble gases, acetylene, methane, ethane, propane, natural gases, synthesis gases, carbon monoxide, carbon dioxide, arsine, hydrogen selenide, and combinations thereof.

In another aspect, the MOF includes sorbed natural gas.

In another aspect, said gas comprises methane.

In one embodiment, a method of using a metal organic framework (MOF) building block comprising a ligand component of a formula

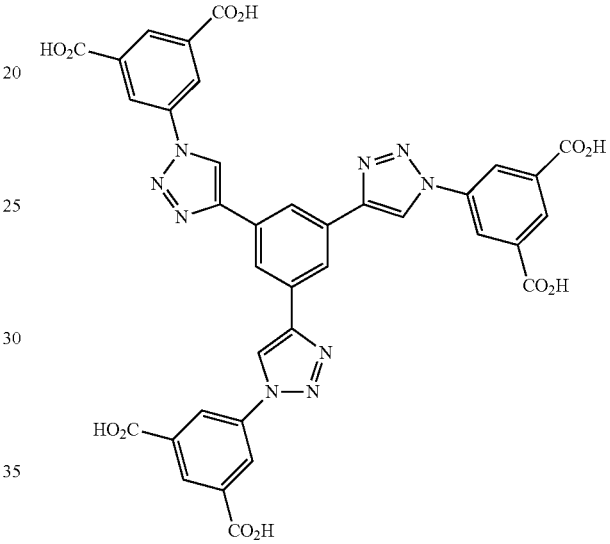

and salts thereof for methane storage. The method includes providing a MOF comprising a building block that includes a compound of a formula

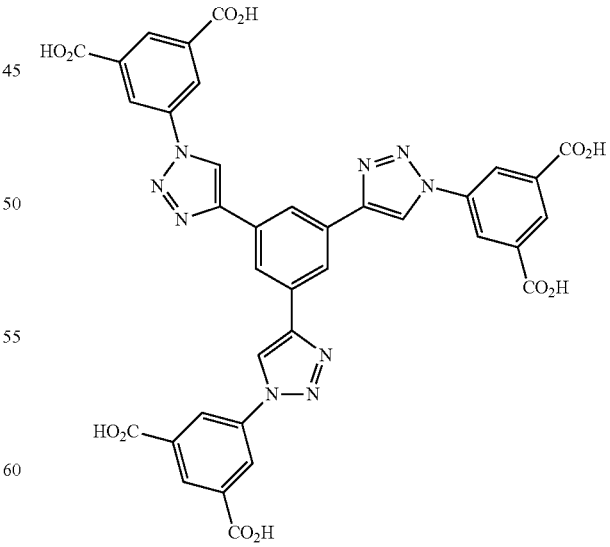

and a metal component; and contacting said MOF and methane under at least one of a pressure and a temperature sufficient for methane storage with said MOF.

In another aspect, said metal component of said building block is $Cu_2$.

In another aspect, said methane storage is at least about 240v[STP]/v at least about 65 bar.

In one embodiment, a container for at least one of uptaking, storing and releasing at least one gas is provided. The container includes at least one of an inlet component and an outlet component; a pressure control component to maintain a gas under pressure in said container; and a metal organic framework material comprising a metal organic framework (MOF) that includes a polymeric crystalline structure comprising the coordination product of a metal component comprising a metal center selected from $Zn_4O$, $Zn_2$, $Cu_2$, $V_3O_3$ and $Zr_6O_6$, an organic ligand component selected from the ligands of FIGS. 3B-C and combinations thereof, and optionally a solvent, and optionally a gas.

In another aspect, the container includes a gas therein that is selected from hydrogen, oxygen, nitrogen, the noble gases, acetylene, methane, ethane, propane, natural gases, synthesis gases, carbon monoxide, carbon dioxide, arsine, hydrogen selenide, and combinations thereof.

In another aspect, said gas comprises natural gas.

In another aspect, said metal organic framework material comprises a MOF that includes a polymeric crystalline structure of a $Cu_2$ metal component, a ligand component of a formula

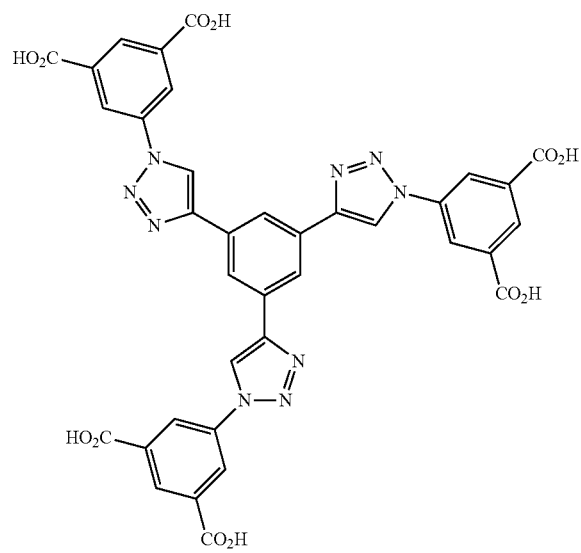 [SMILES: O=C(O)c1cc(C(=O)O)cc(-n2cc(-c3cc(-c4cn(-c5cc(C(=O)O)cc(C(=O)O)c5)nn4)cc(-c4cn(-c5cc(C(=O)O)cc(C(=O)O)c5)nn4)c3)nn2)c1]

and optionally a solvent.

In another aspect, the container includes a gas therein that is selected from hydrogen, oxygen, nitrogen, the noble gases, acetylene, methane, ethane, propane, natural gases, synthesis gases, carbon monoxide, carbon dioxide, arsine, hydrogen selenide, and combinations thereof.

In another aspect, said gas comprises natural gas.

In another aspect, the container is incorporated into a gas storage system.

In another aspect, the container is incorporated into a fuel cell.

In another aspect, the container is incorporated into a fuel cell of an automotive vehicle.

In another aspect, the container is selected from cylindrical and non-cylindrical configurations.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter described herein without departing from its scope. While the dimensions and types of materials described herein are intended to define the parameters of one or more embodiments of the inventive subject matter, they are by no means limiting and are example embodiments. Many other embodiments will be apparent to one of ordinary skill in the art upon reviewing the above description. The scope of the subject matter described herein should, therefore, be determined with reference to the appended clauses, along with the full scope of equivalents to which such clauses are entitled. In the appended clauses, the terms "including" and "in which" are used as the plain-English equivalents of the respective terms "comprising" and "wherein." Moreover, in the following clauses, the terms "first," "second," and "third," etc. are used merely as labels, and are not intended to impose numerical requirements on their objects. Further, the limitations of the following clauses are not written in means-plus-function format and are not intended to be interpreted based on 35 U.S.C. §112, sixth paragraph, unless and until such clause limitations expressly use the phrase "means for" followed by a statement of function void of further structure.

This written description uses examples to disclose several embodiments of the inventive subject matter and also to enable any person of ordinary skill in the art to practice the embodiments disclosed herein, including making and using any devices or systems and performing any incorporated methods. The patentable scope of the subject matter is defined by the clauses, and may include other examples that occur to one of ordinary skill in the art. Such other examples are intended to be within the scope of the clauses if they have structural elements that do not differ from the literal language of the clauses, or if they include equivalent structural elements with insubstantial differences from the literal languages of the clauses.

The foregoing description of certain embodiments of the disclosed subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described systems and methods, without departing from the spirit and scope of the subject matter herein involved, it is intended that all of the subject matter of the above description or shown in the accompanying drawings shall be interpreted merely as examples illustrating the inventive concepts herein and shall not be construed as limiting the disclosed subject matter.

The invention claimed is:

1. A system for generating and/or screening one or more potential metal-organic frameworks (MOFs), the system comprising:
   a generation module configured to receive identifications of building blocks for determining if the building blocks can be used to form one or more of the potential MOFs, the generation module further configured to determine which of the potential MOFs can be formed by simulating a combining of the building blocks in different arrangements, and wherein the generation module is configured to automatically simulate the combining of the building blocks that are identified without involving energy minimization; and
   a fabrication system coupled with the generation module, the fabrication system including one or more sources of actual building blocks that are identified, the fabrication system configured to automatically combine the actual building blocks that are used to form the potential MOFs as simulated by the generation module.

2. The system of claim 1, wherein the building blocks include inorganic building blocks, organic building blocks, and functional groups.

3. The system of claim 2, wherein the generation module is configured to connect the inorganic building blocks with the organic building blocks.

4. The system of claim 1, wherein the generation module is configured to simulate the combining of the building blocks that are identified based on at least one of topological information or geometrical information assigned to the building blocks.

5. The system of claim 1, wherein the generation module is configured to determine whether two or more of the building blocks that are identified cannot be combined with each other without resulting in collisions between atoms of the building blocks in the simulating of the combining of the building blocks.

6. The system of claim 1, further comprising an evaluation module configured to calculate one or more material properties of the potential MOFs.

7. The system of claim 6, wherein the one or more material properties include one or more of surface area, pore volume, pore size distribution, powder x-ray diffraction pattern, or adsorption capability.

8. The system of claim 6, wherein the evaluation module is configured to perform an atomistic grand Monte Carlo simulation to calculate at least one of the one or more material properties.

9. The system of claim 1, wherein the building blocks are derived from crystallographic data of previously synthesized MOFs.

10. The system of claim 1, wherein the generation module is configured to:
    receive identifications of different types of the building blocks;
    encode a total number of the building blocks and a total number of possible arrangements of the building blocks;
    select a composition and arrangement of the building blocks;
    determine whether a combination of two or more of the building blocks of the selected composition and arrangement of the building blocks cannot be combined with each other without resulting in collision between atoms of the building blocks or resulting in incompatible chemistry;
    discard the selected composition and arrangement of the building blocks if the collision between atoms or incompatible chemistry are identified and select another arrangement of the building blocks; and
    export the composition and arrangement of the building blocks if the collision between atoms or incompatible chemistry are not identified.

11. The system of claim 10, wherein:
    the generation module is further configured to incrementally vary the arrangement of the building blocks by a random number up to a predetermined number of times until the selected composition and arrangement of the building blocks is exported, and to vary at least one building block composition if the selected composition and arrangement of the building blocks is not exported after the varying the arrangement of the building blocks by a random number the predetermined number of times;
    the building blocks include inorganic building blocks, organic building blocks, and functional groups; and
    the generation module is configured to connect the inorganic building blocks with the organic building blocks.

12. A method for generating and/or screening one or more potential metal-organic frameworks (MOFs), the method comprising:
    receiving building blocks used to form one or more of the potential MOFs;
    determining which of the potential MOFs can be formed by simulating a combining of different arrangements of the building blocks, wherein determining which of the potential MOFs can be formed includes automatically simulating combining of the building blocks without involving energy minimization;
    outputting an identification of the potential MOFs that can be formed from the building blocks based on the simulating of the combining of the building blocks; and
    outputting instructions to a fabrication system for automatically creating one or more of the potential MOFs from one or more sources of the building blocks.

13. The method of claim 12, wherein the building blocks include inorganic building blocks, organic building blocks, and functional groups.

14. The method of claim 13, wherein forming the potential MOFs includes combining the inorganic building blocks with the organic building blocks.

15. The method of claim 12, wherein determining which of the potential MOFs can be formed includes combining the building blocks based on at least one of topological information or geometrical information assigned to the building blocks.

16. The method of claim 12, further comprising calculating one or more material properties of the potential MOFs.

17. The method of claim 16, wherein the one or more material properties include surface area, pore volume, pore size distribution, powder x-ray diffraction pattern, or adsorption capability.

18. The method of claim 16, wherein calculating the one or more material properties includes performing an atomistic grand Monte Carlo simulation to calculate at least one of the one or more material properties.

19. The method of claim 12, further comprising deriving the building blocks from crystallographic data of previously synthesized MOFs.

20. The method of claim 12, further comprising:
receiving identifications of different types of the building blocks;
encoding a total number of the building blocks and a total number of possible arrangements of the building blocks;
selecting a composition and arrangement of the building blocks;
determining whether a combination of two or more of the building blocks of the selected composition and arrangement of the building blocks cannot be combined with each other without resulting in collision between atoms of the building blocks or resulting in incompatible chemistry;
discarding the selected composition and arrangement of the building blocks if the collision between atoms or incompatible chemistry are identified and selecting another arrangement of the building blocks; and
exporting the composition and arrangement of the building blocks if the collision between atoms or incompatible chemistry are not identified.

21. The method of claim 20, further comprising:
incrementally varying the arrangement of the building blocks by a random number up to a predetermined number of times until the selected composition and arrangement of the building blocks is exported; and
varying at least one building block composition if the selected composition and arrangement of the building blocks is not exported after the varying the arrangement of the building blocks by a random number the predetermined number of times.

22. A non-transitory computer readable storage medium for a system having a processor, the computer readable storage medium including one or more sets of instructions configured to direct the processor to:
receive an identification of building blocks for one or more of the potential MOFs;
determine which of the potential MOFs can be formed by performing a simulation of combining of the building blocks;
output an identification of the potential MOFs that can be formed from the building blocks based on the building blocks that can be combined with each other in the simulation; and
automatically simulate the combining of the building blocks without involving energy minimization,
wherein the one or more sets of instructions are further configured to direct the processor to automatically direct a fabrication system having one or more sources of the building blocks to create one or more of the potential MOFs.

23. The computer readable storage medium of claim 22, wherein the building blocks include inorganic building blocks, organic building blocks, and functional groups.

24. The computer readable storage medium of claim 23, wherein the one or more sets of instructions are configured to direct the processor to combine the inorganic building blocks with the organic building blocks.

25. The computer readable storage medium of claim 22, wherein the one or more sets of instructions are configured to direct the processor to combine the building blocks based on at least one of topological information or geometrical information assigned to the building blocks.

26. The computer readable storage medium of claim 22, wherein the one or more sets of instructions are configured to direct the processor to calculate one or more material properties of the potential MOFs.

27. The computer readable storage medium of claim 22, wherein the one or more sets of instructions are configured to calculate one or more material properties of the potential MOFs including one or more of surface area, pore volume, pore size distribution, powder x-ray diffraction pattern, or adsorption capability.

28. The computer readable storage medium of claim 27, wherein the one or more sets of instructions are configured to direct the processor to perform an atomistic grand Monte Carlo simulation to calculate at least one of the one or more material properties.

29. The computer readable storage medium of claim 22, wherein the building blocks are derived from crystallographic data of previously synthesized MOFs.

* * * * *